(12) United States Patent
Bonnin et al.

(10) Patent No.: US 8,546,532 B2
(45) Date of Patent: *Oct. 1, 2013

(54) SYNTHESIS OF DIRECTED SEQUENCE POLYMER COMPOSITIONS AND ANTIBODIES THEREOF FOR THE TREATMENT OF PROTEIN CONFORMATIONAL DISORDERS

(75) Inventors: Dustan Bonnin, Belmont, MA (US); Eric Zanelli, Sudbury, MA (US); Thomas Mathers, Boston, MA (US)

(73) Assignee: Declion Pharmaceuticals, Inc., Boxford, MA (US)

(*) Notice: Subject to any disclaimer, the term of this patent is extended or adjusted under 35 U.S.C. 154(b) by 629 days.

This patent is subject to a terminal disclaimer.

(21) Appl. No.: 12/386,493

(22) Filed: Apr. 17, 2009

(65) Prior Publication Data
US 2010/0080796 A1    Apr. 1, 2010

Related U.S. Application Data

(60) Provisional application No. 61/168,555, filed on Apr. 10, 2009, provisional application No. 61/124,689, filed on Apr. 17, 2008.

(51) Int. Cl.
*A61K 38/00* (2006.01)
*A61K 51/00* (2006.01)

(52) U.S. Cl.
USPC ........... 530/334; 530/333; 530/300; 530/324; 530/325; 530/326; 530/327; 530/328; 530/329; 530/330; 530/350

(58) Field of Classification Search
None
See application file for complete search history.

(56) References Cited

U.S. PATENT DOCUMENTS

| | | | |
|---|---|---|---|
| 5,736,142 A | 4/1998 | Sette et al. | |
| 6,093,396 A | 7/2000 | Falorni et al. | |
| 6,184,351 B1 | 2/2001 | Biere et al. | |
| 6,818,219 B1 | 11/2004 | Tranchand-Bunel et al. | |
| 7,060,464 B2 | 6/2006 | Kim | |
| 7,118,874 B2 | 10/2006 | Torres | |
| 7,166,471 B2 | 1/2007 | Orser et al. | |
| 7,226,746 B1 | 6/2007 | Masliah et al. | |
| 7,306,945 B2* | 12/2007 | Chilcote et al. | 435/440 |
| 7,358,331 B2 | 4/2008 | Chilcote et al. | |
| 7,479,482 B2 | 1/2009 | Frangione et al. | |
| 7,674,599 B2 | 3/2010 | Chilcote et al. | |
| 7,691,639 B2 | 4/2010 | Orser et al. | |
| 7,727,957 B2 | 6/2010 | Schenk et al. | |
| 2002/0183484 A1 | 12/2002 | Torres | |
| 2003/0027210 A1 | 2/2003 | Benjamin et al. | |
| 2003/0166558 A1 | 9/2003 | Frangione et al. | |
| 2003/0223995 A1 | 12/2003 | Skurkovich et al. | |
| 2004/0136993 A1 | 7/2004 | Schenk et al. | |
| 2004/0146521 A1 | 7/2004 | Schenk et al. | |
| 2005/0037013 A1 | 2/2005 | Schenk et al. | |
| 2005/0196818 A1 | 9/2005 | Chilcote et al. | |
| 2006/0058233 A1 | 3/2006 | Schenk et al. | |
| 2006/0115899 A1 | 6/2006 | Buckner et al. | |
| 2006/0159672 A1 | 7/2006 | Rasmussen et al. | |
| 2006/0259986 A1 | 11/2006 | Chilcote et al. | |
| 2007/0214509 A1 | 9/2007 | Langston | |
| 2008/0014194 A1 | 1/2008 | Schenk et al. | |
| 2008/0022035 A1 | 1/2008 | Yu et al. | |
| 2008/0095706 A1 | 4/2008 | Orser et al. | |
| 2008/0146504 A1* | 6/2008 | Bonnin | 514/12 |
| 2009/0036653 A1* | 2/2009 | Bonnin | 530/388.9 |
| 2009/0104216 A1 | 4/2009 | Torres | |
| 2009/0208487 A1 | 8/2009 | Schenk et al. | |
| 2009/0208960 A1 | 8/2009 | Kelly et al. | |
| 2010/0086545 A1 | 4/2010 | Schenk et al. | |
| 2010/0298547 A1* | 11/2010 | Bonnin | 530/388.1 |
| 2011/0129497 A1* | 6/2011 | Bonnin et al. | 424/209.1 |

FOREIGN PATENT DOCUMENTS

| | | |
|---|---|---|
| EP | 1 676 859 | 7/2006 |
| EP | 1 679 319 | 7/2006 |
| EP | 2154153 | 2/2010 |
| FR | 2677363 | 12/1992 |
| WO | WO-2003/045128 | 6/2003 |
| WO | WO-2004/009625 | 1/2004 |
| WO | WO-2005/032482 | 4/2005 |
| WO | WO-2005/074579 | 8/2005 |
| WO | WO-2005/085323 | 9/2005 |
| WO | WO-2005/112972 | 12/2005 |
| WO | WO-2006/020581 | 2/2006 |

(Continued)

OTHER PUBLICATIONS

Bard et al. Epitope and isotype specificities of antibodies to beta-amyloid peptide for protection against Alzheimer's disease-like neuropathology. Proc Natl Acad Sci U S A. Feb. 18, 2003;100(4):2023-8.*

Fields. Introduction to peptide synthesis. Curr Protoc Mol Biol. Aug. 2002;Chapter 11:Unit 11.15.*

Alexander, J. et al., "Linear PADRE T Helper Epitope and Carbohydrate B Cell Epitope Conjugates Induce Specific High Titer IgG Antibody Responses", The Journal of Immunology, 2000, 164: 1625-1633.

De Koster, H. et al., "Definition of agonists and design of antagonists for alloreactive T cell clones using synthetic peptide libraries", International Immunology, vol. 11, No. 4, 585-591 (1999).

(Continued)

*Primary Examiner* — Michelle S Horning
(74) *Attorney, Agent, or Firm* — Ropes & Gray LLP

(57) ABSTRACT

The instant invention comprises a process for the solid phase synthesis of directed epitope peptide mixtures useful in the treatment and diagnosis of protein conformational disorders, such process defined by a set of rules regarding the identity and the frequency of occurrence of amino acids that substitute a base or native amino acid of a known epitope. The resulting composition is a mixture of related peptides for therapeutic use. The invention also pertains to the process of generating antibodies using the directed epitope peptide mixtures as the antigens, and antibodies generated by such process, useful in the treatment and diagnostics of the said protein conformational disorder.

17 Claims, 11 Drawing Sheets

(56) References Cited

FOREIGN PATENT DOCUMENTS

| | | |
|---|---|---|
| WO | WO-2006/031727 | 3/2006 |
| WO | WO-2006/045037 | 4/2006 |
| WO | WO-2006/050138 | 5/2006 |
| WO | WO2006/128294 | 12/2006 |
| WO | WO-2006/128294 | 12/2006 |
| WO | WO-2007/021255 | 2/2007 |
| WO | WO-2007/090126 | 8/2007 |
| WO | WO-2007/120834 | 10/2007 |
| WO | WO2007/120834 | 10/2007 |
| WO | WO-2008/015384 | 2/2008 |
| WO | WO-2008/022035 | 2/2008 |
| WO | WO-2008/103472 | 8/2008 |
| WO | WO-2008/114003 | 9/2008 |
| WO | WO-2009/023047 | 2/2009 |
| WO | WO-2009/027105 | 3/2009 |
| WO | WO-2009/051797 | 4/2009 |
| WO | WO-2009/103105 | 8/2009 |
| WO | WO-2009/133521 | 11/2009 |
| WO | WO-2010/011999 | 1/2010 |
| WO | WO-2010/012004 | 1/2010 |
| WO | WO-2010/040209 | 4/2010 |

OTHER PUBLICATIONS

Estaquier, J., et al., "Combinatorial Peptide Library as an Immunogen," Methods in Molecular Biology, 87:281-296 (1998).

Estaquier, Jerome, et al., "A Combinatorial Peptide Library Around Variation of the Human Immunodeficiency Virus (HIV-1) V3 Domain Leads to Distinct T Helper Cell Responses," Journal of Peptide Science, 2:165-175 (1996).

Frenkel, D. et al., "Nasal vaccination with a proteosome-based adjuvant and glatiramer acetate clears β-amyloid in a mouse model of Alzheimer disease", J. Clin. Invest. 115:2423-2433 (2005).

Gras-Masse, H., et al., "Confronting the degeneracy of convergent combinatorial immunogens, or 'mixotopes', with the specificity of recognition of the target sequences," Vaccine, 15(14):1568-1578 (1997).

Gras-Masse, Helene, et al., "Convergent peptide libraries, or mixotopes, to elicit or to identify specific immune responses," Immunology, 11:223-228 (1999).

Hernandez, J., et al. "Antigenicity and immunogenicity of peptide analogues of a low affinity peptide of the human telomerase reverse trascriptase tumor antigen", Eur. J. Immunol. 34:2331-2341, (2004).

Hoogenboom, H., "Selecting and screening recombinant antibody libraries", Nature Biotechnology, vol. 23, No. 9 1105-1116 2005.

Hust, M., et al., "Mating antibody phage display with proteomics", Trends in Biotechnology, vol. 22 No. 1, 8-14 2004.

Kirsch, M., et al., "Parameters affecting the display of antibodies on phage", Journal of Immunological Methods, 301,173-185, 2005.

Knappik, A., et al., "FullySynthetic Human Combinatorial Antibody Libraries (HuCAL) Based on Modular Consensus Frameworks and CDRs Randomized with Trinucleotides", J. Mol. Biol. 296 57-86, 2000.

Konthur, Z., et al., "Perspectives for systematic in vitro antibody generation", Gene, 364, 19-29,2005.

Loiseau, P., et al., "HLA class II polymorphism contributes to specify desmoglein derived peptides in pemphigus vulgaris and pemphigus floiaceus", Journal of Autoimmunity, 15, 67-73 (2000).

Lustgarten et al: "Identification of cross-reactive pepides using combinatioral libraries circumvents tolerance against Her-21neu-immunodominant epitope", Journal of Immunology, vol. 176, No. 3, 1796-1805 (2006).

Maynard, J., et al., "Structure of an Autoimmune T Cell Receptor Complexed with Class II Peptide-MHC: Insights into MHC Bias and Antigen Specificity", Immunity, vol. 22, 81-92 (2005).

Meyer, D., et al., "Hypervariable Epitope Constructs Representing Variability in Envelope Glycoprotein of SIV Induce a Broad Humoral Immune Response in Rabbits and Rhesus Macaques", Aids Research and Human Retroviruses, vol. 14, No. 9, pp. 751-760, 1998.

Morrison K L et al: "Combinatorial alanine-scanning" Current Opinion in Chemical Biology, Current Biology Ltd, London, GB, vol. 5, No. 3, Jun. 1, 2001, pp. 302-307.

O'Sullivan, D., et al., "On the interaction of promiscuous antigenic peptides with different dr alleles", The Journal of Immunology, vol. 147, No. 8, 2663-2669, (1991).

Olszewska, W., et al., "Nasal delivery of epitope based vaccines", Advanced Drug Delivery Reviews, 51:161-171 (2001).

Osbourn, J., et al., "Current methods for the generation of human antibodies for the treatment of autoimmune diseases", DDT, vol. 8, No. 18,845-851 2003.

Pinchuk, P., et al., "Antigenicity of polypeptides (poly alpha amino acids )", Microbiology Department, New Jersey College of Medicine and Dentistry, 673-679 (1965).

Pinilla, C., et al., "Advances in the use of synthetic combinatorial chemistry: Mixture-based libraries", Nature Medicine, vol. 9, No. 1, pp. 118-126, (2003).

Pons J et al: "Energetic analysis of an antigen/antibody interface: alanine scanning mutagenesis and double mutant cycles on the HyHEL-10/lysozyme interaction." Protein Science o a Publication of the Protein Society May 1999, vol. 8, No. 5, May 1999, pp. 958-968.

Sakurai, Y. et al., "Analog Peptides of type II collagen can suppress arthritis in HLA-DR4 (DRB1*0401) transgenic mice", Arthritis Research & Therapy, 8:R150, (2006).

Tam, J. et al., "Incorporation of T and B Epitopes of the Circumsporozoite Protein in a Chemically Defined Synthetic Vaccine Against Malaria", J. Exp. Med., 171:299-306 (1990).

Tranchand-Bunel D, et al., "Evaluation of an Epstein-Barr Virus (EBV) Immunoglobulin M Enzyme-Linked Immunosorbent Assay Using a Synthetic Convergent Peptide Library, or Mixotope, for Diagnosis of Primary EBV Infection," J Clin Microbiol., 37(7):2366-2368 (Jul. 1999).

Wilson, D. et al, "Specificity and degeneracy of T cells", Molecular Immunology 40:1047-1055, (2004).

Anderson, D.E. et al., "Overcoming Original (Antigenic) Sin", Clinical Immunology, 101:2, 152-57 (2001).

Anderson, J.P. et al, "Phosphorylation of Ser-129 Is the Dominant Pathological Modification of α-Synuclein in Familial and Spradic Lewy Body Disease", Journal of Biological Chemistry, 281:40, 29739-52 (Oct. 6, 2006).

Batthyany et al., "Reversible Post-translational Modification of Proteins by Nitrated Fatty Acids in Vivo" Journal of Biological Chemistry, 281:29, 20450-63 (Jul. 31, 2006).

Benner et al., "Nitrated α-Synuclein Immunity Accelerates Degeneration of Nigral Dopaminergic Neurons," Immunity and Neurodegeneration, Issue 1, 1-20 (Jan. 2008).

Benner et al., "Therapeutic immunization protects dopaminergic neurons in a mouse model of Parkinson's disease" PNAS, 101:25, 9435-40 (Jun. 22, 2004).

Bianchi et al., "Universal Influenza B Vaccine Based on the Maturational Cleavage Site of the Hemagglutinin Precursor" Journal of Virology, 79:12, 7380-88 (2005).

Bisaglia et al., "Structure and topology of the non-amyloid-β component fragment of human α-synuclein bound to micelles: Implications for the aggregation process." Protein Science, 15:1408-16 (2006).

Cardinale et al., "The potential of intracellular antibodies for therapeutic targeting of protein-misfolding diseases." Trends in Molecular Medicine, 14:9, 373-80 (May 2008).

Carlos, M.P. et al., "Immunogenicity of a Vaccine Preparation Representing the Variable Regions of the HIV Type 1 Envelope Glycoprotein" AIDS Research and Human Retroviruses, 16:2, 153-61 (Jan. 2000).

Carrell et al., "Conformational disease" The Lancet, 350: 134-38 (1997).

Cui et al., "Nitrated Fatty Acids: Endogenous Anti-inflammatory Signaling Mediators" Journal of Biological Chemistry. 281:47, 35686-98 (Nov. 2006).

Del Mar et al., "Structure and properties of α-synuclein and other amyloids determined at the amino acid level." PNAS, 102:43, 15477-82 (Oct. 2005).

Desai et al., "Blood-Brain Barrier Pathology in Alzheimer's and Parkinson's Disease: Implications for Drug Therapy" Cell Transplantation. 16, 285-99 (2007).

Duda et al., "Widespread Nitration of Pathological Inclusions in Neurodegenerative Synucleinopathies" American Journal of Pathology. 157:5, 1439-45 (Nov. 2000).

El-Agnaf et al. "Aggregation and neurotoxicity of α-synuclein and related peptides" Biochemical Society Transactions. 30:4, 559-65 (2002).

Giasson et al. "Oxidative Damage Linked to Neurodegeneration by Selective α-Synuclein Nitration in Synucleinopathy Lesions" Science. 290:3, 985-89 (Nov. 2000).

Goldberg et al., "Is there a cause-and-effect relationship between α-synuclein fibrillization and Parkinson's disease?", Nature Cell Biology, 2:E115-19 (Jul. 2000).

Gorbatyuk et al., "The phosphorylation state of Ser-129 in human α-synuclein determines neurodegeneration in a rat model of Parkinson disease", PNAS, 105:2, 763-68 (Jan. 15, 2008).

Hirsch et al., "Neuroinflammation in Parkinson's disease: a target for neuroprotection?", The Lancet, 8:382-97 (Apr. 2009).

Johnson, W.G., "Late-onsert neurodegenerative diseases—the role of protein insolubility", J. Anat. 196:609-16 (2000).

Kim, et al., "Persistence of Immune Responses to Altered and Native Myelin Antigens in Patients with Multiple Sclerosis Treated with Altered Peptide Ligand", Clinical Immunology, 104:2, 105-114 (2002).

Laurie et al., "CD4+ T cells from Copolymer-1 immunized mice protect dopaminergic neurons in the 1-methyl-4-phenyl-1,2,3,6-tetrahydropyridine model of Parkinson's disease", Journal of Neuroimmunology, 183:60-8 (2007).

Lee, S-J., "Origins and Effects of Extracellular α-synuclein: Implications in Parkinson's Disease", Journal of Molecular Neuroscience, 34:17-22 (2008).

Levin et al., "Increased α-synuclein aggregation following limited cleavage by certain matrix metalloproteinases", Experimental Neurology, 215:201-8 (2009).

Madine et al., "Studies of the aggregation of an amyloidogenic α-synuclein peptide fragment", Biochemical Society Transactions, 33:5, 1113-15 (2005).

Madine et al., "The aggregation and membrane-binding properties of an α-synuclein peptide fragment", Biochemical Society, 32,6:1127-9 (2004).

Maslian et al., "Effects of α-Synuclein Immunization in a Mouse Model of Parkinson's Disease", Neuron, 46:857-68 (2005).

Meyer et al., "Induction of Cytotoxic and Helper T Cell Responses by Modified Simian Immunodeficiency Virus Hypervariable Epitope Constructs", Viral Immunology, 12:2, 117-29 (1999).

Pantophlet et al., "Improved design of an antigen with enhanced specificty for the broadly HIV-neutralizing antibody b12", Protein Engineering, Design & Selection, 17:10, 749-58 (2004).

Permanne et al., "Reduction of amyloid load and cerebral damage in a transgenic mouse model of Alzheimer's disease by treatment with a β-sheet breaker peptide", FASEB Journal (Apr. 10, 2002).

UniProtKB/Swiss-Prot entry P37840 [SYUA_HUMAN] Alpha-synuclein. Retrieved from http://www.expasy.org/uniprot/P37840.

UniProtKB/Swiss-Prot entry O55042 [SYUA_MOUSE] Alpha-synuclein. Retrieved from http://www.expasy.org/uniprot/O55042.

UniProtKB/Swiss-Prot entry P37377 [SYUA_RAT] Alpha-synuclein. Retrieved from http://www.expasy.org/uniprot/P37377.

Thomas et al., "Parkinson's Disease", Human Molecular Genetics, 16:2, R183-94 (2007).

Tsai, S.-J., "Glatiramer acetate could be a potential therapeutic agent for Parkinson's disease through its neuroprotectiev and anti-inflammatory effects", Medical Hypotheses, 69:1219-21 (2007).

Villar et al., "The fold of α-synuclein fibrils", PNAS, 105:25, 8637-42 (Jun. 2008).

Wang, C-E. et al., "Suppression of neuropil aggregates and neurological symptoms by an intracellular antibody implicates the cytoplasmic toxicity of mutant huntingtin", Journal of Cell Biology, 181:52, 803-16 (2008).

Wilms et al., "Inflammation in Parkinson's Diseases and Other Neurodegenerative Diseases: Cause and Therapeutic Implications", Current Pharmaceutical Design, 13:1925-28 (2007).

Yacoubian et al., "Targets for neuroprotection in Parkinson's disease", Biochemica et Bioshysica Acta (2008).

Zhou et al., "A Human Single-Chain Fv Intrabody Blocks Aberrant Cellular Effects of Overexpressed α-Synuclein", Molecular Therapy, 10:6, 1023-31 (2004).

Jardetzky, T.S., et al. "Peptide binding to HLA-DR1: a peptide with most residues substituted to alanine retains MJC binding," The EMBO Journal, vol. 9(6), pp. 1797-1803 (1990).

Corlin, D. B. et al., "Quantification of Cleaved β2-Microglobulin in Serum from Patients Undergoing Chronic Hemodialysis", Clinical Chemistry 51(7):1177-1184 (2005).

Danesh, F. et al., "Dialysis-Related Amyloidosis: History and Clinical Manifestations"; Seminars in Dialysis 14(2):80-85 (2001).

Eakin, C.M.ee et al., "Oligomeric Assembly of Native-like Precursors Precedes Amyloid Formation by β-2 Microglobulin", Biochemistry, 43:7808-7815 (2004).

Gandy, S., "The Role of Cerebral Amyloid β Accumulation in Common Forms of Alzheimer Disease", J. Clin. Invest. 115(5):1121-1129 (2005).

Gilch et al., "Polyclonal Anti-PrP Auto-antibodies Induced with Dimeric PrP Interfere Efficiently with PrPSc Propagation in Prion-infected Cells", J. Biol. Chem. 278(20):18524-18531 (2003).

Haass, "β-Amyloid Peptide and a 3-kDa Fragment are Derived by Distinct Cellular Mechanisms", J. Biol. Chem 268(5):3021-3024 (1993).

Harmeyer et al., "Synthetic peptide vaccines yield monoclonal antibodies to cellular and pathological prion proteins of ruminants", J. General Virology 79:937-945 (1998).

Hartmann et al., "Distinct sites of intracellular production for Alzheimer's disease Abeta40/42 amyloid peptides", Nature Medicine 3(9):1016-1017 (1997) (abstract).

Hoshino, M. et al., "Mapping the core of the β2-microglobulin amyloid fibril by H/D exchange", Nature Structural Biology 9(5):332-336 (2002).

Jekabsone, A., "Fibrillar beta-amyloid peptide $A\beta_{1-40}$ activates microglial proliferation via stimulating TNF-B release and H2O2 derived from NADPH oxidase: a cell culture study", J. Neuroinflammation 3:24 (2006).

Kozhukh, G. V. et al., "Investigation of a Peptide Responsible for Amyloid Fibril Formation of β2-Microglobulin by Acromobacter Protease I", The Journal of Biological Chemistry, 277(2):1310-1315 (2002).

Kutsuki, H., "β2-Microglobulin-selective direct hemoperfusion column for the treatment of dialysis-related amyloidosis", Biochimica et Biophysica Acta 1753:141-145 (2005).

Lysaght, M. J. et al., "β-2 Microglobulin Removal During Continuous Ambulatory Peritoneal Dialysis (CAPD)", Peritoneal Dialysis International 9:29-35 (1989).

Mimmi, M. C. et al., "Variants of β2-microglobulin cleaved at lysine-58 retain the main conformational features of the native protein but are more conformationally heterogeneous and unstable at the physiological temperature", The FEBS Journal 273:2461-2474 (2006).

Naslund, "Relative abundance of Alzheimer Aβ amyloid peptide variants in Alzheimer disease and normal aging," PNAS 91:8378-8382 (1994).

Niwa, T., "Dialysis-Related Amyloidosis: Pathogenesis Focusing on AGE Modification", Seminars in Dialysis 14(2):123-126 (2001).

Pankiewicz et al, "Clearance and prevention of prion infection in cell culture by anti-PrP antibodies", NIH Public Access 1-28 (2007).

Rashid, G. et al., "Advanced Glycation End Products Stimulate Tumor Necrosis Factor-Alpha and Interleukin-1 β Secretion by Peritoneal Macrophages in Patients on Continuous Ambulatory Peritoneal Dialysis", IMAJ 8:36-39 (2006).

Tjernberg, et al, "Assembling amyloid fibrils from designed structures containing a significant amyloid B-peptide fragment", Biochem. J. 366:343-351 (2002).

Uji, Y. et al., "A Circulating β2-Microglobulin Intermediate in Hemodialysis Patients", Nephron Clin Pract 111:c173-c181 (2009).

UniProtKB/Swiss-Prot entry P61769 [B2MG_HUMAN]. Retrieved from http://www.uniprot.org/uniprot/P61769.

Yamamoto, S. et al., "Historical background and clinical treatment of dialysis-related amyloidosis", Biochimica et Biophysica Acta 1753:4-10 (2005).

* cited by examiner

Figure 1
A: Use of Peptide Library for Epitope Discovery
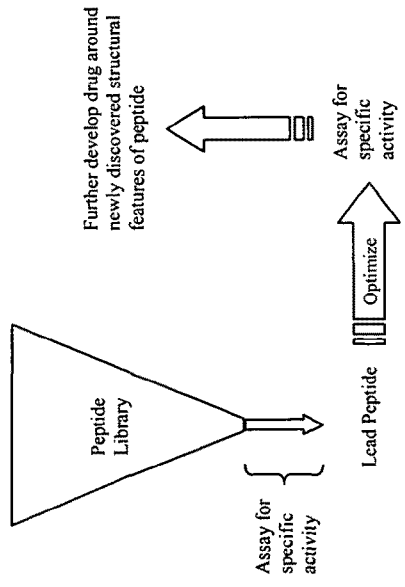
B: Generation of Altered Peptide Ligand-based Therapeutic
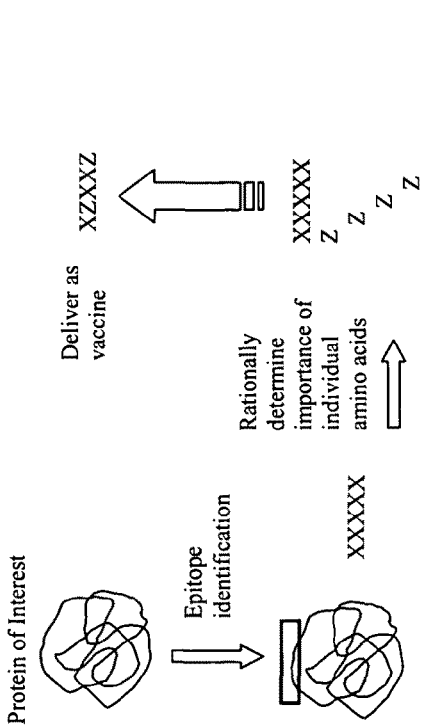
C: Multivalent Peptide Presentation using Dendrimers
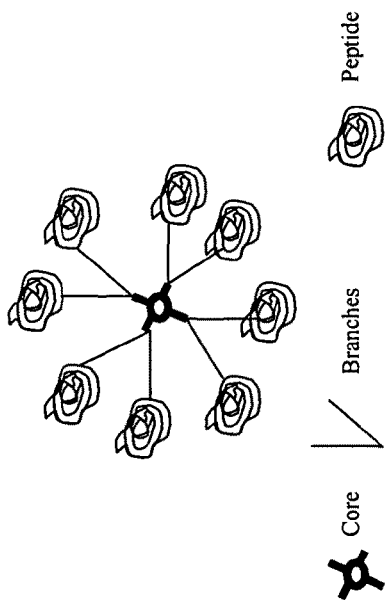
D: Random Sequence Polymer Generation
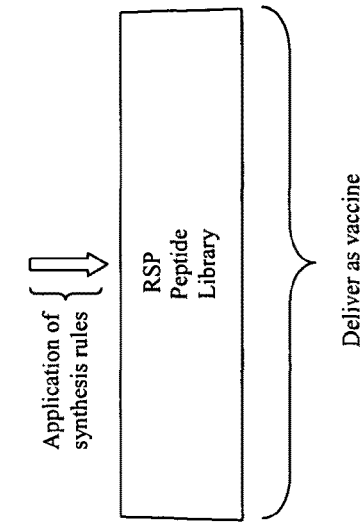

Steps for Creation of Directed Sequence Polymer

Figure 4

Preferred Defined Substitutive Rules for Directed Expansion of Epitope Permeability

| Amino Acid groupings used for exchanging amino acids during the creation of rules for the solid phase synthesis of DSP. Amino Acids grouped together are interchangeable. | | | | |
|---|---|---|---|---|
| | a | b | c | d |
| I | | R,H | | K |
| II | | W | | |
| III | | F,Y | | |
| IV | | | V,I,L,M | |
| V | | | C | |
| VI | T,S,G,P | | | |
| VII | | | | E,D,Q,N |
| Alanine | Alanine can be substituted for any amino acid | | | |

Figure 5

Generic Rule Structure and Ranges of Substitutions of DSP Synthesis

| | Sequence of amino acids to be synthesized (Amino Acid Sequence Synthesis Block $y_N$) | | | | | | Input Ratio |
|---|---|---|---|---|---|---|---|
| Base (a) | $x_1$ | $x_2$ | $x_3$ | $x_4$ | $x_5$ | $x_N$ | a = 0.0 - 80 |
| 1° Change (b)_ | $1°x_1$ | $1°x_2$ | $1°x_3$ | $1°x_4$ | $1°x_5$ | $1°x_N$ | b = 0.0 - 80 |
| 2° Change (c) | $2°x_1$ | $2°x_2$ | $2°x_3$ | $2°x_4$ | $2°x_5$ | $2°x_N$ | c = 0.0 - 80 |
| 3° Change (d) | $3°x_1$ | $3°x_2$ | $3°x_3$ | $3°x_4$ | $3°x_5$ | $3°x_N$ | d = 0.0 - 80 |
| Alanine (e) | Ala | Ala | Ala | Ala | Ala | Ala | e = 20 - 100 |

Full Length Order of DSP

| | N-terminal Modifier | Amino Acid Sequence Synthesis Block | | | | | | C-terminal Modifier |
|---|---|---|---|---|---|---|---|---|
| DSP | MN | $y_1$ | $y_2$ | $y_3$ | $y_4$ | $y_5$ | $y_n$ | MC |

Figure 6

Example of mock-source peptide DSP Synthesis Rules

Rules of Defined Amino Acid Incorporation

| Input Ratios | y1 Amino Acid (% of total at position) | | | | | Input Ratios | y2 Amino Acid (% of total at position) | | | | |
|---|---|---|---|---|---|---|---|---|---|---|---|
| a(35) | T(35%) | H(45%) | M(40%) | C(50%) | E(35%) | a(4) | P(4%) | W(34%) | K(34%) | N(24%) | A(34%) |
| b(5) | S(5%) | R(5%) | V(5%) | | D(5%) | b(10) | T(10%) | | | Q(10%) | |
| c(5) | G(5%) | | I(5%) | | Q(5%) | c(10) | S(10%) | | | | |
| d(5) | P(5%) | | | | N(5%) | d(10) | G(10%) | | | | |
| e(50) | A(50%) | A(50%) | A(50%) | A(50%) | A(50%) | e(66) | A(66%) | A(66%) | A(66%) | A(66%) | A(66%) |

Rules of Synthesis Block Combination and Modification

| N-Terminal Modification | Body of a Directed Epitope Peptide Mixture or Directed S Schematic for the design of an alpha-synuclein DSP peptide

Figure 7B
Design of an alpha-synuclein DSP peptide

Directed Sequence Polymer design based on alpha-synuclein(121-137) cassette 1.

| POSITION | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Original | D(10) E(10) Q(10) N(10) | N(10) E(10) Q(10) D(10) | E(10) D(10) Q(10) N(10) | A(100) | Y(25) F(25) | E(10) D(10) Q(10) N(10) | M(10) I(10) L(10) V(10) | P(10) T(10) Q(10) S(10) | S(10) Q(10) T(10) P(10) | E(10) D(10) Q(10) N(10) | E(10) D(10) Q(10) N(10) | Q(10) S(10) T(10) P(10) | Y(25) F(25) | Q(10) E(10) D(10) N(10) |
| Alanine* | A(60) | A(60) | A(60) | | A(50) | A(60) | A Ribbon diagram of B2M Figure shows entirety of B2M, with the noted amino acids having n-linked glycans. The DSP source epitope is in black.

Figure 9

Directed Sequence Polymer design based on Aβ1-42

| POSITION | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Original | D(10) | A(100) | E(10) | F(25) | R(25) | H(25) | D(10) | S(10) | G(10) | Y(25) | E(10) | V(10) | H(25) | H(25) |
| | E(10) | | D(10) | Y(25) | H(25) | R(25) | E(10) | T(10) | S(10) | F(25) | D(10) | I(10) | R(25) | R(25) |
| | Q(10) | | Q(10) | | | | Q(10) | G(10) | T(10) | | Q(10) | L(10) | | |
| | N(10) | | N(10) | | | | N(10) | P(10) | P(10) | | N(10) | M(10) | | |
| alanine | A(60) | | A(60) | A(50) | A(50) | A(50) | A(60) | A(60) | A(60) | A(50) | A(60) | A(60) | A(50) | A(50) |
| | 15 | 16 | 17 | 18 | 19 | 20 | 21 | 22 | 23 | 24 | 25 | 26 | 27 | 28 |
| Original | Q(10) | K(40) | L(10) | V(10) | F(25) | F(25) | A(100) | E(10) | D(10) | V(10) | G(10) | S(10) | N(10) | K(40) |
| | E(10) | | V(10) | I(10) | Y(25) | Y(25) | | D(10) | E(10) | I(10) | S(10) | T(10) | E(10) | |
| | D(10) | | I(10) | L(10) | | | | Q(10) | Q(10) | L(10) | T(10) | G(10) | D(10) | |
| | N(10) | | M(10) | M(10) | | | | N(10) | N(10) | M(10) | P(10) | P(10) | Q(10) | |
| alanine | A(60) | A(60) | A(60) | A(60) | A(50) | A(50) | | A(60) | A(60) | A(60) | A(60) | A(60) | A(60) | A(60) |
| | 29 | 30 | 31 | 32 | 33 | 34 | 35 | 36 | 37 | 38 | 39 | 40 | 41 | 42 |
| Original | G(10) | A(100) | I(10) | I(10) | G(10) | L(10) | M(10) | V(10) | G(10) | G(10) | V(10) | V(10) | I(10) | A(100) |
| | S(10) | | V(10) | V(10) | S(10) | V(10) | L(10) | I(10) | S(10) | S(10) | I(10) | I(10) | V(10) | |
| | T(10) | | L(10) | L(10) | T(10) | I(10) | I(10) | L(10) | T(10) | T(10) | L(10) | L(10) | L(10) | |
| | P(10) | | M(10) | M(10) | P(10) | M(10) | V(10) | M(10) | P(10) | P(10) | M(10) | M(10) | M(10) | |
| alanine | A(60) | | A(60) | A(60) | A(60) | A(60) | A(60) | A(60) | A(60) | A(60) | A(60) | A(60) | A(60) | |

Figure 10

| Directed Sequence Polymer design based on a huntingtin peptide - cassette | | | | | | | | | | |
|---|---|---|---|---|---|---|---|---|---|---|
| POSITION | 1 | 2 | 3 | 4 | 5 | 6 | 7 | 8 | 9 | 8 |
| Original | M(8) | A(100) | T(8) | L(8) | E(8) | K(20) | L(8) | M(8) | K(20) | A(100) |
| | L(8) | | S(8) | V(8) | D(8) | | V(8) | L(8) | | |
| | I(8) | | G(8) | I(8) | Q(8) | | I(8) | I(8) | | |
| | V(8) | | P(8) | M(8) | N(8) | | M(8) | V(8) | | |
| alanine | A(68) | | A(68) | A(68) | A(68) | A(80) | A(68) | A(68) | A(80) | |
| | | | | | | | | | | |
| | 11 | 12 | 13 | 14 | 15 | 16 | 17 | | | |
| Original | F(20) | E(8) | S(8) | L(8) | K(20) | S(8) | F(20) | | | |
| | Y(20) | D(8) | T(8) | V(8) | | T(8) | Y(20) | | | |
| | | Q(8) | G(8) | I(8) | | G(8) | | | | |
| | | N(8) | P(8) | M(8) | | P(8) | | | | |
| alanine | A(60) | A(68) | A(68) | A(68) | A(80) | A(68) | A(60) | | | |

SEQUENCE LISTING

<160> NUMBER OF SEQ ID NOS: 19

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

-continued

```
Glu Asn Pro Val Val His Glu Phe Lys Asn Ile Val Thr Pro Arg Thr
1               5                   10                  15
Pro

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Lys Pro Val Val His Leu Phe Ala Asn Ile Val Thr Pro Arg Thr
1               5                   10                  15
Pro

<210> SEQ ID NO 3
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 4
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 5
<211> LENGTH: 40
<212> TYPE: PRT
<213> ORGANISM: Mus sp.

<400> SEQUENCE: 5

Met Gly Lys Gly Glu Glu Gly Tyr Pro Gln Glu Gly Ile Leu Glu Asp
1               5                   10                  15

Met Pro Val Asp Pro Gly Ser Glu Ala Tyr Glu Met Pro Ser Glu Glu
            20                  25                  30

Gly Tyr Gln Asp Tyr Glu Glu Ala
        35                  40

<210> SEQ ID NO 6
```

-continued

```
<211> LENGTH: 17
<212> TYPE: PRT
<213> ORGANISM: Homo sapiens

<400> SEQUENCE: 6

Asp Asn Glu Ala Tyr Glu Met Pro Ser Glu Glu Gly Tyr Gln Asp Tyr
1               5                   10                  15

Glu

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Ala Thr Leu Glu Lys Leu Met Lys Ala Phe Glu Ser Leu Lys Ser
1               5                   10                  15

Phe

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Gln Arg Thr Pro Lys Ile Gln Val Tyr Ser Arg His Pro Ala Glu
1               5                   10                  15

Asn Gly Lys Ser
            20

<210> SEQ ID NO 9
<211> LENGTH: 119
<212> TYPE: PRT
<213> ORGANISM: Homo sapiens

<400> SEQUENCE: 9

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
                20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 10
<211> LENGTH: 253
<212> TYPE: PRT
```

<213> ORGANISM: Homo sapiens

<400> SEQUENCE: 10

```
Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
            115                 120                 125

Val Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Lys Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```

<210> SEQ ID NO 11
<211> LENGTH: 154
<212> TYPE: PRT
<213> ORGANISM: Homo sapiens

<400> SEQUENCE: 11

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110
```

```
Ile Ile Gly Arg Thr Leu Val Val His Glu Lys Ala Asp Asp Leu Gly
            115                 120                 125
Lys Gly Gly Asn Glu Glu Ser Thr Lys Thr Gly Asn Ala Gly Ser Arg
        130                 135                 140
Leu Ala Cys Gly Val Ile Gly Ile Ala Gln
145                 150
```

<210> SEQ ID NO 12
<211> LENGTH: 3144
<212> TYPE: PRT
<213> ORGANISM: Homo sapiens

<400> SEQUENCE: 12

```
Met Ala Thr Leu Glu Lys Leu Met Lys Ala Phe Glu Ser Leu Lys Ser
1               5                   10                  15
Phe Gln Gln Gln Gln Gln Gln Gln Gln Gln Gln Gln Gln Gln Gln Gln
                20                  25                  30
Gln Gln Gln Gln Gln Gln Gln Pro Pro Pro Pro Pro Pro Pro Pro Pro
                35                  40                  45
Pro Pro Pro Gln Leu Pro Gln Pro Pro Gln Ala Gln Pro Leu Leu
50                  55                  60
Pro Gln Pro Gln Pro Pro Pro Pro Pro Pro Pro Pro Pro Gly Pro
65                  70                  75                  80
Ala Val Ala Glu Glu Pro Leu His Arg Pro Lys Lys Glu Leu Ser Ala
                85                  90                  95
Thr Lys Lys Asp Arg Val Asn His Cys Leu Thr Ile Cys Glu Asn Ile
                100                 105                 110
Val Ala Gln Ser Val Arg Asn Ser Pro Glu Phe Gln Lys Leu Leu Gly
                115                 120                 125
Ile Ala Met Glu Leu Phe Leu Leu Cys Ser Asp Asp Ala Glu Ser Asp
                130                 135                 140
Val Arg Met Val Ala Asp Glu Cys Leu Asn Lys Val Ile Lys Ala Leu
145                 150                 155                 160
Met Asp Ser Asn Leu Pro Arg Leu Gln Leu Glu Leu Tyr Lys Glu Ile
                165                 170                 175
Lys Lys Asn Gly Ala Pro Arg Ser Leu Arg Ala Ala Leu Trp Arg Phe
                180                 185                 190
Ala Glu Leu Ala His Leu Val Arg Pro Gln Lys Cys Arg Pro Tyr Leu
                195                 200                 205
Val Asn Leu Leu Pro Cys Leu Thr Arg Thr Ser Lys Arg Pro Glu Glu
                210                 215                 220
Ser Val Gln Glu Thr Leu Ala Ala Ala Val Pro Lys Ile Met Ala Ser
225                 230                 235                 240
Phe Gly Asn Phe Ala Asn Asp Asn Glu Ile Lys Val Leu Leu Lys Ala
                245                 250                 255
Phe Ile Ala Asn Leu Lys Ser Ser Pro Thr Ile Arg Arg Thr Ala
                260                 265                 270
Ala Gly Ser Ala Val Ser Ile Cys Gln His Ser Arg Arg Thr Gln Tyr
                275                 280                 285
Phe Tyr Ser Trp Leu Leu Asn Val Leu Leu Gly Leu Leu Val Pro Val
                290                 295                 300
Glu Asp Glu His Ser Thr Leu Leu Ile Leu Gly Val Leu Leu Thr Leu
305                 310                 315                 320
Arg Tyr Leu Val Pro Leu Leu Gln Gln Gln Val Lys Asp Thr Ser Leu
                325                 330                 335
```

-continued

Lys Gly Ser Phe Gly Val Thr Arg Lys Glu Met Glu Val Ser Pro Ser
            340                 345                 350

Ala Glu Gln Leu Val Gln Val Tyr Glu Leu Thr Leu His His Thr Gln
            355                 360                 365

His Gln Asp His Asn Val Val Thr Gly Ala Leu Glu Leu Leu Gln Gln
370                 375                 380

Leu Phe Arg Thr Pro Pro Glu Leu Leu Gln Thr Leu Thr Ala Val
385                 390                 395                 400

Gly Gly Ile Gly Gln Leu Thr Ala Ala Lys Glu Glu Ser Gly Gly Arg
            405                 410                 415

Ser Arg Ser Gly Ser Ile Val Glu Leu Ile Ala Gly Gly Ser Ser
            420                 425                 430

Cys Ser Pro Val Leu Ser Arg Lys Gln Lys Gly Lys Val Leu Leu Gly
            435                 440                 445

Glu Glu Glu Ala Leu Glu Asp Asp Ser Glu Ser Arg Ser Asp Val Ser
450                 455                 460

Ser Ser Ala Leu Thr Ala Ser Val Lys Asp Glu Ile Ser Gly Glu Leu
465                 470                 475                 480

Ala Ala Ser Ser Gly Val Ser Thr Pro Gly Ser Ala Gly His Asp Ile
            485                 490                 495

Ile Thr Glu Gln Pro Arg Ser Gln His Thr Leu Gln Ala Asp Ser Val
            500                 505                 510

Asp Leu Ala Ser Cys Asp Leu Thr Ser Ser Ala Thr Asp Gly Asp Glu
            515                 520                 525

Glu Asp Ile Leu Ser His Ser Ser Gln Val Ser Ala Val Pro Ser
530                 535                 540

Asp Pro Ala Met Asp Leu Asn Asp Gly Thr Gln Ala Ser Ser Pro Ile
545                 550                 555                 560

Ser Asp Ser Ser Gln Thr Thr Thr Glu Gly Pro Asp Ser Ala Val Thr
            565                 570                 575

Pro Ser Asp Ser Ser Glu Ile Val Leu Asp Gly Thr Asp Asn Gln Tyr
            580                 585                 590

Leu Gly Leu Gln Ile Gly Gln Pro Gln Asp Glu Asp Glu Glu Ala Thr
            595                 600                 605

Gly Ile Leu Pro Asp Glu Ala Ser Glu Ala Phe Arg Asn Ser Ser Met
610                 615                 620

Ala Leu Gln Gln Ala His Leu Leu Lys Asn Met Ser His Cys Arg Gln
625                 630                 635                 640

Pro Ser Asp Ser Ser Val Asp Lys Phe Val Leu Arg Asp Glu Ala Thr
            645                 650                 655

Glu Pro Gly Asp Gln Glu Asn Lys Pro Cys Arg Ile Lys Gly Asp Ile
            660                 665                 670

Gly Gln Ser Thr Asp Asp Ser Ala Pro Leu Val His Cys Val Arg
            675                 680                 685

Leu Leu Ser Ala Ser Phe Leu Leu Thr Gly Gly Lys Asn Val Leu Val
            690                 695                 700

Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
            725                 730                 735

Tyr Lys Val Pro Leu Asp Thr Thr Glu Tyr Pro Glu Glu Gln Tyr Val
            740                 745                 750

Ser Asp Ile Leu Asn Tyr Ile Asp His Gly Asp Pro Gln Val Arg Gly

```
                755                 760                 765
Ala Thr Ala Ile Leu Cys Gly Thr Leu Ile Cys Ser Ile Leu Ser Arg
770                 775                 780

Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
                805                 810                 815

Leu Lys Asp Glu Ser Ser Val Thr Cys Lys Leu Ala Cys Thr Ala Val
                820                 825                 830

Arg Asn Cys Val Met Ser Leu Cys Ser Ser Tyr Ser Glu Leu Gly
                835                 840                 845

Leu Gln Leu Ile Ile Asp Val Leu Thr Leu Arg Asn Ser Ser Tyr Trp
850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
                885                 890                 895

His His Tyr Thr Gly Leu Leu Lys Leu Gln Glu Arg Val Leu Asn Asn
                900                 905                 910

Val Val Ile His Leu Leu Gly Asp Glu Asp Pro Arg Val Arg His Val
                915                 920                 925

Ala Ala Ala Ser Leu Ile Arg Leu Val Pro Lys Leu Phe Tyr Lys Cys
930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Ser His
                965                 970                 975

Phe Ser Val Ser Thr Ile Thr Arg Ile Tyr Arg Gly Tyr Asn Leu Leu
                980                 985                 990

Pro Ser Ile Thr Asp Val Thr Met  Glu Asn Asn Leu Ser  Arg Val Ile
                995                 1000                1005

Ala Ala  Val Ser His Glu Leu  Ile Thr Ser Thr Thr  Arg Ala Leu
     1010                1015                1020

Thr Phe  Gly Cys Cys Glu Ala  Leu Cys Leu Leu Ser  Thr Ala Phe
     1025                1030                1035

Pro Val  Cys Ile Trp Ser Leu  Gly Trp His Cys Gly  Val Pro Pro
     1040                1045                1050

Leu Ser  Ala Ser Asp Glu Ser  Arg Lys Ser Cys Thr  Val Gly Met
     1055                1060                1065

Ala Thr  Met Ile Leu Thr Leu  Leu Ser Ser Ala Trp  Phe Pro Leu
     1070                1075                1080

Asp Leu  Ser Ala His Gln Asp  Ala Leu Ile Leu Ala  Gly Asn Leu
     1085                1090                1095

Leu Ala  Ala Ser Ala Pro Lys  Ser Leu Arg Ser Ser  Trp Ala Ser
     1100                1105                1110

Glu Glu  Glu Ala Asn Pro Ala  Ala Thr Lys Gln Glu  Glu Val Trp
     1115                1120                1125

Pro Ala  Leu Gly Asp Arg Ala  Leu Val Pro Met Val  Glu Gln Leu
     1130                1135                1140

Phe Ser  His Leu Leu Lys Val  Ile Asn Ile Cys Ala  His Val Leu
     1145                1150                1155

Asp Asp  Val Ala Pro Gly Pro  Ala Ile Lys Ala Ala  Leu Pro Ser
     1160                1165                1170
```

```
Leu Thr Asn Pro Pro Ser Leu Ser Pro Ile Arg Arg Lys Gly Lys
1175                1180                1185

Glu Lys Glu Pro Gly Glu Gln Ala Ser Val Pro Leu Ser Pro Lys
1190                1195                1200

Lys Gly Ser Glu Ala Ser Ala Ser Arg Gln Ser Asp Thr Ser
1205                1210                1215

Gly Pro Val Thr Thr Ser Lys Ser Ser Ser Leu Gly Ser Phe Tyr
1220                1225                1230

His Leu Pro Ser Tyr Leu Lys Leu His Asp Val Leu Lys Ala Thr
1235                1240                1245

His Ala Asn Tyr Lys Val Thr Leu Asp Leu Gln Asn Ser Thr Glu
1250                1255                1260

Lys Phe Gly Gly Phe Leu Arg Ser Ala Leu Asp Val Leu Ser Gln
1265                1270                1275

Ile Leu Glu Leu Ala Thr Leu Gln Asp Ile Gly Lys Cys Val Glu
1280                1285                1290

Glu Ile Leu Gly Tyr Leu Lys Ser Cys Phe Ser Arg Glu Pro Met
1295                1300                1305

Met Ala Thr Val Cys Val Gln Gln Leu Leu Lys Thr Leu Phe Gly
1310                1315                1320

Thr Asn Leu Ala Ser Gln Phe Asp Gly Leu Ser Ser Asn Pro Ser
1325                1330                1335

Lys Ser Gln Gly Arg Ala Gln Arg Leu Gly Ser Ser Ser Val Arg
1340                1345                1350

Pro Gly Leu Tyr His Tyr Cys Phe Met Ala Pro Tyr Thr His Phe
1355                1360                1365

Thr Gln Ala Leu Ala Asp Ala Ser Leu Arg Asn Met Val Gln Ala
1370                1375                1380

Glu Gln Glu Asn Asp Thr Ser Gly Trp Phe Asp Val Leu Gln Lys
1385                1390                1395

Val Ser Thr Gln Leu Lys Thr Asn Leu Thr Ser Val Thr Lys Asn
1400                1405                1410

Arg Ala Asp Lys Asn Ala Ile His Asn His Ile Arg Leu Phe Glu
1415                1420                1425

Pro Leu Val Ile Lys Ala Leu Lys Gln Tyr Thr Thr Thr Thr Cys
1430                1435                1440

Val Gln Leu Gln Lys Gln Val Leu Asp Leu Leu Ala Gln Leu Val
1445                1450                1455

Gln Leu Arg Val Asn Tyr Cys Leu Leu Asp Ser Asp Gln Val Phe
1460                1465                1470

Ile Gly Phe Val Leu Lys Gln Phe Glu Tyr Ile Glu Val Gly Gln
1475                1480                1485

Phe Arg Glu Ser Glu Ala Ile Ile Pro Asn Ile Phe Phe Phe Leu
1490                1495                1500

Val Leu Leu Ser Tyr Glu Arg Tyr His Ser Lys Gln Ile Ile Gly
1505                1510                1515

Ile Pro Lys Ile Ile Gln Leu Cys Asp Gly Ile Met Ala Ser Gly
1520                1525                1530

Arg Lys Ala Val Thr His Ala Ile Pro Ala Leu Gln Pro Ile Val
1535                1540                1545

His Asp Leu Phe Val Leu Arg Gly Thr Asn Lys Ala Asp Ala Gly
1550                1555                1560

Lys Glu Leu Glu Thr Gln Lys Glu Val Val Val Ser Met Leu Leu
1565                1570                1575
```

```
Arg Leu Ile Gln Tyr His Gln Val Leu Glu Met Phe Ile Leu Val
    1580            1585                1590

Leu Gln Gln Cys His Lys Glu Asn Glu Asp Lys Trp Lys Arg Leu
    1595            1600                1605

Ser Arg Gln Ile Ala Asp Ile Ile Leu Pro Met Leu Ala Lys Gln
    1610            1615                1620

Gln Met His Ile Asp Ser His Glu Ala Leu Gly Val Leu Asn Thr
    1625            1630                1635

Leu Phe Glu Ile Leu Ala Pro Ser Ser Leu Arg Pro Val Asp Met
    1640            1645                1650

Leu Leu Arg Ser Met Phe Val Thr Pro Asn Thr Met Ala Ser Val
    1655            1660                1665

Ser Thr Val Gln Leu Trp Ile Ser Gly Ile Leu Ala Ile Leu Arg
    1670            1675                1680

Val Leu Ile Ser Gln Ser Thr Glu Asp Ile Val Leu Ser Arg Ile
    1685            1690                1695

Gln Glu Leu Ser Phe Ser Pro Tyr Leu Ile Ser Cys Thr Val Ile
    1700            1705                1710

Asn Arg Leu Arg Asp Gly Asp Ser Thr Ser Thr Leu Glu Glu His
    1715            1720                1725

Ser Glu Gly Lys Gln Ile Lys Asn Leu Pro Glu Glu Thr Phe Ser
    1730            1735                1740

Arg Phe Leu Leu Gln Leu Val Gly Ile Leu Leu Glu Asp Ile Val
    1745            1750                1755

Thr Lys Gln Leu Lys Val Glu Met Ser Glu Gln Gln His Thr Phe
    1760            1765                1770

Tyr Cys Gln Glu Leu Gly Thr Leu Leu Met Cys Leu Ile His Ile
    1775            1780                1785

Phe Lys Ser Gly Met Phe Arg Arg Ile Thr Ala Ala Ala Thr Arg
    1790            1795                1800

Leu Phe Arg Ser Asp Gly Cys Gly Gly Ser Phe Tyr Thr Leu Asp
    1805            1810                1815

Ser Leu Asn Leu Arg Ala Arg Ser Met Ile Thr Thr His Pro Ala
    1820            1825                1830

Leu Val Leu Leu Trp Cys Gln Ile Leu Leu Leu Val Asn His Thr
    1835            1840                1845

Asp Tyr Arg Trp Trp Ala Glu Val Gln Gln Thr Pro Lys Arg His
    1850            1855                1860

Ser Leu Ser Ser Thr Lys Leu Leu Ser Pro Gln Met Ser Gly Glu
    1865            1870                1875

Glu Glu Asp Ser Asp Leu Ala Ala Lys Leu Gly Met Cys Asn Arg
    1880            1885                1890

Glu Ile Val Arg Arg Gly Ala Leu Ile Leu Phe Cys Asp Tyr Val
    1895            1900                1905

Cys Gln Asn Leu His Asp Ser Glu His Leu Thr Trp Leu Ile Val
    1910            1915                1920

Asn His Ile Gln Asp Leu Ile Ser Leu Ser His Glu Pro Pro Val
    1925            1930                1935

Gln Asp Phe Ile Ser Ala Val His Arg Asn Ser Ala Ala Ser Gly
    1940            1945                1950

Leu Phe Ile Gln Ala Ile Gln Ser Arg Cys Glu Asn Leu Ser Thr
    1955            1960                1965

Pro Thr Met Leu Lys Lys Thr Leu Gln Cys Leu Glu Gly Ile His
```

-continued

```
                        1970                1975                1980

Leu Ser Gln Ser Gly Ala Val Leu Thr Leu Tyr Val Asp Arg Leu
    1985                1990                1995

Leu Cys Thr Pro Phe Arg Val Leu Ala Arg Met Val Asp Ile Leu
    2000                2005                2010

Ala Cys Arg Arg Val Glu Met Leu Leu Ala Ala Asn Leu Gln Ser
    2015                2020                2025

Ser Met Ala Gln Leu Pro Met Glu Glu Leu Asn Arg Ile Gln Glu
    2030                2035                2040

Tyr Leu Gln Ser Ser Gly Leu Ala Gln Arg His Gln Arg Leu Tyr
    2045                2050                2055

Ser Leu Leu Asp Arg Phe Arg Leu Ser Thr Met Gln Asp Ser Leu
    2060                2065                2070

Ser Pro Ser Pro Pro Val Ser Ser His Pro Leu Asp Gly Asp Gly
    2075                2080                2085

His Val Ser Leu Glu Thr Val Ser Pro Asp Lys Asp Trp Tyr Val
    2090                2095                2100

His Leu Val Lys Ser Gln Cys Trp Thr Arg Ser Asp Ser Ala Leu
    2105                2110                2115

Leu Glu Gly Ala Glu Leu Val Asn Arg Ile Pro Ala Glu Asp Met
    2120                2125                2130

Asn Ala Phe Met Met Asn Ser Glu Phe Asn Leu Ser Leu Leu Ala
    2135                2140                2145

Pro Cys Leu Ser Leu Gly Met Ser Glu Ile Ser Gly Gly Gln Lys
    2150                2155                2160

Ser Ala Leu Phe Glu Ala Ala Arg Glu Val Thr Leu Ala Arg Val
    2165                2170                2175

Ser Gly Thr Val Gln Gln Leu Pro Ala Val His His Val Phe Gln
    2180                2185                2190

Pro Glu Leu Pro Ala Glu Pro Ala Ala Tyr Trp Ser Lys Leu Asn
    2195                2200                2205

Asp Leu Phe Gly Asp Ala Ala Leu Tyr Gln Ser Leu Pro Thr Leu
    2210                2215                2220

Ala Arg Ala Leu Ala Gln Tyr Leu Val Val Val Ser Lys Leu Pro
    2225                2230                2235

Ser His Leu His Leu Pro Pro Glu Lys Glu Lys Asp Ile Val Lys
    2240                2245                2250

Phe Val Val Ala Thr Leu Glu Ala Leu Ser Trp His Leu Ile His
    2255                2260                2265

Glu Gln Ile Pro Leu Ser Leu Asp Leu Gln Ala Gly Leu Asp Cys
    2270                2275                2280

Cys Cys Leu Ala Leu Gln Leu Pro Gly Leu Trp Ser Val Val Ser
    2285                2290                2295

Ser Thr Glu Phe Val Thr His Ala Cys Ser Leu Ile Tyr Cys Val
    2300                2305                2310

His Phe Ile Leu Glu Ala Val Ala Val Gln Pro Gly Glu Gln Leu
    2315                2320                2325

Leu Ser Pro Glu Arg Arg Thr Asn Thr Pro Lys Ala Ile Ser Glu
    2330                2335                2340

Glu Glu Glu Glu Val Asp Pro Asn Thr Gln Asn Pro Lys Tyr Ile
    2345                2350                2355

Thr Ala Ala Cys Glu Met Val Ala Glu Met Val Glu Ser Leu Gln
    2360                2365                2370
```

```
Ser Val Leu Ala Leu Gly His Lys Arg Asn Ser Gly Val Pro Ala
2375                2380                2385

Phe Leu Thr Pro Leu Leu Arg Asn Ile Ile Ile Ser Leu Ala Arg
2390                2395                2400

Leu Pro Leu Val Asn Ser Tyr Thr Arg Val Pro Pro Leu Val Trp
2405                2410                2415

Lys Leu Gly Trp Ser Pro Lys Pro Gly Gly Asp Phe Gly Thr Ala
2420                2425                2430

Phe Pro Glu Ile Pro Val Glu Phe Leu Gln Glu Lys Glu Val Phe
2435                2440                2445

Lys Glu Phe Ile Tyr Arg Ile Asn Thr Leu Gly Trp Thr Ser Arg
2450                2455                2460

Thr Gln Phe Glu Gly Thr Trp Ala Thr Leu Leu Gly Val Leu Val
2465                2470                2475

Thr Gln Pro Leu Val Met Glu Gln Glu Ser Pro Pro Glu Glu
2480                2485                2490

Asp Thr Glu Arg Thr Gln Ile Asn Val Leu Ala Val Gln Ala Ile
2495                2500                2505

Thr Ser Leu Val Leu Ser Ala Met Thr Val Pro Val Ala Gly Asn
2510                2515                2520

Pro Ala Val Ser Cys Leu Glu Gln Gln Pro Arg Asn Lys Pro Leu
2525                2530                2535

Lys Ala Leu Asp Thr Arg Phe Gly Arg Lys Leu Ser Ile Ile Arg
2540                2545                2550

Gly Ile Val Glu Gln Glu Ile Gln Ala Met Val Ser Lys Arg Glu
2555                2560                2565

Asn Ile Ala Thr His His Leu Tyr Gln Ala Trp Asp Pro Val Pro
2570                2575                2580

Ser Leu Ser Pro Ala Thr Thr Gly Ala Leu Ile Ser His Glu Lys
2585                2590                2595

Leu Leu Leu Gln Ile Asn Pro Glu Arg Glu Leu Gly Ser Met Ser
2600                2605                2610

Tyr Lys Leu Gly Gln Val Ser Ile His Ser Val Trp Leu Gly Asn
2615                2620                2625

Ser Ile Thr Pro Leu Arg Glu Glu Glu Trp Asp Glu Glu Glu Glu
2630                2635                2640

Glu Glu Ala Asp Ala Pro Ala Pro Ser Ser Pro Pro Thr Ser Pro
2645                2650                2655

Val Asn Ser Arg Lys His Arg Ala Gly Val Asp Ile His Ser Cys
2660                2665                2670

Ser Gln Phe Leu Leu Glu Leu Tyr Ser Arg Trp Ile Leu Pro Ser
2675                2680                2685

Ser Ser Ala Arg Arg Thr Pro Ala Ile Leu Ile Ser Glu Val Val
2690                2695                2700

Arg Ser Leu Leu Val Val Ser Asp Leu Phe Thr Glu Arg Asn Gln
2705                2710                2715

Phe Glu Leu Met Tyr Val Thr Leu Thr Glu Leu Arg Arg Val His
2720                2725                2730

Pro Ser Glu Asp Glu Ile Leu Ala Gln Tyr Leu Val Pro Ala Thr
2735                2740                2745

Cys Lys Ala Ala Ala Val Leu Gly Met Asp Lys Ala Val Ala Glu
2750                2755                2760

Pro Val Ser Arg Leu Leu Glu Ser Thr Leu Arg Ser Ser His Leu
2765                2770                2775
```

Pro Ser Arg Val Gly Ala Leu His Gly Val Leu Tyr Val Leu Glu
    2780            2785                2790

Cys Asp Leu Leu Asp Asp Thr Ala Lys Gln Leu Ile Pro Val Ile
    2795            2800                2805

Ser Asp Tyr Leu Leu Ser Asn Leu Lys Gly Ile Ala His Cys Val
    2810            2815                2820

Asn Ile His Ser Gln Gln His Val Leu Val Met Cys Ala Thr Ala
    2825            2830                2835

Phe Tyr Leu Ile Glu Asn Tyr Pro Leu Asp Val Gly Pro Glu Phe
    2840            2845                2850

Ser Ala Ser Ile Ile Gln Met Cys Gly Val Met Leu Ser Gly Ser
    2855            2860                2865

Glu Glu Ser Thr Pro Ser Ile Ile Tyr His Cys Ala Leu Arg Gly
    2870            2875                2880

Leu Glu Arg Leu Leu Leu Ser Glu Gln Leu Ser Arg Leu Asp Ala
    2885            2890                2895

Glu Ser Leu Val Lys Leu Ser Val Asp Arg Val Asn Val His Ser
    2900            2905                2910

Pro His Arg Ala Met Ala Ala Leu Gly Leu Met Leu Thr Cys Met
    2915            2920                2925

Tyr Thr Gly Lys Glu Lys Val Ser Pro Gly Arg Thr Ser Asp Pro
    2930            2935                2940

Asn Pro Ala Ala Pro Asp Ser Glu Ser Val Ile Val Ala Met Glu
    2945            2950                2955

Arg Val Ser Val Leu Phe Asp Arg Ile Arg Lys Gly Phe Pro Cys
    2960            2965                2970

Glu Ala Arg Val Val Ala Arg Ile Leu Pro Gln Phe Leu Asp Asp
    2975            2980                2985

Phe Phe Pro Pro Gln Asp Ile Met Asn Lys Val Ile Gly Glu Phe
    2990            2995                3000

Leu Ser Asn Gln Gln Pro Tyr Pro Gln Phe Met Ala Thr Val Val
    3005            3010                3015

Tyr Lys Val Phe Gln Thr Leu His Ser Thr Gly Gln Ser Ser Met
    3020            3025                3030

Val Arg Asp Trp Val Met Leu Ser Leu Ser Asn Phe Thr Gln Arg
    3035            3040                3045

Ala Pro Val Ala Met Ala Thr Trp Ser Leu Ser Cys Phe Phe Val
    3050            3055                3060

Ser Ala Ser Thr Ser Pro Trp Val Ala Ala Ile Leu Pro His Val
    3065            3070                3075

Ile Ser Arg Met Gly Lys Leu Glu Gln Val Asp Val Asn Leu Phe
    3080            3085                3090

Cys Leu Val Ala Thr Asp Phe Tyr Arg His Gln Ile Glu Glu Glu
    3095            3100                3105

Leu Asp Arg Arg Ala Phe Gln Ser Val Leu Glu Val Val Ala Ala
    3110            3115                3120

Pro Gly Ser Pro Tyr His Arg Leu Leu Thr Cys Leu Arg Asn Val
    3125            3130                3135

His Lys Val Thr Thr Cys
    3140

<210> SEQ ID NO 13
<211> LENGTH: 140
<212> TYPE: PRT

```
<213> ORGANISM: Mus musculus

<400> SEQUENCE: 13

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Gly Lys
            20                  25                  30

Thr Lys Glu Gly Val Leu Tyr Val Gly Ser Lys Thr Lys Glu Gly Val
        35                  40                  45

Val His Gly Val Thr Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Asn Ile Ala Ala Ala Thr Gly Phe Val Lys
                85                  90                  95

Lys Asp Gln Met Gly Lys Gly Glu Glu Gly Tyr Pro Gln Glu Gly Ile
                100                 105                 110

Leu Glu Asp Met Pro Val Asp Pro Gly Ser Glu Ala Tyr Glu Met Pro
            115                 120                 125

Ser Glu Glu Gly Tyr Gln Asp Tyr Glu Pro Glu Ala
        130                 135                 140

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Lys Ala Val Ala Ala Trp Thr Leu Lys Ala Ala Ala
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr His Met Cys Glu
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Trp Lys Asn Ala
1               5

<210> SEQ ID NO 17
<211> LENGTH: 57
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<221> NAME/KEY: MOD_RES
<222> LOCATION: (5)..(5)
<223> OTHER INFORMATION: Thr, Ser, Gly, Pro or Ala
<220> FEATURE:
<221> NAME/KEY: MOD_RES
<222> LOCATION: (6)..(6)
<223> OTHER INFORMATION: His, Arg or Ala
<220> FEATURE:
<221> NAME/KEY: MOD_RES
<222> LOCATION: (7)..(7)
<223> OTHER INFORMATION: Met, Val, Ile or Ala
<220> FEATURE:
<221> NAME/KEY: MOD_RES
<222> LOCATION: (8)..(8)
<223> OTHER INFORMATION: Cys or Ala
<220> FEATURE:
<221> NAME/KEY: MOD_RES
<222> LOCATION: (9)..(9)
<223> OTHER INFORMATION: Glu, Asp, Gln, Asn or Ala
<220> FEATURE:
<221> NAME/KEY: MOD_RES
<222> LOCATION: (10)..(10)
<223> OTHER INFORMATION: Thr, Ser, Gly, Pro or Ala
<220> FEATURE:
<221> NAME/KEY: MOD_RES
<222> LOCATION: (11)..(11)
<223> OTHER INFORMATION: His, Arg or Ala
<220> FEATURE:
<221> NAME/KEY: MOD_RES
<222> LOCATION: (12)..(12)
<223> OTHER INFORMATION: Met, Val, Ile or Ala
<220> FEATURE:
<221> NAME/KEY: MOD_RES
<222> LOCATION: (13)..(13)
<223> OTHER INFORMATION: Cys or Ala
<220> FEATURE:
<221> NAME/KEY: MOD_RES
<222> LOCATION: (14)..(14)
<223> OTHER INFORMATION: Glu, Asp, Gln, Asn or Ala
<220> FEATURE:
<221> NAME/KEY: MOD_RES
<222> LOCATION: (15)..(15)
<223> OTHER INFORMATION: Pro, Thr, Ser, Gly or Ala
<220> FEATURE:
<221> NAME/KEY: MOD_RES
<222> LOCATION: (16)..(16)
<223> OTHER INFORMATION: Trp or Ala
<220> FEATURE:
<221> NAME/KEY: MOD_RES
<222> LOCATION: (17)..(17)
<223> OTHER INFORMATION: Lys or Ala
<220> FEATURE:
<221> NAME/KEY: MOD_RES
<222> LOCATION: (18)..(18)
<223> OTHER INFORMATION: Asn, Gln or Ala
<220> FEATURE:
<221> NAME/KEY: MOD_RES
<222> LOCATION: (20)..(20)
<223> OTHER INFORMATION: Pro, Thr, Ser, Gly or Ala
<220> FEATURE:
<221> NAME/KEY: MOD_RES
<222> LOCATION: (21)..(21)
<223> OTHER INFORMATION: Trp or Ala
<220> FEATURE:
<221> NAME/KEY: MOD_RES
<222> LOCATION: (22)..(22)
<223> OTHER INFORMATION: Lys or Ala
<220> FEATURE:
<221> NAME/KEY: MOD_RES
<222> LOCATION: (23)..(23)
<223> OTHER INFORMATION: Asn, Gln or Ala
<220> FEATURE:
<221> NAME/KEY: MOD_RES
<222> LOCATION: (25)..(25)
<223> OTHER INFORMATION: Thr, Ser, Gly, Pro or Ala
<220> FEATURE:
<221> NAME/KEY: MOD_RES
<222> LOCATION: (26)..(26)
```

```
<223> OTHER INFORMATION: His, Arg or Ala
<220> FEATURE:
<221> NAME/KEY: MOD_RES
<222> LOCATION: (27)..(27)
<223> OTHER INFORMATION: Met, Val, Ile or Ala
<220> FEATURE:
<221> NAME/KEY: MOD_RES
<222> LOCATION: (28)..(28)
<223> OTHER INFORMATION: Cys or Ala
<220> FEATURE:
<221> NAME/KEY: MOD_RES
<222> LOCATION: (29)..(29)
<223> OTHER INFORMATION: Glu, Asp, Gln, Asn or Ala
<220> FEATURE:
<221> NAME/KEY: MOD_RES
<222> LOCATION: (30)..(30)
<223> OTHER INFORMATION: Thr, Ser, Gly, Pro or Ala
<220> FEATURE:
<221> NAME/KEY: MOD_RES
<222> LOCATION: (31)..(31)
<223> OTHER INFORMATION: His, Arg or Ala
<220> FEATURE:
<221> NAME/KEY: MOD_RES
<222> LOCATION: (32)..(32)
<223> OTHER INFORMATION: Met, Val, Ile or Ala
<220> FEATURE:
<221> NAME/KEY: MOD_RES
<222> LOCATION: (33)..(33)
<223> OTHER INFORMATION: Cys or Ala
<220> FEATURE:
<221> NAME/KEY: MOD_RES
<222> LOCATION: (34)..(34)
<223> OTHER INFORMATION: Glu, Asp, Gln, Asn or Ala
<220> FEATURE:
<221> NAME/KEY: MOD_RES
<222> LOCATION: (35)..(35)
<223> OTHER INFORMATION: Pro, Thr, Ser, Gly or Ala
<220> FEATURE:
<221> NAME/KEY: MOD_RES
<222> LOCATION: (36)..(36)
<223> OTHER INFORMATION: Trp or Ala
<220> FEATURE:
<221> NAME/KEY: MOD_RES
<222> LOCATION: (37)..(37)
<223> OTHER INFORMATION: Lys or Ala
<220> FEATURE:
<221> NAME/KEY: MOD_RES
<222> LOCATION: (38)..(38)
<223> OTHER INFORMATION: Asn, Gln or Ala
<220> FEATURE:
<221> NAME/KEY: MOD_RES
<222> LOCATION: (40)..(40)
<223> OTHER INFORMATION: Pro, Thr, Ser, Gly or Ala
<220> FEATURE:
<221> NAME/KEY: MOD_RES
<222> LOCATION: (41)..(41)
<223> OTHER INFORMATION: Trp or Ala
<220> FEATURE:
<221> NAME/KEY: MOD_RES
<222> LOCATION: (42)..(42)
<223> OTHER INFORMATION: Lys or Ala
<220> FEATURE:
<221> NAME/KEY: MOD_RES
<222> LOCATION: (43)..(43)
<223> OTHER INFORMATION: Asn, Gln or Ala
<220> FEATURE:
<223> OTHER INFORMATION: see specification as filed for detailed
      description of substitutions and preferred embodiments

<400> SEQUENCE: 17

Arg Gly Asp Ser Xaa Xaa Xaa Xaa Xaa Xaa Xaa Xaa Xaa Xaa Xaa
1               5                   10                  15

Xaa Xaa Ala Xaa Xaa Xaa Xaa Ala Xaa Xaa Xaa Xaa Xaa Xaa Xaa
            20                  25                  30

Xaa Xaa Xaa Xaa Xaa Xaa Ala Xaa Xaa Xaa Xaa Ala Ala Lys Ala Val
        35                  40                  45
```

```
Ala Ala Trp Thr Leu Lys Ala Ala Ala
     50                  55

<210> SEQ ID NO 18
<211> LENGTH: 51
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Asn Glu Ala Tyr Glu Met Pro Ser Glu Glu Gly Tyr Gln Asp Tyr
1               5                   10                  15

Glu Asp Asn Glu Ala Tyr Glu Met Pro Ser Glu Glu Gly Tyr Gln Asp
            20                  25                  30

Tyr Glu Asp Asn Glu Ala Tyr Glu Met Pro Ser Glu Glu Gly Tyr Gln
        35                  40                  45

Asp Tyr Glu
    50

<210> SEQ ID NO 19
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Asp, Glu, Gln, Asn or Ala
<220> FEATURE:
<221> NAME/KEY: MOD_RES
<222> LOCATION: (3)..(3)
<223> OTHER INFORMATION: Glu, Asp, Gln, Asn or Ala
<220> FEATURE:
<221> NAME/KEY: MOD_RES
<222> LOCATION: (4)..(4)
<223> OTHER INFORMATION: Phe, Tyr or Ala
<220> FEATURE:
<221> NAME/KEY: MOD_RES
<222> LOCATION: (5)..(5)
<223> OTHER INFORMATION: Arg, His or Ala
<220> FEATURE:
<221> NAME/KEY: MOD_RES
<222> LOCATION: (6)..(6)
<223> OTHER INFORMATION: His, Arg or Ala
<220> FEATURE:
<221> NAME/KEY: MOD_RES
<222> LOCATION: (7)..(7)
<223> OTHER INFORMATION: Asp, Glu, Gln, Asn or Ala
<220> FEATURE:
<221> NAME/KEY: MOD_RES
<222> LOCATION: (8)..(9)
<223> OTHER INFORMATION: Ser, Thr, Gly, Pro or Ala
<220> FEATURE:
<221> NAME/KEY: MOD_RES
<222> LOCATION: (10)..(10)
<223> OTHER INFORMATION: Tyr, Phe or Ala
<220> FEATURE:
<221> NAME/KEY: MOD_RES
<222> LOCATION: (11)..(11)
<223> OTHER INFORMATION: Glu, Asp, Gln, Asn or Ala
<220> FEATURE:
<221> NAME/KEY: MOD_RES
<222> LOCATION: (12)..(12)
<223> OTHER INFORMATION: Val, Ile, Leu, Met or Ala
<220> FEATURE:
<221> NAME/KEY: MOD_RES
<222> LOCATION: (13)..(14)
<223> OTHER INFORMATION: His, Arg or Ala
<220> FEATURE:
<221> NAME/KEY: MOD_RES
```

```
<222> LOCATION: (15)..(15)
<223> OTHER INFORMATION: Gln, Glu, Asp, Asn or Ala
<220> FEATURE:
<221> NAME/KEY: MOD_RES
<222> LOCATION: (16)..(16)
<223> OTHER INFORMATION: Lys or Ala
<220> FEATURE:
<221> NAME/KEY: MOD_RES
<222> LOCATION: (17)..(18)
<223> OTHER INFORMATION: Leu, Val, Ile, Met or Ala
<220> FEATURE:
<221> NAME/KEY: MOD_RES
<222> LOCATION: (19)..(20)
<223> OTHER INFORMATION: Phe, Tyr or Ala
<220> FEATURE:
<221> NAME/KEY: MOD_RES
<222> LOCATION: (22)..(23)
<223> OTHER INFORMATION: Glu, Asp, Gln, Asn or Ala
<220> FEATURE:
<221> NAME/KEY: MOD_RES
<222> LOCATION: (24)..(24)
<223> OTHER INFORMATION: Val, Ile, Leu, Met or Ala
<220> FEATURE:
<221> NAME/KEY: MOD_RES
<222> LOCATION: (25)..(26)
<223> OTHER INFORMATION: Glu, Ser, Thr, Pro or Ala
<220> FEATURE:
<221> NAME/KEY: MOD_RES
<222> LOCATION: (27)..(27)
<223> OTHER INFORMATION: Asn, Glu, Asp, Gln or Ala
<220> FEATURE:
<221> NAME/KEY: MOD_RES
<222> LOCATION: (28)..(28)
<223> OTHER INFORMATION: Lys or Ala
<220> FEATURE:
<221> NAME/KEY: MOD_RES
<222> LOCATION: (29)..(29)
<223> OTHER INFORMATION: Gly, Ser, Thr, Pro or Ala
<220> FEATURE:
<221> NAME/KEY: MOD_RES
<222> LOCATION: (31)..(32)
<223> OTHER INFORMATION: Ile, Val, Leu, Met or Ala
<220> FEATURE:
<221> NAME/KEY: MOD_RES
<222> LOCATION: (33)..(33)
<223> OTHER INFORMATION: Gly, Ser, Thr, Pro or Ala
<220> FEATURE:
<221> NAME/KEY: MOD_RES
<222> LOCATION: (34)..(35)
<223> OTHER INFORMATION: Leu, Val, Ile, Met or Ala
<220> FEATURE:
<221> NAME/KEY: MOD_RES
<222> LOCATION: (36)..(36)
<223> OTHER INFORMATION: Val, Ile, Leu, Met or Ala
<220> FEATURE:
<221> NAME/KEY: MOD_RES
<222> LOCATION: (37)..(38)
<223> OTHER INFORMATION: Gly, Ser, Thr, Pro or Ala
<220> FEATURE:
<221> NAME/KEY: MOD_RES
<222> LOCATION: (39)..(41)
<223> OTHER INFORMATION: Val, Ile, Leu, Met or Ala
<220> FEATURE:
<223> OTHER INFORMATION: see specification as filed for detailed
     description of substitutions and preferred embodiments

<400> SEQUENCE: 19

Xaa Ala Xaa Xaa Xaa Xaa Xaa Xaa Xaa Xaa Xaa Xaa Xaa Xaa Xaa Xaa
1               5                   10                  15

Xaa Xaa Xaa Xaa Ala Xaa Xaa Xaa Xaa Xaa Xaa Xaa Xaa Ala Xaa Xaa
            20                  25                  30

Xaa Xaa Xaa Xaa Xaa Xaa Xaa Xaa Xaa Ala
        35                  40
```

| | | | | | | | | | | |

SYNTHESIS OF DIRECTED SEQUENCE POLYMER COMPOSITIONS AND ANTIBODIES THEREOF FOR THE TREATMENT OF PROTEIN CONFORMATIONAL DISORDERS

RELATED APPLICATIONS

This application claims the benefit of U.S. Provisional Application No. 61/168,555, filed Apr. 10, 2009, and U.S. Provisional Application No. 61/124,689, filed Apr. 17, 2008, the specifications of which are hereby incorporated herein by reference in their entirety.

FIELD OF INVENTION

This application provides methods of making improved compositions comprising certain mixtures of peptides, which mixtures may be synthesized as a single manufactured entity and designed based on disease-related polypeptides, and compositions comprising antibodies against such mixtures for the prophylactic and/or therapeutic treatment of protein conformational disorders.

BACKGROUND OF THE INVENTION

Protein Conformational Disorder

It has been recognized in the recent years that there is a class of diseases and disorders that correlates with the presence of aggregates, whether intra- or extra-cellular, of misfolded or conformationally altered proteins. These proteins exist in a non-diseased environment. In a disease state, however, through certain alterations in the conformation, they adopt a secondary/tertiary structure different from those in the non-diseased state. The amino acid sequence is often unaltered. The misfolded proteins tend to self-associate, aggregating in an ordered fashion, form toxic precipitates, and deposit into tissues. The aggregated protein often takes a fibrillar appearance.

Examples of these disorders, now known as "protein conformational disorders" (PCDs), include but are not limited to Alzheimer's disease (AD), Parkinson disease (PD), Type-2 diabetes, amyotrophic lateral sclerosis (ALS), dialysis-related amyloidosis (DRA), reactive amylosis, cystic fibrosis (CF), sickle cell anemia, Huntington's disease (HD), Creutzfeldt-Jakob disease (CJD) and related disorders, and systemic and cerebral hereditary amyloidosis. Examples of globular proteins that undergo fibrillogenesis include transthyretin, beta 2 microglobulin, serum amyloid A protein, Ig light chains, insulin, human lysozyme, alpha lactalbumin, and monellin. Examples of natively unfolded proteins that undergo fibrillogenesis include amyloid beta protein, tau protein, alpha-synuclein, amylin, and prothymosin alpha.

Pathogenesis and Biochemical Progression of PCD

Investigators have correlated protein aggregate deposition with the degeneration of tissue. Although there remains controversy with regard to the "cause or effect" of the presence of aggregate and the manifestation of the disease pathology, evidence is accumulating that the pathology is caused by aggregates, perhaps by direct toxicity due to the aggregation or by a loss of biological function of the misfolded protein.

The formation of aggregates is referred to as "fibrillogenesis." Before the start of fibrillogenesis, the protein relevant to PCD pathology is in a naturally folded conformation and in monomeric or defined oligomeric forms, each peptide comprising a mixture of alpha-helices, some beta-sheets, and random coils. By the end of fibrillogenesis, the protein is aggregated, and the peptide has adopted an altered conformation, i.e. mostly a beta-pleated sheet conformation. The conformational changes of the peptides and aggregation appear to coincide, but the cause and effect of conformational change and aggregation, and the sequence of events, remain to be elucidated.

When considering the pathogenesis of a PCD, it has been proposed that the fibrillogenesis is a crystallization-like process: after a "seed" of oligomers forms, an aggregate grows over time through self-association. The protein may take an altered conformation because the aggregate exists and serves as a template, or it may take the altered conformation because of other factors, but once in that conformation, easily participates in fibrillogenesis. In contrast, another proposal hypothesizes that the conformational alterations alone may not cause or promote aggregation, and there is a factor that induces the aggregation. Such underlying factors that promote or induce structural changes in the protein include inflammatory or oxidative environments, nitration, phosphorylation, pH, or metal ion exposure (high concentrations of copper ions can induce the oligomerization of β2 microglobulin monomers, which in turn leads to fibril formation (Eakin et al., Biochemistry 2004, 43, 7808-7815)).

Various treatment modes and possible therapeutic agents for PCDs are currently being investigated. Whether conformational change precedes the start of the fibrillogenesis or vice versa will influence the effectiveness of a treatment strategy. For example, a treatment mode with an assumption that fibrillogenesis is caused by the beta-sheet conformation will attempt to inhibit the beta-sheet formation. In contrast, if the assumption was that aggregation promotes further formation of proteins with a degenerative conformation, a treatment mode may aim to inhibit aggregation by various means. An illustration of the former approach includes an attempt to inhibit the formation of, or to break, beta-sheets, using peptides. Such peptides are designed from the sequences of areas of proteins most likely involved in the process of nucleation and aggregation, such as the hydrophic core of amyloid-beta, a peptide intimately involved in the pathology of Alzheimer's disease. An illustration of the latter approach is an attempt to manipulate protein conformation and prohibit nucleation and subsequent formation of amyloids, or, "amyloidogenesis," by creating mini-chaperone peptides from outside of the beta-sheet regions.

Another promising approach, regardless of the mechanism of aggregate formation, is to focus on the aggregates themselves. There have been attempts to reduce the level of aggregated protein of interest by antibodies: given sufficient specificity and ability to promote clearance, an antibody has a potential to be an effective therapeutic. To overcome delivery challenges, attempts have been made to express such antibodies intracellularly from a delivered gene. However, despite its potential, currently, the existing antibody therapeutics, if any, do not sufficiently prevent, improve, or even slow progression of the pathology, and there remains largely unmet needs for an effective treatment for a PCD.

Strategy for Creating Synthetic Therapeutic Peptides

The development and exploitation of combinatorial chemistry (CC) has propelled drug discovery. Drug discovery can be generalized into two major steps, lead generation and lead optimization. Oftentimes, a lead compound is identified that has some of the desired characteristics of a commercially viable therapeutic, but has shortcomings such as a low specific activity, toxicity, instability, etc. Thus, once a lead is identified, practitioners attempt to optimize the lead compound by testing other related compounds with similar structures. CC allows practitioners to create and quickly screen a library made of a vast number of candidates, to identify those with a specific activity against a target of interest.

For peptide based drugs, the goal is to define a single, or a limited set of peptides which demonstrate a particular activity. The art of CC as applied to the synthesis of peptide libraries, too, has advanced, producing highly reliable and pure mixtures of peptides of great diversity. The process of identifying the single or limited set of peptides that were responsible for the observed activity from such diverse libraries, called deconvolution, is schematically represented in FIG. 1A.

An analogous process applies for development of a therapeutically effective antibody. Traditionally, antibodies were raised by immunizing an animal using a target protein or peptide as an antigen, either directly collecting sera for polyclonal antibodies (i.e. a mixture of antibodies enriched for those that bind to the target) or by creating hybridomas and selecting those hybridomas that produce monoclonal antibodies that bind to the target. In more recent years, phage display libraries have been used to present a large number of antibodies, from which antibodies that bind to the target is selected. In other words, antibody isolation is an initial screening of a lead molecule from a large number of candidates.

It is well known in the art, however, that an antibody that binds to the target is not necessarily one that has a desired therapeutic effect. As such, therapeutically effective antibodies may still have to be created through the process of lead optimization. The optimization may take a form of further screening of an antibody library (e.g. a phage display library), direct manipulation of complementarity determining regions of an immunoglobulin, or renewed immunization of an animal using related but different epitopes in an attempt to create a further variety in the enriched antibodies that the animal produces.

Low Immunogenicity, or Necessity for Highly Specific Antibodies

In PCD, for therapeutic, prophylactic, and diagnostic purposes, the antibodies that are desirable recognize and specifically bind to proteins of certain altered conformation. The difficulty lies in the fact that these proteins exist as normal parts of the patient's system, were it not for the altered conformation that they are in. Thus, even though these proteins are pathological, they may not elicit strong natural immune responses in the afflicted individuals, and it may be difficult to elicit an immune response (thus to raise antibodies) using the native sequence of the target protein in other subjects of the same species, or in an individual with similar immunological profile, which is often desirable due to the lower probability of adverse immunological reaction.

Another challenge is that the antibody should differentiate between the same protein in a non-pathological conformation and in a pathological conformation. A protein relevant to a PCD may have the same primary structure, whether in a non-pathological condition or in pathological condition. Without the ability to distinguish, the antibody intended for therapeutic purposes may adversely affect the patient by eliminating or interfering with the normal, functioning protein. Thus, a high specificity towards the particular conformation, or series of alterations, is required.

Although immunization with an immunogen having a single epitope may induce multiple antibodies having complementarity determining regions (CDR) different from each other, it may be difficult to strongly elicit (and thus detect and identify) all varieties of antibodies. In addition, even if antibodies are induced, the most easily inducible and detectable antibodies against such epitope may not include those antibodies with a high specificity towards the particular pathological conformation as described in the preceding paragraphs. In an attempt to overcome these challenges, investigators have designed peptides with sequences similar to the target peptides. These variations of the target peptides may induce generation of antibodies that are different from those induced by the target peptides, but may cross-react sufficiently with the target peptides. Thus, these related peptides may be desirable and/or required to identify an antibody that may not be induced by an epitope of the original sequence.

One such approach is the creation of altered peptide ligands (APL). This approach is schematically represented in FIG. 1B. An APL is defined as an analog peptide which contains a small number of amino acid changes from a starting sequence such as that of a native immunogenic peptide ligand. An illustrative example is an APL based on an epitope of myelin basic protein, MBP83-99 (ENPVVHEFKNIVTPRTP) (SEQ ID NO: 1), which is reported to be a target of autoimmune response causing multiple sclerosis. APLs were made by replacing the bold and underlined amino acid residues "E", "N", "E" and "K," with various other amino acid residues. Screening for peptides that appeared to have the desired activity of neutralizing antibodies against MBP83-99 yielded a single peptide having the amino acid residue sequence AKPVVHLFANIVTPRTP (SEQ ID NO: 2), Kim et al. Clinical Immunology, 2002, 104:105-114. The peptide was placed into limited human trials, which reportedly resulted in the long term immune reactivity against the peptide, but the treatment has been deemed clinically ineffective by evaluation using MRI. Thus this APL, as with many antibody-based therapeutic candidates, had limited effectiveness in terms of clinical efficacy.

Further complicating the application of the technology, an APL that may induce an antagonist-like reaction, may also induce a partial agonist response, or induce a state of anergy in the reactive T cell population. See, for example, Fairchild et al., Curr. Topics Peptide Protein Res. 2004, 6:237-44, who, in discussing APL in the context of allograft rejection therapy, note that an APL acting as an antagonist for one TCR, may become an agonist for another.

The approach using APL, along with other approaches currently known in the art, to identify therapeutic peptides, while recognizing the advantage of variations in the therapeutic peptide compositions, derive from the concept that there is one or more defined peptide sequence evoking a defined immunological response. These strategies have attempted to multiply and diversify modulatory peptides via the introduction of defined, single changes performed one at a time.

An entirely different approach which has evolved alongside the defined sequence peptide immunotherapy approach is the use of limited amino acid diversity, random epitope polymers. Random sequence polymers (RSP) can be described as a random order mixture of amino acid copolymers comprising two or more amino acid residues in various ratios, forming copolymers by random sequence bonding, preferably through peptide bonds, of these amino acid residues, which mixture is useful for invoking or attenuating certain immunological reactions when administered to a mammal. Because of the extensive diversity of the sequence mixture, a large number of therapeutically effective peptide sequences are likely included in the mixture. In addition, because of the additional peptides which may at any given time not be therapeutically effective, but may emerge as effective as the epitope shifting and spreading occurs, the therapeutic composition may remain effective over a time of dosing regimen. This approach is schematically represented in FIG. 1D.

Copolymer-1 (also known as Copaxone, glatiramer acetate, COP-1, or YEAK random copolymer), is used for the treatment of multiple sclerosis. Random copolymers are described in International PCT Publication Nos. WO 00/05250, WO 00/05249; WO 02/59143, WO 0027417, WO 96/32119, WO/2005/085323, in U.S. Patent Publication Nos. 2004/003888, 2002/005546, 2003/0004099, 2003/0064915 and 2002/0037848, in U.S. Pat. Nos. 6,514,938, 5,800,808 and 5,858,964. Copolymer-1 has been used in combination with a mucosal adjuvant and an A beta peptide for the development of an Alzheimer's vaccine (Frenkel, Dan et al., 2005, *J Clin Invest.*, 115:2423), and has been described as a constituent in a method of vaccination designed to regenerate neuronal tissue (U.S. Pat. No. 6,844,314).

Tracing back steps to the defined peptide search, there have also been attempts to identify the active peptide(s) within the RSP mixture. The drawback of this technology lies in the very nature of the attempt to determine discrete substitutes for the randomness that COP-1 encompasses.

Effective as the random sequence polymer approach may be, even the improvements have not resolved the drawback and limitation of COP-1, which is, for example, the undefined nature of what is effective in each motif and the possibility of containing a large proportion of truly inactive peptides, lowering the concentration of the active components, or worse, adversely stimulating the immune system. Additionally, these compounds are difficult to manufacture and to obtain consistency from lot-to-lot.

Despite the modest success of the existing approaches, need remains for a composition and a method to create such composition that would serve effectively as a vaccine and immunogen by eliciting beneficial immune responses consistently and over time toward pathological proteins or peptides related to a PCD, for which existing vaccine compositions have failed to be effective.

SUMMARY OF THE INVENTION

The instant invention comprises a process for the solid phase synthesis of directed epitope peptide mixtures useful in modulation of the immune system in the treatment of a protein conformational disorder, and the composition prepared by such process. The instant invention also comprises a process for producing antibodies that are therapeutically or prophylactically useful in treatment of protein conformational disorders, useful for use as research reagents, or useful as diagnostic tools for such disorders, by eliciting immune responses using a composition comprising directed epitope peptide mixtures, and the antibodies thus produced. An aspect of the invention is a method of prophylactic or therapeutic treatment for protein conformational disorders by administering the DSP composition of the present invention or by administering an antibody produced by the process of the present invention using a DSP composition. Another aspect is a method of diagnosis of a protein conformational disorder.

An aspect of the present invention is a process for manufacturing a composition comprising directed-sequence polymers (DSPs), and the further aspect of the present invention is a composition thus manufactured.

An embodiment of the invention is a process comprising the steps of: (1) selecting a first base peptide sequence, wherein the sequence is an amino acid sequence of an epitope of an antigen associated with a protein conformational disorder; (2) synthesizing by solid phase peptide synthesis a first cassette of the DSPs according to a rule described below and particular input amino acid ratios; and (3) extending the length of the DSPs by repeating step (2) for 1 to 15 cycles, either under the same condition every cycle or using a different input ratio of amino acids in the mixture; or repeating steps (1) and (2) for 1 to 15 cycles and elongating the DSP using cassettes based on more than one base peptide; or assembling 1 to 15 cassettes synthesized in a single cycle of step (2), either all under the same condition in step (2) or in different conditions.

In the embodiment above, the cassette of the DSP is synthesized with one of several amino acids in each amino acid position. The amino acid to be incorporated to a particular position is randomly selected from (i) the original amino acid in that position; (ii) a replacement defined according to amino acid similarity shown in the similarity table of FIG. 4 or selected from amino acids found as naturally occurring variations in a corresponding position in a protein having the same or substantially the same physiological role and/or activity as the antigen; and (iii) alanine.

The length of a DSP can be one of the original defined sequence peptide or 30 lengths of the original defined sequence peptide. The length of the combined sequence can be between about 10 and about 300 amino acids.

The percentage of alanine as compared to all of the other amino acids in the DSP combined is greater than 10%, and does not exceed 90%. In one embodiment, the alanine percentage is between 10% and 70%. In another embodiment, the alanine percentage is between 15% and 50%.

Thus, in one embodiment, the composition comprises DSP having a length of between about 10 to 300 amino acids, wherein each of such DSPs comprises between 1-15 cassettes, each block comprising between 8-100 amino acids; each cassette is derived from a base peptide sequence of an epitope of an antigen associated with a protein conformation disorder, and the amino acid residue of each amino acid position is selected from (i) the original amino acid in that position; (ii) a replacement defined according to amino acid similarity shown in the similarity table of FIG. 4 or selected from amino acids found as naturally occurring variations in a corresponding position in a protein having the same or substantially the same physiological role and/or activity as the antigen; and (iii) alanine. The molar ratio of alanine in the composition of the invention is greater than 10%, and does not exceed 90%. In one embodiment, the alanine percentage is between 10% and 70%. In another embodiment the alanine percentage is between 15% and 50%.

The complexity of the peptide mixture manufactured according to the process of the invention is greater than $5\times10^2$ different peptides. Preferably the complexity of the mixture is greater than $1\times10^4$ different peptides. More preferably the complexity of the mixture is greater than $1\times10^6$ different peptides.

In some embodiments, the base peptide sequence used for the process to manufacture the DSP composition is an epitope relevant to the pathology of protein conformational disorders affecting the central and/or peripheral nervous system, selected from the group consisting of: Alzheimer's disease (AD), Dutch hereditary cerebral hemorrhage with amyloidosis (a.k.a cerebrovascular amyloidosis), congophilic angiopathy; Pick's disease, progressive supranuclear palsy; familial British dementia; Parkinson's disease (PD), Lewy-body related diseases, multiple system atrophy, Hallervorden-Spatz disease; amyotrophic lateral sclerosis (ALS); Huntington's disease (HD); spinocerebellar ataxia; neuronal intranuclear inclusion disease; hereditary dentatorubral-pallidoluysian atrophy; prion-related diseases such as scrapie, bovine spongiform encephalopathy, variant Creutzfeldt-Jakob disease, Gerstmann-Sträussler-Scheinker syndrome, kuru, fatal familial insomnia, and related disorders; hereditary cystatin c amyloid angiopathy; dementia pugilistica; other neurodegenerative diseases and nerve atrophy; and other disorders characterized by cerebral atrophy and detection of intracellular and/or extracellular fibrillar aggregates as the disorder progresses.

In a particular embodiment, the protein conformational disorder is Parkinson's disease. In another embodiment, the protein conformational disorder is Alzheimer's disease. In another embodiment the conformational disorder is a prion-related disease. In another embodiment, the conformational disorder is amyotrophic lateral sclerosis. In a particular embodiment, the conformational disorder is Huntington's disease.

In other embodiments, the base peptide sequence used for the process to manufacture the DSP composition is an epitope relevant to the pathology of protein conformational disorders affecting multiple organs or organs other than the central nervous system, selected from the group consisting of: spinal and bulbar muscular atrophy; hereditary systemic and cerebral amyloidosis, Finnish-type familial amyloidosis; senile systemic amyloidosis (a.k.a. senile cardiac amyloidosis), familial amyloid polyneuropathy; Type-2 diabetes, in particular pancreatic islet amyloidosis; dialysis-related amyloidosis (DRA); inflammation-associated reactive systemic amyloidosis (a.k.a. AA amyloidosis); aortic medial amyloidosis; medulary carcinoma of the thyroid; hereditary renal amyloidosis; light chain associated amyloidosis, light chain deposition disease, light chain cast nephropathy, light chain cardiomyopathy; atrial amyloidosis; injection-localized amyloidosis; cystic fibrosis (CF); sickle cell anemia, and other disorders wherein fibrillogenesis is observed in the affected organs or tissues.

In some embodiments, the base peptide sequence from which the DSP sequences are derived is selected from a group consisting of SEQ ID NO: 3 through 13.

In another embodiment, the protein conformational disorder is dialysis-related amyloidosis.

A particular embodiment of an aspect of the invention is a process of preparing a DSP composition as above, wherein the base sequence is selected from an epitope derived from proteins or peptides that do not strongly elicit immune reaction, and therefore is inadequate for preventing, ameliorating, or overcoming the pathology associated with the epitope. In a different embodiment, the epitope of the native sequence on its own as an antigen elicits an unwanted immune response, such as autoimmune-type of response, induction of anergy, or an agonistic or antagonistic stimulation that is contrary to a desired effect, each of which is detrimental to the improvement of the disease condition to which an immune reaction is sought. The unwanted immune response may be an autoimmune response against non-pathological tissue in vivo.

These DSP compositions may be used to elicit desired immune reactions. An embodiment of such use is to comprise therapeutic compositions useful for the treatment of PCDs as, for example, an active vaccine. Another embodiment of such use is to prepare antibodies against such DSPs, and to deliver said antibody as a passive vaccine. The immunizing composition may, but need not, include an adjuvant and other materials as immune boosters or stabilizers. The peptides comprising a DSP composition may be conjugated to a larger protein, such as keyhole limpet hemocyanin, bovine serum albumin, or ovalbumin for use as antigens, particularly for the preparation of antibodies. The peptides of a DSP may also be conjugated to a dendrimer, or synthesized as a dendrimer.

One aspect of the present invention is a pharmaceutical composition comprising a DSP composition as described herein, optionally as a pharmaceutically acceptable salt. In a preferred embodiment, such pharmaceutical composition comprising a DSP composition, when administered to a subject, causes a favorable modification of otherwise limited and inadequate immune response in the subject desirous of such a modification, such as an increase in appropriate immune responses, particularly to a protein associated with a pathological condition. The DSP may comprise one or more cassettes, such cassettes comprising the amino acid sequences that are derived from the first base peptide sequence. There may also be one or more cassettes having amino acid sequences that are derived from a second base peptide sequence of a second epitope.

Another aspect of the invention is the method of producing antibodies against DSP composition as described above, and the further aspect of the present invention is antibodies thus produced. In some embodiments, the method comprises (i) preparing a DSP composition according to the methods herein; (ii) administering said DSP composition to an animal; and (iii)(a) isolating antibodies immunoreactive with said DSP composition from said animal, or (iii)(b) isolating cells that produce antibodies immunoreactive with said DSP composition from said animal, and then isolating antibodies immunoreactive with said DSP composition from said isolated cells. The method of the instant invention encompasses producing and/or selecting an antibody which binds more specifically or which binds in a different conformation than those commonly obtained by selecting for a binding with a native epitope. A DSP composition is used to prepare antibodies that specifically bind to the base sequence, but including those that are different from antibodies elicited simply by the base peptide. The antibodies may bind to peptides or full length sequences corresponding to the native epitope. The antibodies may also bind to peptides or full length sequences corresponding to a disease-associated conformation of a specific epitope. In addition, the antibodies may bind to peptides or full length sequences that contain modifications such as post-translational modifications (for example, phosphorylation, acetylation, and methylation). The method is drawn to increasing the diversity of antibodies generated to react with a ligand. Further, the method is drawn to overcoming the problem of creating antibodies against ligands with low immunogenicity. Still further, the method is drawn to overcoming problems relating to generating antibodies having reactivities to only a single species. The method of the instant invention further encompasses the generation of novel functioning antibodies having antigen binding properties that elicit a varied amount of downstream consequences to the binding event. In some embodiments, the antibodies are immunoreactive with a protein comprising the base peptide, with or without post-translational modification, and wherein said protein is a full-length protein associated with the protein conformational disorder or a fragment of such full-length protein, and wherein said protein is in a pathological or non-pathological conformation.

In an embodiment of this aspect of the invention, the antibodies are modified antibodies having an engineered Fc region, wherein the engineered Fc region confers favorable pharmacodynamic profiles. In one embodiment, the Fc region enhances clearance of antibody-antigen complex. In another embodiment, the Fc region is not immunogenic to the subject. In certain embodiments, the Fc regions derive from an IgA, IgG, IgE, IgM, or IgD. The antibodies may be, for example, polyclonal or monoclonal antibodies. The antibody may also be a humanized antibody, an scFv antibody, or an antibody fragment such as a Fab fragment.

An aspect of the invention is a composition comprising a scaffold to which antibodies are attached, which antibodies are generated against a DSP composition as described above, wherein the base sequence is a sequence of a protein known to be associated with a protein conformational disorder. In one embodiment, the scaffold is a membrane compatible with haemodialysis. In a particular embodiment, the antibodies are conjugated to such membrane. In another embodiment, the antibodies are conjugated to a resin, such as CN—Br agarose resin (for example CN—Br Sepharose® (Pharmacia), to create an immunoaffinity resin.

The instant invention further comprises a method for the generation of antibodies useful as therapeutic agents for the treatment of disease.

In another embodiment, the instant invention comprises a method of creating antibody reagents for use in research studies. The instant invention also comprises a method of creating antibody reagents for use as diagnostic tools.

Another aspect of the present invention is a composition comprising antibodies generated against a DSP composition as described above, wherein the base sequence is a sequence of a protein known to be associated with a protein conformational disorder. More particularly, such protein is known to form an aggregate or fibril. In particular, antibodies thus generated are specific to the pathological conformation of such protein.

Another aspect of the present invention is a method of enhancing immune responses by administering a DSP composition to a subject in need thereof, which subject is afflicted with a PCD. This application also provides a method for prophylactic or therapeutic treatment of a PCD comprising the steps of administering to a subject in need thereof an effective amount of a DSP composition, for the prevention or amelioration of symptoms of said disorder. Using the same principle as for the production of antibodies, antibodies may be produced in vivo, i.e., the compositions for stimulating antibody production may be used as active vaccines. Immunization steps of all the representative methods described below can be modified for in vivo use of the immunogens of the present invention as vaccines. In a particular embodiment, the subject exhibits only a limited and inadequate immune response to undesirable immunogens associated with a PCD.

An aspect of the present invention is a method of treating a subject afflicted with a protein conformational disorder, comprising the steps of administering an antibody prepared using a DSP composition as described above. The treatment may be therapeutic, palliative, or prophylactic. In a particular embodiment, the protein conformational disorder is Parkinson's disease. In another embodiment, the protein conformational disorder is dialysis-related amyloidosis. In another embodiment, the protein conformational disorder is Alzheimer's disease.

Another aspect of the present invention is a method of treating a subject afflicted with a protein conformational disorder, comprising the steps of contacting under sterile conditions the blood of the subject to a membrane or a resin having conjugated with antibodies specific to a protein associated with a protein conformational disorder and prepared using a DSP composition, such antibodies described above, wherein the protein associated with a protein conformational disorder binds to such antibodies and is removed from the blood, and returning the blood to the subject. In a particular embodiment, the protein conformational disorder is dialysis-related amyloidosis. In one embodiment, the blood of the subject is contacted with the antibody as an additional step of therapeutic haemodialysis.

An embodiment of the invention is a method of prophylactic treatment of a subject at risk for developing a protein conformational disorder by contacting under sterile conditions the blood of the subject to a membrane or a resin having conjugated with antibodies specific to a protein associated with a protein conformational disorder and prepared using a DSP composition, such antibodies described above, wherein the protein associated with a protein conformational disorder binds to such antibodies and is removed from the blood, and returning the blood to the subject, whereby preventing the onset of such protein conformational disorder.

BRIEF DESCRIPTION OF THE DRAWINGS

FIG. 1A-D is a schematic depicting methodologies for designing synthetic peptide-based therapeutics. Panel A: how a peptide library is used for epitope discovery; Panel B: conceptual steps for generating Altered Peptide Ligand-based therapeutic; Panel C: a schematic of a dendrimer for multivalent peptide presentation; Panel D: random sequence polymer generation.

FIG. 4 shows the preferred defined substitutive rules for directed expansion of epitope permeability.

FIG. 5 shows a generic rule structure and ranges of substitutions of DSP synthesis.

FIG. 6 shows an example of the application of the DSP Synthesis Rules using a mock-source peptide (SEQ ID NO: 17).

FIG. 7A shows a schematic for the design of an alpha-synuclein DSP peptide. Top panel: the base peptide sequence (SEQ ID NO: 6); The bottom panel: the different proportions of alanine that may be used in the generation of each subunit (sequence disclosed as SEQ ID NO: 18).

FIG. 7B shows the application of the DSP synthesis rules to the peptide.

FIG. 8 shows a ribbon diagram of B2M.

FIG. 9 shows an example of the application of the DSP Synthesis Rules using Aβ1-42 peptide (SEQ ID NO: 19).

FIG. 10 shows an example of the application of the DSP Synthesis Rules using a huntingtin peptide.

DETAILED DESCRIPTION OF THE INVENTION

It has previously been shown that mixtures of related peptides may be therapeutically more effective than a single peptide. Lustgarten et al., *J. Immunol.* 2006, 176: 1796-1805; Quandt et al., *Molec. Immunol.* 2003, 40: 1075-1087. The effectiveness of a peptide mixture as opposed to a single peptide is the likelihood of interaction with the relevant epitopes that are not yet fully defined, particularly in terms of the conformationally specific interactions. Therefore, to increase and maintain the likelihood of long-term effectiveness, these previous treatment modalities have been modified. For example, a therapeutic composition based on an APL may include multiple peptides created by the APL method in combination with the original peptide, or other APLs. Fairchild et al., *Curr. Topics Peptide & Protein Res.* 6, 2004. Each APL would have a defined sequence, but the composition may be a mixture of APLs with more than one sequence. A reverse example involving conceptually similar altered peptide ligands involves an inventor's attempt to reduce the amount of variation created by pathogens to avoid immune recognition (viral alteration of immunogenic eptitopes over time, eg the creation of altered peptide ligands), by using the very changes created by the pathogen in an epitope sequence to create a limited diversity pool of peptides potentially useful in vaccinations (U.S. Pat. No. 7,118,874).

The instant invention draws out the most useful properties of the previous treatment modalities yet removes the limitations of each. The instant invention utilizes: (1) the specific immunologic relevance of a defined epitope peptide, (2) the modulatory properties of an APL, (3) the multivalency of MAPs, (4) and the alanine content from RSP to generate a directed expansion via alteration and degeneration of epitope variability that forms a complex yet directed peptide library useful for delivery as a vaccine. The approach is schematically represented in FIG. 2.

The instant invention relates to a "Directed-Sequence Polymer" (DSP). A DSP is a library of related peptides having a sequence derived from a base peptide sequence, which may be but not limited to a native epitope associated with a desired immune response. Designing a DSP starts with a sequence of a known peptide epitope. A DSP has one or more amino acid residues that differ from that of the base peptide sequence, the substitution of which is determined by a defined rule. A DSP composition comprising multiple DSPs is synthesized by applying a set of synthesis rules that define the amino acid variations and the ratio of occurrence of introduction of such amino acid residues at any given position of the sequence to the base peptide sequence. Thus, a DSP is not synthesized as a single peptide, but is always synthesized as part of a composition comprising multiple related DSPs, the overall mixture of which is reproducible and consistent with the rules of synthesis that were applied. The overall composition of amino acids that make up the epitope is modified via the introduction of different, related amino acids to each residue position, such introduction made in accordance with a defined set of rules. The result is a mixture of related peptides useful in and of itself as a therapeutic, and which is useful to induce production of antibodies that react with specificity with the known sequence, but are not easily elicited by a simple immunization using the known sequence. The schematic for the steps for creating a DSP composition, starting from the choice of a base peptide, is shown in FIG. 3.

The method of synthesizing a DSP composition utilizes and maintains the natural order of amino acid residues of a defined peptide sequence of a specified length. Each amino acid position is subjected to change based on a defined set of rules. In a preferred embodiment the amino acids are substituted according to the similarity depicted in FIG. 4. In another embodiment, the amino acids are substituted according to the methods described in Kosiol et al., *J. Theoretical Biol.,* 2004, 228:97-106. Alternatively, amino acids can be changed in accordance with the exemplary substitutions described in PCT/US2004/032598, page 10-11. Furthermore, amino acids can be changed in accordance with the methods set forth in US Patent Application Publication No. 2008/0146504. Alternatively, amino acids can be changed in accordance with the differences at a given position between species. Alternatively, amino acids can be changed in accordance with the differences at a given position between individual examples within the same species. Alternatively, the amino acids can be modified in accordance with an inflammatory or oxidative environment, with for example nitration, or phosphorylation. Alternatively, the amino acids can be changed or modified in order to promote, delay, accelerate or inhibit amlyoidogenesis.

For the solid phase synthesis procedure of the instant invention, the mixture of amino acids for a given position in the peptide is defined by a ratio one to another. Prior to starting the synthesis, such ratio is determined for each position along the peptide. The resulting directed order peptide mixture comprises a multiplicity of related peptide sequences.

I. Base Peptide Sequences

To create a meaningful DSP composition, one first needs to define the base peptide sequence to derive the DSPs from. The base peptide sequences can be derived in many ways. A peptide sequence useful for this purpose is a peptide sequence related to immune response in a mammal. Alternatively, the base peptide sequence can be derived from the group consisting of a virus, bacteria or parasite. These peptide sequences are, for example, partial sequences of certain heat shock proteins as an epitope, HLA derived peptide ligand sequences, organ-derived peptide sequences, and empirically derived peptide sequences, such as through screening of a library created by combinatory chemistry.

Peptide Sequences Related to Protein Conformational Diseases

In some embodiments, the base peptide sequence is an epitope relevant to the pathology of protein conformational disorders affecting the central and/or peripheral nervous system, selected from the group consisting of: Alzheimer's disease (AD), Dutch hereditary cerebral hemorrhage with amyloidosis (a.k.a cerebrovascular amyloidosis), congophilic angiopathy; Pick's disease, progressive supranuclear palsy; familial British dementia; Parkinson's disease (PD), Lewy-body related diseases, multiple system atrophy, Hallervorden-Spatz disease; amyotrophic lateral sclerosis (ALS); Huntington's disease (HD); spinocerebellar ataxia; neuronal intranuclear inclusion disease; hereditary dentatorubral-pallidoluysian atrophy; prion-related diseases such as scrapie, bovine spongiform encephalopathy, variant Creutzfeldt-Jakob disease, Gerstmann-Sträussler-Scheinker syndrome, kuru, fatal familial insomnia, and related disorders; hereditary cystatin c amyloid angiopathy; dementia pugilistica; and other neurodegenerative diseases characterized by cerebral and nerve atrophy and detection of intracellular and/or extracellular fibrillar aggregates as the disorder progresses.

In other embodiments, the base peptide sequence is an epitope relevant to the pathology of protein conformational disorders affecting multiple organs or organs other than the central nervous system, selected from the group consisting of: spinal and bulbar muscular atrophy; hereditary systemic and cerebral amyloidosis, Finnish-type familial amyloidosis; senile systemic amyloidosis (a.k.a. senile cardiac amyloidosis), familial amyloid polyneuropathy; Type-2 diabetes, in particular pancreatic islet amyloidosis; dialysis-related amyloidosis (DRA); inflammation-associated reactive systemic amyloidosis (a.k.a. AA amyloidosis); aortic medial amyloidosis; medulary carcinoma of the thyroid; hereditary renal amyloidosis; light chain associated amyloidosis, light chain deposition disease, light chain cast nephropathy, light chain cardiomyopathy; atrial amyloidosis; injection-localized amyloidosis; cystic fibrosis (CF); sickle cell anemia, and other disorders wherein fibrillogenesis is observed in the affected organs or tissues.

Examples of natively unfolded proteins and peptides, and those suspected to be natively unfolded, that undergo fibrillogenesis, and therefore associated with protein conformational disorders and may be use as the source sequences of the base peptides for the preparation of a DSP composition, include: prion protein and its fragments, amyloid beta protein and its fragments, abri protein, tau protein, alpha-synuclein and its central fragment, islet amyloid polypeptide (a.k.a. amylin), exon I of huntingtin, prothymosin alpha, amino-terminal domain of androgen receptor protein, ataxin-1, DRPLA protein (a.k.a. atrophin-1), and calcitonin.

Figure 2:
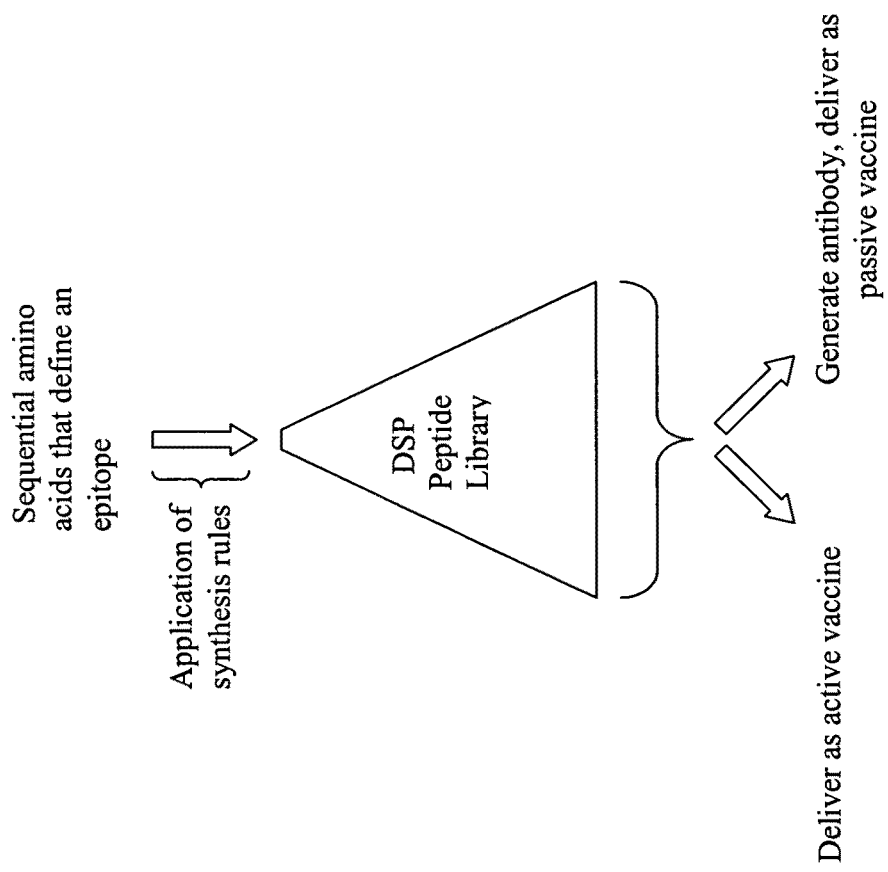
FIG. 2 is a schematic for conceptual steps for generating Directed-Sequence Polymers.
Figure 3:
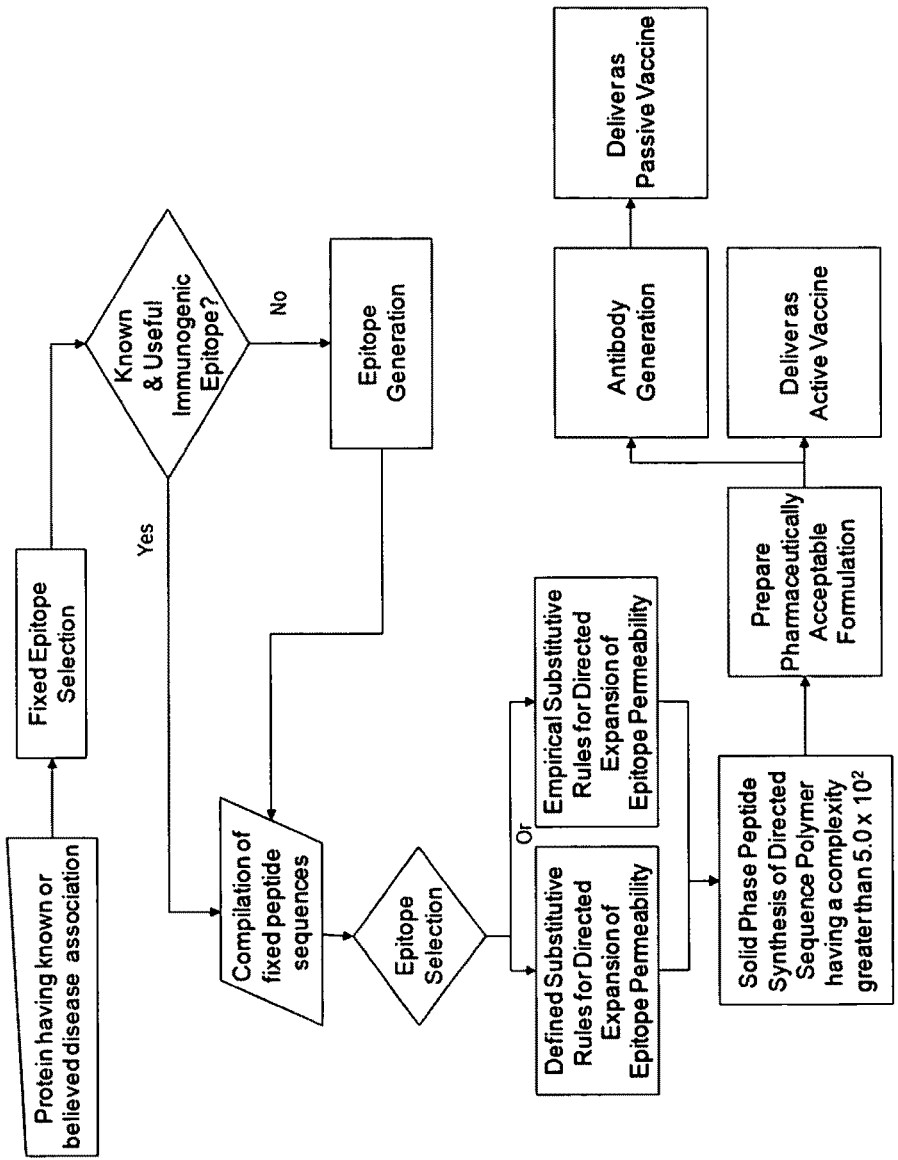
FIG. 3 shows the steps for preparing Directed-Sequence Polymers.
Figure 7A:
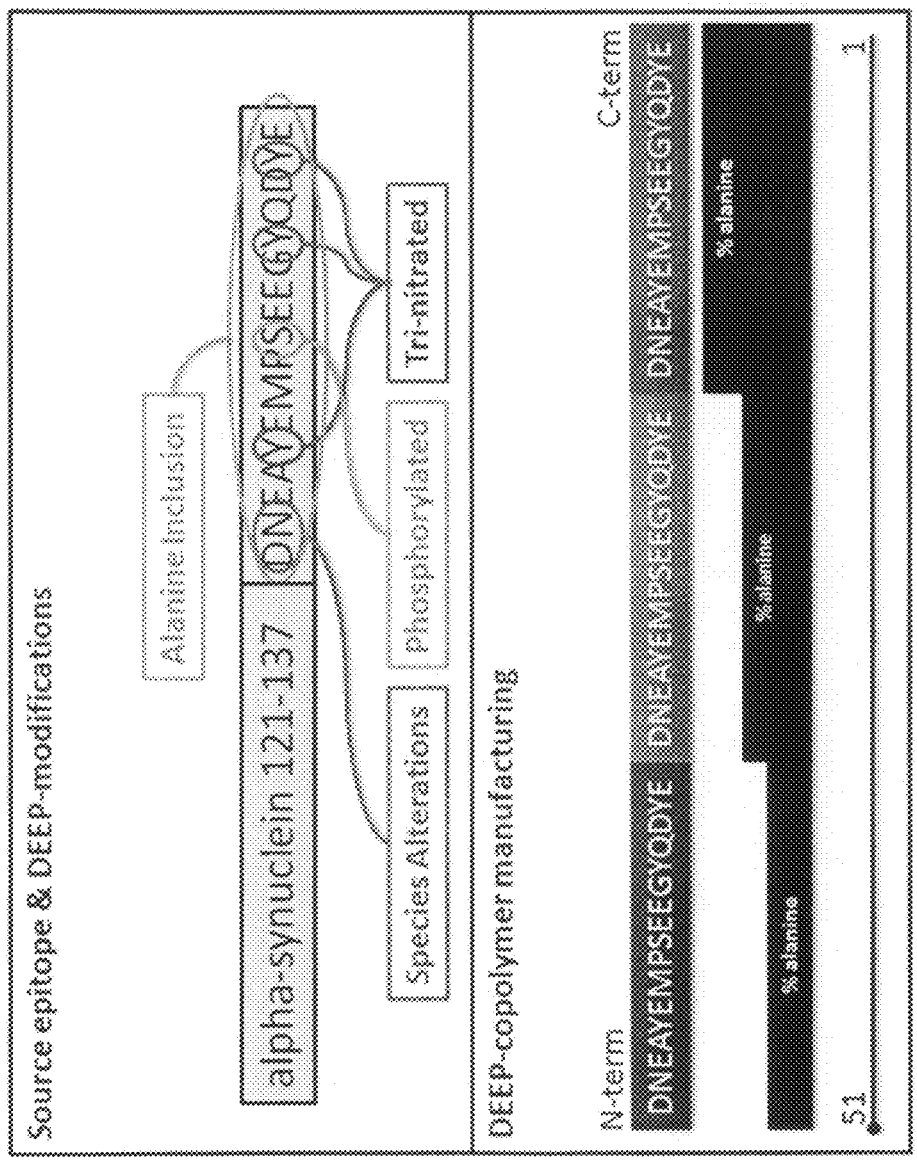
Figure 8:
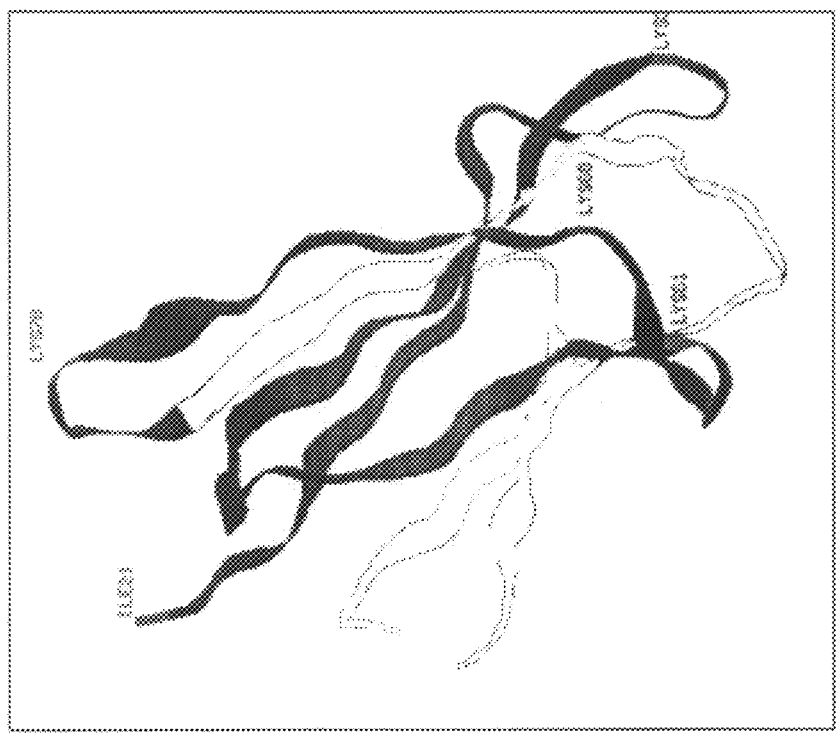

Examples of globular proteins that undergo fibrillogenesis and therefore associated with protein conformational disorders and may be use as the source sequences of the base peptides for the preparation of a DSP composition, include: cystatin c, transthyretin, beta 2 microglobulin, serum amyloid A protein and its fragments, huntingtin and its fragments (including exon I of huntingtin), immunoglobulin light chain variable domains, insulin, lysozyme (in particular human lysozyme), alpha lactalbumin, and monellin, ligand- and DNA-binding domains of androgen receptor protein, lactadherein and more specifically its fragments (for example, a.a. residue 245-294, a.k.a. medin), gelsolin, apolipoprotein A1, fibrinogen and its fragments, and atrial natriuretic factor. Fragments of all the proteins in this paragraph may also be used as source sequences.

As specific examples, in Alzheimer's disease, pathology correlates strongly with the presence of a 4 kDa amyloid beta (Aβ) peptide that is part of Aβ peptide precursor (APP), cleaved by enzyme presenilin 1 (PS1). Most Aβ are 40 amino acids long, and designated Aβ40, $A\beta_{40}$, $A\beta_{1-40}$, or, having varied amino terminal, $R_{x-40}$. Further, studies have indicated that the fibrillar form of $A\beta_{1-40}$ stimulates the microglia, which cell type is currently thought to play an important role in the pathogenesis of Alzheimer's disease. (Jekabsone, A. et al., *J. Neuroinflammation* 3:24 (2006)). The peptide sequence of $A\beta_{1-40}$ is shown as SEQ ID NO: 3 in Table I. On the other hand, $A\beta_{1-42}$, which is a minor fraction of plaque-forming Aβ, is thought to contribute to the initiation of the formation of fibrillar Aβ. This "long form" of the peptide is described as SEQ ID NO:4 in Table I. Therefore, the base peptide sequence is such Aβ peptide, exemplified by SEQ ID NO: 4. The base peptide sequence may also be that of shorter peptide, i.e. $A\beta_{x-40}$, $A\beta_{1-11}$, which has been reported in some cases to have clinical significance, $A\beta_{14-23}$, or $A\beta_{16-20}$. Tjernberg, L. O. et al., *Biochem. J.* 366:343-351 (2002).

A further specific example is Parkinson's Disease (PD). PD is a degenerative neurological disorder currently without a cure affecting 1-2% of the individuals over 50 years of age. The neuropathological hallmarks are characterized by progressive loss of neuromelanin containing dopaminergic neurons in the substantia nigra pars compacta (SNpc) with the presence of eosinophillic, intracytoplamic, proteinaceous inclusions termed Lewy Bodies (LB). α-Synuclein is the most abundant protein in Lewy Bodies, and appears to be an important mediator, perhaps even a causal factor, of toxicity in PD. Thus, reduction of toxic α-Synuclein is thought to be beneficial to PD patients. The sequence of one such mouse α-Synuclein peptide, derived from the C-terminal region of the full length protein, is shown as SEQ ID NO: 5 in Table I. (Benner, E. J. et al., *PLoS ONE* 3(1): e1376 (2008)). Further, elimination or sequestration of nitrated α-Synuclein and fragments thereof, appear to have favorable effects on the patients suffering from PD. Therapeutically effective antibodies are said to be directed at the nitrated α-Synuclein but not native. Therefore, the base peptide sequence is, for example, SEQ ID NO: 5. In another embodiment of the instant invention, the base peptide sequence is a fragment comprising amino acids 121-137 of human α-Synuclein (DNEAYEMPSEEGYQDYE) (SEQ ID NO: 6). In yet other embodiments, the α-Synuclein fragment (121-137) sequence is substituted at positions 121 and 122 in different species, tri-nitrated at each Y (tyrosine) position, and/or phosphorylated at S129.

Another embodiment of the invention is based on the base peptide sequence relevant to prion-diseases. SEQ ID NO: 10 is human prion protein sequence. A relevant peptide is selected from partial sequences of SEQ ID NO: 10. Various species' prion sequences are disclosed by Harmeyer, S. et al., *J Gen Virol.* 79(Pt 4):937-45 (1998), the entirety of which is incorporated herein by reference. The amino acid variations by species can be used to design the substituting amino acids.

Yet another embodiment of the invention is based on the base peptide sequence derived from superoxide dismutase I (SOD1). SOD1 mutation is known to have causal relationship with the pathology of some forms of familial ALS. It has been reported that the antisera raised against a mutant form of SOD1, human G93A SOD1 recombinant protein, had protective effect on a mouse model of ALS carrying G37R mutant SOD1 (line 29), which overexpress human SOD1 protein by 4-fold higher than endogenous mouse SOD1. Urushitani, M. et al., *Proc. Nat. Acad. Sci. USA*, 104(7): 2495-2500 (2007). An example of SOD1 protein sequence is SEQ ID NO: 11. Therefore a base peptide sequence is a partial sequence of SEQ ID NO: 9.

Misfolded protein also plays a role in Huntington's disease, a genetic disorder caused by the pathological expansion of a polyglutamine (polyQ) tract in the huntingtin (htt) protein (SEQ ID NO: 12), resulting in neurodegeneration and premature death of the afflicted individual. A single-chain antibody that binds to an epitope formed by the N-terminal 17 amino acids of htt (Lecerf, J.-M. et al., *Proc Natl Acad Sci USA.* 98(8): 4764-4769 (2001) SEQ ID NO: 7) has been shown to reduce symptoms in a Drosophila model of Huntington's disease. (Wolfgang, W. J. et al., *Proc Natl Acad Sci USA.* 102(32): 11563-11568 (2005)) Therefore, a base peptide sequence is SEQ ID NO: 7.

A further specific example is Dialysis-related Amyloidosis (DRA). DRA may be caused by different forms of blood filtration, such as haemodialysis, hemofiltration, or Continuous Ambulatory Peritoneal Dialysis (CAPD). DRA has an incidence of greater than 95% of patients on dialysis for more than 15 years with beta-2-microglobulin (B2M, SEQ ID NO: 9) amyloidosis being prevalent and predictably increasing over time. Conformational isomers of B2M have been observed in a clinical setting (Uji et al. Nephron Clin Pract 2009; 111:c173c181). B2M is part of the human leukocyte antigen (HLA) class I molecule, and has a prominent beta-pleated structure characteristic of amyloid fibrils. B2M is known to circulate as an unbound monomer distributed in the extracellular space. B2M undergoes fibrillogenesis to form amyloid deposits in a variety of tissues. This deposition causes renal failure, which causes an increase in synthesis and release of B2M, exacerbating the condition. Thus, in an embodiment of the invention, a protein the base sequence of which is used for preparation of a DSP composition is beta 2 microglobulin (SEQ ID NO: 9) and fragments thereof. An exemplary fragment of B2M is that spanning amino acid residues 21-40, SEQ ID NO: 8 in Table I, useful as a base peptide for DRA.

In some embodiments, the DSP (for example, a DSP used to treat or diagnose DRA) is modified with advanced glycation end (AGE) products, useful to elicit immune responses and to generate antibodies against certain AGE products.

AGE products are a heterogeneous group of carbohydrate molecules formed by non-enzymatic glycation and oxidative reactions between reducing sugars and protein amino groups. As described in Niwa (*Seminars in Dialysis,* 14(2) (March-April) 2001 pp. 123-126), AGE-modification of B2M is often observed in DRA patients, and appears to contribute to the pathology of DRA. In particular, the author observed imidazolone, Nε-(carboxymethyl)lysine (CML), and pentosidine modifications. As AGE-modified B2M accumulates, chemotaxis is enhanced, stimulating macrophages to release pro-inflammatory cytokines and interfering with collagen synthesis. Furthermore, AGE-B2M interacts with mononuclear phagocytes (MPs), cells important in the pathogenesis of inflammatory arthropathy. This interaction prompts the MPs to secrete elevated levels of TNFα and interleukin-1, worsening inflammation (Rashid et al., *IMAJ* 2006; 8:36-39).

To date, both haemodialysis and peritoneal dialysis have been found unsatisfactory in removing AGE products from the bloodstream; thus, new methods are needed to lower the levels of AGE products in DRA patients. Advanced glycation end products may be formed primarily on B2M aggregates rather than monomers, and thus may be useful in producing antibodies with specificity to the pathogenic aggregate form of B2M. Alternatively, oxidation of B2M may enhance amyloid deposition.

After identifying a candidate epitope, a probable set of additional related epitopes are generated using modeling and prediction algorithms described in readily available references, for example WO 2000/042559, align and analyze the predicted binding of these probable epitopes using available prediction methods described in, for example, WO 2005/103679, WO 2002/073193 and WO 99/45954. Selecting from the peptides having the highest predicted activity/binding, take 40% of the predicted sequences and acquire the percentage of any given amino acid at each position. Use those percentages to create the rules for amino acid incorporation into a DSP synthesis.

Other Sources of Base Peptide Sequences

Examples of epitopes identified as part of a naturally occurring, full length protein or synthetic peptides that were identified to have similar activities as such epitopes are shown in the table below.

TABLE I

Examples of epitopes

| Relevance | Peptide Sequence | Source/ Original Protein | Residue Number | Ref | SEQ ID NO: |
|---|---|---|---|---|---|
| Neuro-degeneration | DAEFRHDSGYEVHHQKLVFFA EDVGSNKGAIIGLMVGGVV | Amyloid beta | 1-40 | 54 | 3 |
| | DAEFRHDSGYEVHHQKLVFFA EDVGSNKGAIIGLMVGGVVIA | Amyloid beta | 1-42 | 55 | 4 |
| | MGKGEEGYPQEGILEDMPVDP GSEAYEMPSEEGYQDYEEA | Mouse alpha synuclein | 100-140 | 56 | 5 |
| | DNEAYEMPSEEGYQDYE | Human alpha synuclein | 121-137 | 57 | 6 |
| | MATLEKLMKA FESLKSF | Huntingtin | 1-17 | 58 | 7 |
| Dialysis-related amyloidosis | IQRTPKIQVYSRHPAENGKS | Beta-2 microglobulin | 21-40 | 59 | 8 |

Empirically Derived Base Peptide Sequences

As described in the above sections, peptide sequences with some significance to a disease state or an adverse reaction may be identified through experimental investigation of a relevant epitope. These sequences may include non-naturally occurring peptide sequences that proved to be useful in treating a disease or a condition, an example found in the international patent application publication WO 2006/031727, U.S. Pat. No. 6,930,168 and the related scientific publication Stern et al., *Proc. Nat. Acad. Sci. USA,* 2005, 102:1620-25.

Further, epitopes are empirically determined by identifying candidate sequences by positional scanning of synthetic combinatorial peptide libraries (see, for example, D. Wilson et al., above; R. Houghten et al., above; Hernandez et al., *Eur J Immunol.,* 2004, 34:2331-41), or by making overlapping peptide sequences of the entire protein of interest, and testing those peptides for immune reactivity (using, for example, any readout assay useful for such purposes, described in Current Protocols in Immunology Edited by John E Coligan, Ada M Kruisbeek, David H Margulies, Ethan M Shevach, Warren Strober N I H, John Wiley & Sons) in an in vitro or in vivo assay system appropriate for the disease and species the epitope is sought for. For example, for the design of a multiple sclerosis drug, an example of an appropriate system uses cells that derive from human subjects with MS.

II. Rules of Synthesis for Directed-Sequence Polymers

Steps in the creation of a DSP sequentially encompass the following:

(a) Identify a protein having known or believed association with a pathology.

(b) Select from within the protein a peptide or peptides, each having a fixed sequence, that are associated with the pathology and immunologically relevant. If no peptides have been described, then peptides useful in the treatment of the pathology of interest are created. One exemplary method is to create a library of peptides that collectively span the entire length of the protein of interest. This may be done by, for example, partial endopeptidase digestion or by peptide synthesis. The library is screened for immunologically relevant peptides using appropriate detection methods such as binding affinity determination using antibodies detected in the sera of patients with the target pathology. The peptides may be further examined for immunogenicity useful for the treatment of the pathology in an in vitro or in vivo experimental system.

(c) the amino acid substitutions are decided based on either of two sets of rules, defined or empirical and are set forth below;

(d) Solid phase synthesis of DSP according to the rules is performed, and pharmaceutically acceptable formulation the DSP is delivered as a therapeutic.

The rules of synthesis for a composition comprising DSPs are outlined below. Briefly, a DSP may be envisioned as a polypeptide having a defined length that is either the same length as or multiples of the length of the base peptide sequence. For each residue position of the base peptide sequence, one or more substitute residue is defined. The rule of synthesis defines the ratio among the original base peptide residue for that position, the first substitute residue, the second substitute residue, the third substitute residue, and an alanine, to occupy any given residue position.

The substitute residues are defined according either: (1) to a rational comparison and finding of similarities of relevant characteristics of the original residue with those of the substitute residue, (2) in accordance with the differences at a given position between species, (3) in accordance with the differences at a given position within individuals of the same species, or (4) to a comparison of reported experimental results on the relative activities of actual peptides having slight variations from the base sequence. The substitute residues defined in either of these two approaches are termed "conserved substitution" herein.

An example of a rational comparison and findings of similarity is the methods described by Kosiol et al., *J. Theoretical Biol.*, 2004, 228:97-106. Amino acids are grouped together in a matrix, referred therein as PAM replacement matrix. FIG. 4 is a table showing the amino acid similarity and grouping, according to Kosiol, based on the characteristics of the residues such as size, charge, hydrophobicity, etc. In FIG. 4, amino acids grouped together are considered interchangeable, with high likelihood of retaining characteristics common among the group, A comparison of experimental results showing the relative activities of peptides having slight variations from the base sequence can also be used as a basis for the rule for substitution. The sequences of the peptides responsible for observed changes are aligned and the type and percent presence of the new amino acid are noted. If there is more than one amino acid substitution at any given position of the peptide, the frequency of occurrence of an amino acid and the magnitude of activity change compared to the original sequence are taken into account to determine the order of prevalent substitution. Examples of the overall process leading up to the rule generation for DSP synthesis can be found using libraries (*Molec. Immunol.* 40:1047-1055; *Molec. Immunol.* 40:1063-74; *J Autoimmunity* 20:199-201; and *J. Immunol.* 163:6424-34), by making altered peptide ligands of overlapping peptides representing the entire protein of interest (Atkinson et al., *J. Clin. Invest.* 94:2125-29; Meini et al., *J. Clin. Invest.* 92:2633-43) or de novo (U.S. Pat. Nos. 7,058,515; 6,376,246; 6,368,861; 7,024,312; 6,376,246; 7,024,312; 6,961,664; 6,917,882). Briefly, a cellular material of interest is chosen as the assay system to rank the immunoreactivity of the peptides to be interrogated. Such an assay system can be either an in vitro or in vivo system, and can comprise adaptive or innate immune reactivity. Readouts for the assay system can be the up- or downregulation of the status of the activation state of a protein, a change in the localization of a protein, the expression of the mRNA encoding for the protein, the relative concentration of a protein, changes in the generation of specific cell types, changes in cellular phenotype, changes in cellular activation, changes in cell number, changes in organ size or function, changes in animal behavior or phenotype. Once the assay or assays are performed the results are analyzed to determine the prevalence of any particular amino acid as a conserved substitution. If more than three residues in a given position within the peptide sequence are identified as generating a change in immunologic function, the top three residues first by frequency of representation in the interrogated peptides, and second by the magnitude of changes elicited. Once chosen, the relative amounts of the residues are defined. As depicted in FIG. 5, each cassette, "y", has a set of amino acid ratios one to another that have a range of about 0-100 for the base (a), the primary change (b), the secondary change (c), and the tertiary change (d), whereas alanine (e) has a ratio of about 5-1000. The rules for the DSP synthesis continue with the combination of the cassettes in the order prescribed. The same block can be repeated either sequentially or separated by another block. On either side of the cassette sequence are N- and C-terminal modifiers. The number of cassettes is dictated by the requirements of the end length of the DSP which is required to be longer than 10 amino acids and shorter than 300 amino acids.

As described in FIG. 6, the instant invention envisions multiple epitopes to be defined as separate cassettes and synthesized sequentially. Cassette ratios within the same DSP may have different ratios of amino acids. Further, if there are less than three non-alanine amino acid substitutions, the percentage of the 'missing' substitution is added to the base sequence. Further, a cassette may be placed in any order with multiple appearances in the overall DSP synthesis. The N- and C-terminal Modifications reside prior to and after the entirety of the DSP cassettes respectively.

A cassette may be repeated more than once. After a desired number of multiples of the cassette, if the desired length of the DSP is not yet reached, the DSP sequence is further defined by applying the same process, possibly using different ratio among the original, substitute, second substitute, and alanine residues.

N or C-terminal DSP modifiers may be added to the synthesis rules. The purpose of such modifiers include but are not limited to enhancing binding to specific proteins as in the case of RDG-based amino acid sequences (U.S. Pat. No. 5,773,412; U.S. Pat. No. 5,770,565) used as targeting moieties, or peptides that are known to bind to a wide array of HLA-DR species, such as AKAVAAWTLK AAA (SEQ ID NO: 14) (U.S. App. Pub. No. 2006/0018915) as a DR-targeting moiety. Such modifiers may include moieties which enhance complexation to delivery systems including sustained release delivery systems. Modifiers can be resorbable matrix constructs/synthesizable backbones such as PLGA. Modifiers can be protease resistant moieties such as D-amino acids.

Thus, for any given base peptide sequence, a set of synthesis rules is applied to yield a composition comprising reproducible, consistent mixture of DSPs.

In some embodiments, the DSP (for example, a DSP used to treat or diagnose DRA) is modified with advanced glycation end (AGE) products. AGE products are a heterogeneous group of carbohydrate molecules formed by non-enzymatic glycation and oxidative reactions between reducing sugars and protein amino groups.

III. Peptide Synthesis Methods

Any known solid phase synthesis appropriate for peptide synthesis may be used to synthesize a composition comprising DSPs, for example as originally described by Merrifield (*J. Am. Chem. Soc.,* 1963, 85:2149) and any variation thereof. More specifically, the synthesis is done in multiple steps by the Solid Phase Peptide Synthesis (SPPS) approach using Fmoc protected amino acids. SPPS is based on sequential addition of protected amino acid derivatives, with side chain protection where appropriate, to a polymeric support (bead). The base-labile Fmoc group is used for N-protection. After removing the protecting group (via piperidine hydrolysis) the next amino acid mixture is added using a coupling reagent (TBTU). After the final amino acid is coupled, the N-terminus is acetylated.

The resulting peptides (attached to the polymeric support through its C-terminus) are cleaved with TFA to yield the crude peptide. During this cleavage step, all of the side chains protecting groups are also cleaved. After precipitation with diisopropyl ether, the solid is filtered and dried. The resulting peptides are analyzed and stored at 2-8° C.

Additionally, any peptide synthesis method that allows synthesis incorporating more than one amino acid species at a controlled ratio in any given position of the peptide sequence is suitable for use with this invention. Further, as described below, DSPs may be peptidomimetics or include unnatural or modified amino acid, necessitating the adaptation to allow addition of such chemical species to the polymers synthesized up to that point.

The synthesis may include unnatural amino acids, or amino acid analogs. In some embodiments, the DSPs are comprised of naturally occurring and synthetic derivatives, for example, selenocysteine. Amino acids further include amino acid analogs. An amino acid "analog" is a chemically related form of the amino acid having a different configuration, for example, an isomer, or a D-configuration rather than an L-configuration, or an organic molecule with the approximate size and shape of the amino acid, or an amino acid with modification to the atoms that are involved in the peptide bond, so as to be protease resistant when polymerized in a polypeptide.

The DSPs for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make DSPs of the present invention. The present invention contemplates DSPs containing both D- and L-amino acids, as well as DSPs consisting essentially of either L- or D-amino acids.

In certain embodiments, the DSPs of the present invention include such linear DSPs that are further modified by substituting or appending different chemical moieties. In one embodiment, such modification is at a residue location and in an amount sufficient to inhibit proteolytic degradation of the DSPs in a subject. For example, the amino acid modification may be the presence of at least one proline residue in the sequence; the residue is present in at least one of carboxy- and amino termini; further, the proline can be present within four residues of at least one of the carboxy- and amino-termini. Further, the amino acid modification may be the presence of a D-amino acid.

In certain embodiments, the subject DSPs is a peptidomimetic. Peptidomimetics are compounds based on, or derived from, peptides and proteins. The DSP peptidomimetics of the present invention typically can be obtained by structural modification of one or more native amino acid residues, e.g., using one or more unnatural amino acids, conformational restraints, isosteric replacement, and the like. The subject peptidomimetics constitute the continuum of structural space between peptides and non-peptide synthetic structures.

Such peptidomimetics can have such attributes as being non-hydrolyzable (e.g., increased stability against proteases or other physiological conditions which degrade the corresponding peptide DSPs), increased specificity and/or potency. For illustrative purposes, peptide analogs of the present invention can be generated using, for example, benzodiazepines (e.g., see Freidinger et al. in "Peptides: Chemistry and Biology," G. R. Marshall ed., ESCOM Publisher: Leiden, Netherlands, 1988), substituted gamma lactam rings (Garvey et al. in "Peptides: Chemistry and Biology," G. R. Marshall ed., ESCOM Publisher: Leiden, Netherlands, 1988, p 123), C-7 mimics (Huffman et al. in "Peptides: Chemistry and Biology," G. R. Marshall ed., ESCOM Publisher: Leiden, Netherlands, 1988, p. 105), keto-methylene pseudopeptides (Ewenson et al. *J. Med. Chem.,* 1986, 29:295; and Ewenson et al. in "Peptides: Structure and Function (Proceedings of the 9th American Peptide Symposium)," Pierce Chemical Co. Rockland, Ill., 1985), β-turn dipeptide cores (Nagai et al., *Tetrahedron Lett.,* 1985 26:647; and Sato et al. *J. Chem. Soc. Perkin Trans.,* 1986, 1:1231), β-aminoalcohols (Gordon et al. *Biochem. Biophys. Res. Commun.,* 1985, 126:419; and Dann et al. *Biochem. Biophys. Res. Commun.,* 1986, 134:71), diaminoketones (Natarajan et al. *Biochem. Biophys. Res. Commun.,* 1984, 124:141), and methyleneamino-modified (Roark et al. in "Peptides: Chemistry and Biology," G. R. Marshall ed., ESCOM Publisher: Leiden, Netherlands, 1988, p 134). Also, see generally, Session III: Analytic and synthetic methods, in "Peptides: Chemistry and Biology," G. R. Marshall ed., ESCOM Publisher: Leiden, Netherlands, 1988.

The molecular weight of a DSP composition can be adjusted during polypeptide synthesis or after the DSPs have been synthesized. To adjust the molecular weight during polypeptide synthesis, the synthetic conditions or the amounts of amino acids are adjusted so that synthesis stops when the polypeptide reaches the approximate length which is desired. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the DSPs with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by test reaction. The trifluoroacetyl-polypeptide with the desired molecular weight profile is then further treated with an aqueous piperidine solution to form a low toxicity polypeptide having the desired molecular weight.

In one particular embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

A further embodiment of the instant invention is the use of specific gylogenated forms of a DSP to create antibodies against such a form of a ligand. In one embodiment the ligand itself is an antibody. In one embodiment of the instant invention, the post-translational modification of a DSP is performed using glycogen synthase, or alternatively using chemical complexation techniques well known in the art.

IV. Antibody Production

The method is drawn to increasing the diversity of antibodies generated to react with a ligand. Further, the method is drawn to overcoming the problem of creating antibodies against ligands with low immunogenicity. Still further, the method is drawn to overcoming problems relating to generating antibodies having reactivities to only a single species. The instant invention comprises a method of creating antibody reagents for use in research studies. The instant invention comprises a method of creating antibody reagents for use as diagnostic tools. The instant invention further comprises a method for the generation of antibodies useful as therapeutic agents for the treatment of disease. Using the same principle, antibodies may be produced in vivo, i.e., the compositions for stimulating antibody production may be used as vaccines. Immunization steps of all the representative methods described below can be modified for in vivo use of the immunogens of the present invention as vaccines.

A method of preparing antibodies using a known antigen or a mixture of antigens is well known in the art. The method of preparing antibodies using a DSP composition is described in U.S. App. Publ. No. 2009-0036653. Briefly, antibodies are produced by designing and synthesizing the peptides comprising a DSP composition as described above, creating antibodies by introducing the DSP into an in vivo setting, or alternatively introducing the DSP into an in vitro setting, or still alternatively contacting the DSP with a system of maintaining the connection between antibody phenotype and genotype such as phage display, determining the activity of the generated antibodies by contacting the antibodies with the native molecule of interest, selecting antibodies having desired activity, such activity being either of a higher affinity antibody, or alternatively a lower affinity antibody, a single species reactivity, or alternatively a multi-species reactivity, a single-molecule of interest reactivity or alternatively a multi-molecule reactivity.

The instant invention also comprises a process for producing antibodies that are therapeutically or prophylactically useful in treatment of protein conformational disorders, or useful for use as research reagents, and as diagnostic tools for such disorders, by eliciting immune responses using a composition comprising directed epitope peptide mixtures. The invention also encompasses composition comprising antibodies thus produced.

The method of the instant invention also encompasses an augmentation of the paratopes associated with an antibody response to an antigen of interest. The method of the instant invention further encompasses the generation of novel functioning antibodies having antigen binding properties that elicit a varied amount of downstream consequences to the binding event.

Briefly, the method comprises the steps of selecting a protein relevant to a protein conformational disorder, determining relevant epitopes within the protein known or suspected to be closely associated with the disorder, selecting the relevant epitope, performing directed permutations of the epitope so as to create an expanded yet related series of antigens, performing solid phase synthesis thus creating a directed sequence polymer (DSP), using the DSP collectively as a set of antigens by placing the DSP in contact with a means of antibody generation, determining the activity of the generated antibodies, selecting antibodies having the desired activity, and utilizing the antibody as a single species reagent, multi-species reagent, single species diagnostic, multi-species diagnostic, or alternatively as a therapeutic. The means of antibody generation is, for example, an animal to be immunized by the DSP and cells from such an animal (e.g. spleen cells from a mouse for monoclonal antibody production), a phage display library, or a B cell library.

Alternatively, the instant invention encompasses methods of producing antibodies, the methods comprising: selecting a protein of interest, selecting the amino acids that make up the epitope, combining the amino acids into a linear peptide, performing directed permutations, synthesizing the DSP using solid phase chemistry, preparing the DSP as a pharmaceutically acceptable salt, introducing the DSP into a host, harvesting primary tissue containing antibody from the host after one week, alternatively harvesting primary tissue containing antibody from the host after a time greater one week, determining the activity of the generated antibodies, selecting, and utilizing the antibody as a reagent, diagnostic, or alternatively as a therapeutic.

The peptides comprising a DSP composition may be conjugated to a larger protein, such as keyhole limpet hemocyanin, bovine serum albumin, or ovalbumin for use as antigens. The peptides of a DSP may also be conjugated to a dendrimer, or synthesized as a dendrimer. The immunizing composition may include an adjuvant and other materials as immune boosters or stabilizers. Peptide dendrimers solve certain manufacturing issue of soluble peptide mixtures, in part by the promise of delivering to a patient a consistent ratio and quantity of each of the peptides in the mixture. This approach is schematically represented in FIG. 1C. Dendrimers are diverse. They can range in size from 2 kDa to greater than 100 kDa. The design of dendrimers intends to mimic two traits of naturally occurring biological structures: a globular structure and polyvalency. As described in two comprehensive reviews (P. Niederhafner et al., *J. Peptide Sci.* 11:757-788; K. Sadler and J. P. Tam, *Rev. Mol. Biotechnol.*, 2002, 90:195-229), they are complex compounds that contain highly branched components organized in a radial or wedge-like fashion, and are intended to have an extensive three-dimensional structure. They have three distinct structural features: a central core surface functionalities and branching units that link the two. Peptide dendrimers are designed as vehicles for delivery of: RNA and DNA as gene expression therapeutics, biosensor systems as diagnostics, inhibitors of autoimmune diseases, cancer metastasis, or to incorporate both T and B cell malaria-derived epitopes in the context of a vaccine. The strategy behind each of these applications is to use the globular, polyvalent structure to amplify the ligand:substrate interaction (D. Zanini and R. Roy, *J. Org. Chem.*, 1998, 63:3468-3491; J. Haensler and F. C. Szoka, *Bioconjug Chem.*, 1993, 4:372-379; Tam, James P et al., 1990, *J. Exp. Med.* 171:299-306).

Dendrimers have been made using amino, hydroxyl, carboxy, poly(propylenimine), silicone and polyamino amine cores (G. M. Dykes et al., *J. Chem. Technol. Biotechnol.*, 2001, 76:903-918, P. Sadler and J. Jezek, *Rev. Mol. Biotechnol.*, 2002, 80:195-229, and J. P. Tam, *Methods Org. Chemistry*, 2004, Vol E22d 129-168. Peptide dendrimers can be divided into three types: grafted peptide dendrimers, branching polyamino acids and multiple antigen peptides (MAPs).

The branching strategies in MAPs vary widely. The majority of first generation branches have used lysine. Second generation solid phase synthesis of MAPs has seen an interest in proline. The interest is said to come from both the properties of its secondary amine which decreases the reactivity during production, as well as its role in many cellular functions.

Simple MAPs have been synthesized using solid phase chemistry, with this type of synthesis strategy called divergent. Synthesis methods have been described which involves a two-step iterative reaction sequence producing concentric shells of dendritic beta-alanine units covalently linked in the second step to various functional groups (Kojima et al., *Bioconjugate Chem.*, 2000, 11:910-17). These types of MAPs, which are synthesized using the divergent strategy, by necessity have simple branching schemes with few distinct members, as the purification and characterization are untenable with more complex MAPs. The end-product needs to be purified away from deletion compounds having similar characteristics to the end-product. Purifications have been described using gel filtration chromatography, reverse phase high-performance liquid chromatography (HPLC), or electromigration methods.

For complex MAPs, for example, those having a multiplicity of branching moieties, convergent synthesis is the preferred synthesis strategy. Convergent synthesis can be performed using either fragment condensation or ligation of the pre-purified fragments. There are many types of ligations: natural (true peptide bond created), thiol, hydrazone, or other. MAPs prepared using convergent synthesis strategies are easier to purify, as the end-product will look distinctly different from the reaction byproducts. HPLC was first used to purify convergent MAPs (J. C. Spetzler et al., *Int. J. Pept. Protein Res.*, 1995, 45:78-85).

Thus produced, another aspect of the present invention is a composition comprising antibodies generated against a DSP composition as described above, wherein the base sequence is a sequence of a protein known to be associated with a protein conformational disorder. More particularly, such protein is known to form an aggregate or fibril. In particular, antibodies thus generated are specific to the pathological conformation of such protein.

In an embodiment of this aspect of the invention, the antibodies are modified antibodies having an engineered Fc region, wherein the engineered Fc region confers favorable pharmacodynamic profiles. In one embodiment, the Fc region enhances clearance of antibody-antigen complex. In another embodiment, the Fc region is not immunogenic to the subject. Such modified antibodies may be created after antibodies with certain desired (complementarity determining regions) are identified, by replacing chemically or by molecular biological means the Fc region with an IgA, IgG, IgE, IgM, or IgD region.

In another embodiment, the antibodies are humanized antibodies having desired CDRs (complementarity determining regions), such CDRs having been identified using DSP compositions or antibodies having such CDRs having been generated using DSP compositions. Humanized antibodies may be made according to any means known in the art, including CDR grafting and the introduction of point mutations to reduce immunogenicity. In yet another embodiment, the antibodies are single chain variable fragment (scFv), either engineered from an identified antibody, or generated using a phage display library and other means and screened for desired antibodies using DSP compositions. Methods of scFv production and phage display are known in the art.

The antibodies may also have a detectable label, such as a radiolabel, an enzymatic label, or a fluorescent label. In some embodiments, the fluorescent label is selected from the group consisting of Texas Red, phycoerythrin (PE), cytochrome c, and fluorescent isothiocyanate (FITC). In addition, labels such as biotin followed by streptavidin-alkaline phosphatase (AP), horseradish peroxidase (HRP) are contemplated.

This disclosure also provides antibodies with at least 70%, 80%, 90%, 95%, or 99% amino acid sequence identity to the anti-DSP antibodies described above. Antibodies in general have well characterized structure-activity relationships, and one of skill in the art would be well aware that certain mutations would be unlikely to disrupt the antigen-binding function of an antibody. For example, conservative substitutions in the constant region would be unlikely to disrupt antigen binding, while substitutions in the CDRs would be more likely to disrupt antigen binding.

An aspect of the invention is a composition comprising a scaffold or support material to which antibodies are attached, which antibodies are generated against a DSP composition as described above, wherein the base sequence is a sequence of a protein known to be associated with a protein conformational disorder. In one embodiment, the scaffold is a membrane compatible with haemodialysis. Membranes for haemodialysis are typically semi-permeable, allowing for water and some dissolved solutes to pass through. The membranes can have different pore sizes and are thus categorized as low-flux or high-flux. Membranes can be made from a variety of materials, including cellulose acetate, polyarylethersulfone, polyamide, polyvinylpyrrolidone, polycarbonate, and polyacrylonitrile. In a particular embodiment, the antibodies are conjugated to such membrane. This will allow for removal of specified proteins at while haemodialysis is carried out. This process is useful, inter alia, for treating removing amyloid forms of B2M and treating DRA. In another embodiment, the antibodies are conjugated to a resin, such as CN—Br agarose resin (for example CN—Br Sepharose® (Pharmacia), to create an immunoaffinity resin.

V. Pharmaceutical Composition

One aspect of the present invention is a pharmaceutical composition comprising a DSP composition. As described below in the method of treatment as an aspect of this invention, the DSP composition produced by the process of the invention is useful in treatment of a protein conformational disorder in a subject.

The DSPs of the present invention may be administered to the subject as a composition which comprises a pharmaceutically effective amount of DSPs and an acceptable carrier and/or excipients. A pharmaceutically acceptable carrier includes any solvents, dispersion media, or coatings that are physiologically compatible. Preferably, the carrier is suitable for oral, rectal, transmucosal (including by inhalation), parenteral, intravenous, intramuscular, intraperitoneal, intradermal, transdermal, topical, or subcutaneous administration. One exemplary pharmaceutically acceptable carrier is physiological saline. Other pharmaceutically acceptable carriers and their formulations are well-known and generally described in, for example, *Remington's Pharmaceutical Science* (18$^{th}$ Ed., ed. Gennaro, Mack Publishing Co., Easton, Pa., 1990). Various pharmaceutically acceptable excipients are well-known in the art and can be found in, for example, *Handbook of Pharmaceutical Excipients* (4$^{th}$ ed., Ed. Rowe et al. Pharmaceutical Press, Washington, D.C.). The composition can be formulated as a solution, microemulsion, liposome, capsule, tablet, or other suitable forms. The active component which comprises the copolymer may be coated in a material to protect it from inactivation by the environment prior to reaching the target site of action. The pharmaceutical compositions of the present invention are preferably sterile and non-pyrogenic at the time of delivery, and are preferably stable under the conditions of manufacture and storage. When desirable, the composition further comprises components to enhance stability, permeability, and/or bioavailability, such as particulate forms protective coatings, protease inhibitors or permeation enhancers for various routes of administration, including parenteral, pulmonary, nasal and oral.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pre-gelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well-known in the art.

In one embodiment, the oral composition is enterically-coated. Use of enteric coatings is well known in the art. For example, Lehman (1971) teaches enteric coatings such as Eudragit S and Eudragit L. The Handbook of Pharmaceutical Excipients, $2^{nd}$ Ed., also teaches Eudragit S and Eudragit L applications. One Eudragit which may be used in the present invention is L30D55. Preparations for oral administration may be suitably formulated to give controlled release of the active compound.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compositions may be formulated for administration by injection, e.g., by bolus injection or continuous infusion in a parenteral, intravenous, intraperitoneal, intramuscular, or subcutaneous manner. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile pyrogen free water, before use.

In a preferred embodiment, compositions comprising DSP compositions are formulated in accordance with routine procedures as pharmaceutical compositions adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together. Where the composition is to be administered by infusion, it can be dispensed with an infusion bottle containing sterile pharmaceutical grade water or saline, with the intervals between administrations being greater than 24 hours, 32 hours, or more preferably greater than 36 or 48 hours. Where the composition is administered by injection, an ampoule of sterile water or saline for injection can be provided so that the ingredients may be mixed prior to administration.

In other embodiments of the present invention, the pharmaceutical compositions are regulated-release or sustained release formulations. DSP compositions of the present invention may be admixed with biologically compatible polymers or matrices which control the release rate of the copolymers into the immediate environment. Controlled or sustained release compositions include formulation in lipophilic depots (e.g., fatty acids, waxes, oils). One embodiment of sustained release formulations is transdermal patches.

In some embodiments of the present invention, pharmaceutical compositions comprise DSPs formulated with oil and emulsifier to form water-in-oil microparticles and/or emulsions. The oil may be any non-toxic hydrophobic material liquid at ambient temperature to about body temperature, such as edible vegetable oils including safflower oil, soybean oil, corn oil, and canola oil; or mineral oil. Chemically defined oil substance such as lauryl glycol may also be used. The emulsifier useful for this embodiment includes Span 20 (sorbitan monolaurate) and phosphatidylcholine. In some embodiments, a DSP composition is prepared as an aqueous solution and is prepared into an water-in-oil emulsion dispersed in 95 to 65% oil such as mineral oil, and 5 to 35% emulsifier such as Span 20. In another embodiment of the invention, the emulsion is formed with alum rather than with oil and emulsifier. These emulsions and microparticles reduce the speed of uptake of DSPs, and achieve controlled delivery.

In another embodiment, the controlled and/or sustained delivery is achieved by implantable medical devices coated with sustained-release formulations, or implantable pharmaceutical formulation suitable for sustained-release of the active components.

Some embodiments of the invention are pharmaceutical compositions for targeted delivery of the DSP composition of the invention. In such embodiments, a pharmaceutical composition comprises a DSP composition that is complexed with a targeting moiety. The targeting moiety allows localized delivery of the DSP composition to a desired location or microenvironment within the subject. A targeting moiety include, and may be selected from, the group comprising a chemical group or functionality such as biotin or simple sugars, a single or double stranded DNA sequence of various lengths, a single or double stranded RNA sequence of various lengths, a peptide of various lengths, an antibody including single chain antibodies, Fab', or modified antibodies, a lipid, or a glycolipid. More than one of such moiety may be used at the same time in combination. For examples of targeting moieties, see U.S. Pat. No. 6,268,488; and U.S. Appl. Pub. No. 2003/0190676.

In one embodiment of the invention, the complex has characteristics of a prodrug, causing the DSP composition to exhibit no pharmaceutical activity of the present invention until the dissolution of the complex in the subject. In another embodiment, the complex does not affect the activity of the DSP composition.

Any methods generally known to one skilled in the art may be used to produce a complex of the instant invention and a targeting moiety. The target moiety may be complexed to the DSPs by a chemical bond, which may be covalent, ionic, hydrophobic, or van der Waals force, directly or through another chemical entity. Alternatively, the target moiety may be co-localized with the DSPs through common medium such as a biocompatible resin within which the DSP composition is included. The manner of forming a complex is chosen also based on the active state of the instant invention while existing in the combination and whether a permanent complex or a transitory complex is desired.

In some embodiments, the pharmaceutical compositions also include additional therapeutically active agents. Such additional ingredient can be one or more of: an additional DSP composition that binds to a different target, an antibody which activates inflammatory molecules, or cytokines. Further additional ingredient can be activating cytokines and chemokines (as described in Shaw, Jennifer, *Infection and Immunity*, 69:4667-4672, 2001) taken from the group consisting of Mip1β, Mip1α, Mip-2, Mip3α, IP-10, MCP-1, TCA-3, IL-1, IL-18, IL-6, IFNγ, MIF, IL-12, CCR7.

Further, a form of vitamin D that is or becomes biologically active within the body of the subject receiving such form of vitamin D may also be used as an additional ingredient. The two main forms of vitamin D are: vitamin D3 or cholecalciferol, which is formed in the skin after exposure to sunlight or ultraviolet light, and ergocalciferol or vitamin D2 which is obtained by irradiation of plants or plant materials or foods. The differences are situated in the side chain. Vitamin D3 may be obtained from natural sources such as fatty fish such as herring and mackerel. In the body, two other forms of vitamin D3 can be found. Vitamin D3 is hydroxylated in the liver into 25-hydroxyvitamin D3 (25(OH)D), and subsequently in the kidney into 1,25-dihydroxyvitamin D3 (1,25(OH)$_2$D), which is the active metabolite that stimulates the calcium absorption from the gut (Feldman et al., 2005). When 1,25(OH)$_2$D is sufficiently available, 24,25-dihydroxyvitamin D (24,25 (OH)$_2$D) is formed in the kidney, which is further catabolized.

In certain embodiments, the composition is capable of raising an immune response without an adjuvant.

Another class of therapeutically active agents useful as an additional agent is immune boosters which increases the production of common lymphoid precursors (CLPs) from the multilineage potential cells. An example of such agent is PBI-1402 developed by ProMetic in Quebec, Canada.

The invention further provides a kit comprising (i) a composition comprising a DSP composition and (ii) instructions for administering the composition to a subject in need thereof at intervals greater than 24 hours, more preferably greater than 36 hours, for the treatment of a disease, such as a protein conformational disorder. In one embodiment, the PCD is DRA. In a preferred embodiment, the DSP composition is formulated in dosages for administration of greater than about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or any intervening interval thereof. In another embodiment of the kits described herein, the instructions indicate that the DSP is to be administered every about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or any interval in between. Kits may comprise additional components, such as packaging, instructions, and one or more apparatuses for the administration of the copolymer, such as a hypodermic syringe.

Other embodiments of the invention are kits that comprise a scaffold containing one or more DSP-generated antibody clones and the corresponding instructions on combining with haemodialysis.

Another aspect of the invention is a pharmaceutical composition comprising one or more antibodies generated and produced using the process described herein elsewhere. An antibody or antibodies that react to a protein conformational disease can be used to neutralize pathological proteins that such antibodies specifically bind, or to facilitate clearing from the body of a patient afflicted with such disease.

Pharmaceutically acceptable carriers and their formulations are well-known and generally described in, for example, *Remington's Pharmaceutical Science* (18$^{th}$ Ed., ed. Gennaro, Mack Publishing Co., Easton, Pa., 1990). Various pharmaceutically acceptable excipients are well-known in the art and can be found in, for example, *Handbook of Pharmaceutical Excipients* (4$^{th}$ ed., Ed. Rowe et al. Pharmaceutical Press, Washington, D.C.). Further, formulations suitable for antibodies are generally known in the art, including buffers and excipients, and preservative agents such as protease inhibitors that are suitable for pharmaceutical use. The pharmaceutical compositions of the present invention are preferably sterile and non-pyrogenic at the time of delivery.

The compositions may be formulated for administration by injection, e.g., by bolus injection or continuous infusion in a parenteral, intravenous, intraperitoneal, intramuscular, or subcutaneous manner. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile pyrogen free water, before use. Typically, compositions for intravenous administration are solutions in sterile isotonic aqueous buffer. Where necessary, the composition may also include a solubilizing agent and a local anesthetic such as lignocaine to ease pain at the site of the injection.

In certain embodiments, antibodies are single chain variable fragments, to facilitate transport into the tissues due to its smaller size compared to naturally occurring antibodies. Such antibodies may further be associated with a carrier or agent to cross the blood brain barrier, for example, an anti-transferring antibody. See, for example, Friden et al., Anti-transferrin receptor antibody and antibody-drug conjugates cross the blood-brain barrier, PNAS Jun. 1, 1991 vol. 88 no. 11 4771-4775.

VI. Methods of Treatment Administration of DSP

The instant invention provides for a further improvement on the need to improve the effectiveness of peptide immunotherapies. The improvement takes form in an ability to dynamically administer the compound based on the ability of the compound to achieve an increased immune activation, while generating either a $T_H1$ immune posture, or a $T_H2$ immune posture, and while producing anti-compound antibodies at either a low or a high level. Dynamic administration of random sequence copolymer is comprised of any combination of dose, regimen, route of administration, and/or formulation. This dynamic immunomodulation provides for increased effectiveness at any of the multiple stages of a disease within a particular patient, as well as the ability to treat multiple, pathogenic antigenic-determinant unrelated diseases more effectively.

The invention provides methods for the treatment or prevention of a disease in a subject, preferably in a human, which subject is afflicted with or is suspected to be afflicted with the disease. Another embodiment of the present invention is a method for prophylactically treating a subject at risk of developing a protein conformational disorder by administering a DSP composition. A subject at risk is identified by, for example, determining the genetic susceptibility to a protein conformational disorder by testing for alleles of HLA that are associated with such disorder, and/or based on familial history, or other genetic markers that correlate with such disorder. In addition, many patients receiving dialysis or other form of blood filtration are at risk for developing DRA, especially if the blood filtration is performed over a long period of time, such as more than 3, 5, 7, or 10 years. Further, subjects that are asymptomatic but show biochemical markers of a protein conformational disorder are at risk of developing such disorder.

One aspect of the invention provides methods of treating or preventing a disease, the method comprising administering to said subject a dosing regimen of an effective amount of a DSP composition for the amelioration of a disease treatable with the DSP composition, said effective amount delivered to said subject at time intervals greater than 24 hours, 36 hours, or more preferably greater than 48 hours. A related aspect of the invention provides a method for the treatment of a subject in need thereof, comprising administering to said subject a dosing regimen of an effective amount of a DSP composition for the amelioration of a disease treatable with the DSP composition, said effective amount delivered to the subject using a sustained-release formulation which administers the DSP composition over a period of at least 2 days, at least 4 days, or at least 6 days, wherein the effective amount is an amount that is effective if delivered daily.

One aspect of the invention is the administration of a DSP composition to a subject in need there of, as described above, in combination with other therapeutic agents that are effective in treating the conditions that are treated by administration of the DSP, or conditions that accompany or occur concurrently with the conditions that are treated by administration of the DSP. The additional therapeutically active agents may treat the same or related disease as the DSP composition, or may be intended to treat an undesirable side effect of administration of the DSP composition, such as to reduce swelling at a site of intradermal injection. Alternatively, the other therapeutic agents enhance the activity of DSP compositions. Such additional therapeutic agents are, by way of example, antibodies, cytokines, growth factors, enzyme inhibitors, antibiotics, antiviral agents, anti-inflammatory including steroids, immune boosters, antimetabolites, soluble cytokine receptors, and vitamin D or agents that increase the level of circulating vitamin D, toll-like receptor agonists, CpG oligodeoxynucleotides, surface charged poly(lactide-co-glycolide) microparticles, any of the above encapsulated into liposomes, archaeosome adjuvants, mucosal adjuvants, polyphosphazenes. Additional therapeutically active agents also include copolymers which bind to a HLA molecule associated with the disease such as another DSP composition. The HLA molecule may be an HLA-DQ molecule or an HLA-DR molecule. The enzyme inhibitor may be a protease inhibitor or a cyclooxygenase inhibitor. Examples of the therapeutically active agents to be administered in conjunction with the DSP composition are recited in Section IV, "Pharmaceutical Composition" section, though the administration of these agents are not limited to co-administration as a single composition. The additional therapeutic agents may be administered before, concomitantly with, or after the administration of the DSP composition, at such time that the effect of the additional therapeutic agents and the effect of the DSP composition overlap at some time point.

Alternatively, antigen/epitope non-specific treatments and therapies directly targeted at controlling T lymphocytes or their functions may be administered in conjunction with the DSP composition. The therapeutic agents useful for such treatment include Muromonab-CD3 (OKT3), antilymphocyte globulin (ALG), antithymocyte globulin (ATG), or interleukin-2 receptor monoclonal antibody ("mAb") daclizumab or basiliximab. Other agents include soluble CTLA-4, an anti-CD154 mAb; anti-CD11a; a humanized mAb which inhibits VLA-4; anti-CD2, 3, or 4 antibodies; and anti-CD152 antibodies (J. B. Matthews et al., Amer. J. Transplantation, 2003, 3: 794-80).

When treating protein conformation diseases, such as DRA, it may be advantageous to administer the DSP therapeutic or DSP-specific antibody therapeutic in combination with one or more additional therapy. In certain embodiments, the additional therapy lowers B2M levels in the patient. In some embodiments, the additional therapy is a form of dialysis such as haemodialysis or CAPD. The efficacy of CAPD in removing B2M from the bloodstream is discussed in Lysaght et al. (Peritoneal Dialysis International, Vol. 9, pp 29-35, 1989). In various embodiments, B2M is removed from a patient's bloodstream using a direct hemoperfusion column comprising porous cellulose beads to which hydrophobic hexadecyl alkyl chain is covalently bound, as discussed in Kutsuki H (Biochimica et Biophysica Acta 1753 (2005) 141-145). In certain embodiments, the additional therapy removes unwanted products of haemodialysis. For instance, dialysis patients often have elevated levels of parathyroid hormone, advanced glycation end products, advanced lipoxidation end products, advanced oxidation protein products, granulocyte inhibitory proteins, or leptin (Horl, J Am Soc Nephrol 13: S62-S71, 2002). Levels of these products may be reduced by using a biocompatible membrane for haemodialysis. In addition, levels of these products may be reduced by passing the patient's blood over a substrate that contains a molecule (e.g. an antibody) specific to one or more of these products.

As discussed earlier, elevated levels of $Cu^{++}$ promote the assembly of B2M monomers into amyloid aggregates. For this reason, it may be desirable to administer the therapies herein together with an agent that reduces $Cu^{++}$ levels in a patient. For example, a copper chelator such as vitamin C, molybdenum, tetrathiomolybdate (e.g. Coprexa), penicillamine, trientine, or sulfur-containing amino acids may be used.

On the same principle, $Cu^{++}$ may be added to a DSP peptide to promote its assumption of the disease-specific conformation. This may occur during the manufacturing process. After the peptide has taken on the disease-specific conformation, the copper may be removed, for instance with a copper chelator. The DSP peptide may then be used as a therapeutic or to generate an antibody.

In some embodiments, the therapeutic is co-administered with an inflammation-reducing agent. Inflammation-reducing agents are well known in the art and include steroids and NSAIDs (which typically inhibit COX enzymes). Classes of steroids include glucocorticoids and corticosteroids; examples include Hydrocortisone (Cortisol), Cortisone acetate, Prednisone, Prednisolone, Methylprednisolone, Dexamethasone, Betamethasone, Triamcinolone, Beclometasone, Fludrocortisone acetate, Deoxycorticosterone acetate (DOCA), and Aldosterone, NSAIDS include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as γ-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof; and other analgesics, such as acetaminophen. The dosage of analgesic and/or antipyretic such as aspirin, acetaminophen, etc. will be known to those skilled in the art and can be in the range of 80 mg to 250 mg. The dosage of NSAID will be known to those skilled in the art and can be in the range of 80 mg to 500 mg.

In one embodiment of the methods described herein, the route of administration can be oral, intraperitoneal, transdermal, subcutaneous, by intravenous or intramuscular injection, by inhalation, topical, intralesional, or by infusion; liposome-mediated delivery; intrathecal, gingival pocket, rectal, intravaginal, intrabronchial, nasal, transmucosal, intestinal, ocular or otic delivery, or any other methods known in the art as one skilled in the art may easily perceive. Administration can be systemic or local. In the event more than one DSP composition is being administered to a subject during the same or overlapping time period, such additional therapeutic agent may be administered by a route different from that for the administration of the DSP composition.

In general, an embodiment of the invention is to administer a suitable dose of a therapeutic DSP composition that will be the lowest effective dose to produce a therapeutic effect, for example, mitigating symptoms. The therapeutic DSP compositions are preferably administered at a dose per subject, which corresponds to a dose per day of at least about 2 mg, at least about 5 mg, at least about 10 mg, or at least about 20 mg as appropriate minimal starting dosages, or about x mg, wherein x is an integer between 1 and 20. In one embodiment of the methods described herein, a dose of about 0.01 to about 500 mg/kg can be administered. In general, the effective dosage of the DSP composition of the present invention is about 50 to about 400 micrograms of the composition per kilogram of the subject per day. In one specific embodiment, the equivalent dosage per day, regardless of the frequency with which the doses are administered, is from about 5 to 100, or more preferably, from about 10 to 40, or more preferably about 20 mg/day. In another specific embodiment, each individual dosage in the treatment regimen is from about 5 to 100, or more preferably from about 10 to 40, or more preferably about 20 mg/dose.

However, it is understood by one skilled in the art that the dose of the DSP composition of the invention will vary depending on the subject and upon the particular route of administration used. It is routine in the art to adjust the dosage to suit the individual subjects. Additionally, the effective amount may be based upon, among other things, the size of the DSPs, the biodegradability of the DSPs, the bioactivity of the DSPs and the bioavailability of the DSPs. If the DSPs does not degrade quickly, such as is expected when the DSPs comprise unnatural amino acids or are peptidomimetics, is bioavailable and highly active, a smaller amount will be required to be effective. The actual dosage suitable for a subject can easily be determined as a routine practice by one skilled in the art, for example a physician or a veterinarian given a general starting point. For example, the physician or veterinarian could start doses of the DSP composition of the invention employed in the pharmaceutical composition at a level lower than that required in order to achieve the desired therapeutic effect, and increase the dosage with time until the desired effect is achieved. The dosage of the DSP composition may either be increased in the event the patient does not respond significantly to current dosage levels, or the dose may be decreased if an alleviation of the symptoms of the disorder or disease state is observed, or if the disorder or disease state has been ablated, or if an unacceptable side effects are seen with the starting dosage.

In one embodiment, a therapeutically effective amount of the DSP composition is administered to the subject in a treatment regimen comprising intervals of at least 36 hours, or more preferably 48 hours, between dosages. In another embodiment, the DSP composition is administered at intervals of at least 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or the equivalent amount of days. In some embodiments, the DSP composition is administered every other day, while in other embodiments it is administered weekly. If two different DSP compositions, or DSP composition with another therapeutic agent, are administered to the subject, such administration may take place at the same time, such as simultaneously, or essentially at the same time, such as in succession. Alternatively, their administration may be staggered. For example, two DSP compositions which are each administered every 48 hours may both be administered on the same days, or one may be administered one day and the other on the next day and so on in an alternating fashion.

Treatment regimens with longer dosing intervals, consequently often with lower total exposure of DSPs, are expected to induce lower titers of antibodies against DSPs themselves, while still inducing desired protective effects. Such reduction of neutralizing antibodies are desirable because it is considered likely to help DSP compositions to retain its effectiveness without being neutralized, and it is associated with reduced risk of anaphylactic shocks, providing safer treatments of diseases. Longer interval regimens are also desirable in treatment of some of the diseases, because they strengthen the bias for $T_H2$ responses, which is considered to be the mode of action for the treatment of these diseases by DSPs.

In other embodiments, the DSP composition is administered in a treatment regimen which comprises at least one uneven time interval, wherein at least one of the time intervals is at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or the equivalent amount of days.

In one embodiment, the DSP composition is administered to be subject at least three times during a treatment regimen, such that there are at least two time intervals between administrations. These intervals may be denoted $I_1$ and $I_2$. If the DSP composition is administered four times, then there would be an additional interval between the third and fourth administrations, $I_3$, such that the number of intervals for a given number "n" of administrations is n−1. Accordingly, in one embodiment, at least one of the time intervals between administrations is greater than about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours. In another embodiment, at least 1%, 2%, 3%, 4%, 5%, 10%, 15%, 20%, 25%, 30%, 40%, 50%, 60%, 70%, 80%, 90% or 95% of the total number n−1 of time intervals are at least about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours.

In yet another embodiment, the average time interval between administrations (($I_1+I_2+\ldots+I_{n-1}$)/n−1) is at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or at least two weeks.

In another embodiment, the dosage regimen consists of two or more different interval sets. For example, a first part of the dosage regimen is administered to a subject daily, every other day, or every third day, for example, at about 22 mg copolymer/$m^2$ body surface area of the subject, wherein the subject is a human. In some embodiment of the invention, the dosing regimen starts with dosing the subject every other day, every third day, weekly, biweekly, or monthly. The dosage for administration every other day or every third day may be up to about 65 mg/$m^2$ and 110 mg/$m^2$ respectively. For a dosing regimen comprising dosing of the random copolymer every week, the dose comprises up to about 500 mg/$m^2$, and for a dosing regimen comprising dosing of the random copolymer every two weeks or every month, up to 1.5 g/$m^2$ may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 500 mg/$m^2$ body surface area weekly, up to maximum of about 1.5 g/$m^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/$m^2$ body surface area weekly. If, during the step-down dosage regimen, the disease condition relapses, the first dosage regimen may be resumed until effect is seen, and the second dosing regimen may be implemented. This cycle may be repeated multiple times as necessary.

In other embodiments of the invention, any of the methods of the invention may be practiced using sustained release formulation comprising a DSP composition. When administering a DSP composition of the invention using a sustained release formula, the overall exposure to the DSP is generally lower than in bolus administration. For example, a first part of the dosage regimen is administered to a subject daily, every other day, or every third day, for example, at about 22 mg DSP/$m^2$ body surface area of the subject, wherein the subject is a human. In some embodiment of the invention, the dosing regimen uses sustained release formula, dosing the subject every other day, every third day, weekly, biweekly, or monthly so that the copolymer is released during the interval. The dosage for administration every other day or every third day may be up to about 35 mg/$m^2$ and 65 mg/$m^2$ respectively. For a dosing regimen comprising dosing of the DSP composition every week, the dose comprises up to about 140 mg/$m^2$, and for a dosing regimen comprising dosing of the DSP composition every two weeks or every month, up to 750 mg/$m^2$ may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 140 mg/$m^2$ body surface area weekly, up to maximum of about 1.5 g/$m^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/$m^2$ body surface area weekly. If, during the step-down dosage regimen, the disease condition relapses, the first dosage regimen may be resumed until effect is seen, and the second dosing regimen may be implemented. This cycle may be repeated multiple times as necessary.

For such sustained release administration, such method comprises applying a sustained-release transdermal patch or implanting a sustained-release capsule or a coated implantable medical device so that a therapeutically effective dose of the copolymer of the present invention is delivered at defined time intervals to a subject of such a method. The DSP composition of the subject invention may be delivered via a capsule which allows regulated-release of the DSPs over a period of time. Controlled or sustained-release compositions include formulation in lipophilic depots (e.g., fatty acids, waxes, oils). Also comprehended by the invention are particulate compositions coated with polymers (e.g., poloxamers or poloxamines). In certain embodiments, a source of a DSP composition is stereotactically provided within or proximate to the area where pathology is observed or suspected.

An improvement in the symptoms of a subject afflicted with a disease as a result of administration of the DSP composition may be noted by a decrease in frequency of recurrences of episodes of the disease symptoms, by decrease in severity of symptoms, and by elimination of recurrent episodes for a period of time after the start of administration. A therapeutically effective dosage preferably reduces symptoms and frequency of recurrences by at least about 20%, for example, by at least about 40%, by at least about 60%, and by at least about 80%, or by about 100% elimination of one or more symptoms, or elimination of recurrences of the autoimmune disease, relative to untreated subjects. The period of time can be at least about one month, at least about six months, or at least about one year.

VII. Methods of Treatment—Administration of Antibodies Generated Using DSP

An aspect of the present invention is a method of treating a subject afflicted with a protein conformational disorder, comprising the steps of administering an antibody prepared using a DSP composition as described above. In a particular embodiment, the protein conformational disorder is Parkinson's disease. In another embodiment, the protein conformational disorder is dialysis-related amyloidosis. In another embodiment, the protein conformational disorder is Alzheimer's disease.

Another aspect of the present invention is a method of treatment using antibodies against a DSP composition related to a disease, in particular, a protein conformational disease. The antibodies useful for such method of treatment are antibodies generated against a DSP composition as described above, wherein the base sequence is a sequence of a protein known to be associated with a protein conformational disorder. More particularly, such protein is known to form an aggregate or fibril. In particular, antibodies thus generated are specific to the pathological conformation of such protein. The list of relevant diseases is recited above in this specification.

In an embodiment of this aspect of the invention, the antibodies for the use in the method of treatment are modified antibodies having an engineered Fc region, wherein the engineered Fc region confers favorable pharmacodynamic profiles. In one embodiment, the Fc region enhances clearance of antibody-antigen complex. In another embodiment, the Fc region is not immunogenic to the subject.

An aspect of the present invention is a method of treating a subject afflicted with a protein conformational disorder, comprising the steps of administering an antibody prepared using a DSP composition as described above. In a particular embodiment, the protein conformational disorder is Parkinson's disease. In another embodiment, the protein conformational disorder is dialysis-related amyloidosis. In another embodiment, the protein conformational disorder is Alzheimer's disease.

In an aspect of the invention, an antibody or antibodies identified by the method to generate antibodies against antigens associated with a protein conformational disease is cloned. The nucleic acids encoding such antibodies are cloned into an appropriate expression vector and delivered to a cellular site where such antibodies are desirable, at which site the antibodies are expressed.

Another aspect of the present invention is a method of treating a subject afflicted with a protein conformational disorder, comprising the steps of contacting under sterile conditions the blood of the subject to a membrane or a resin having conjugated with antibodies specific to a protein associated with a protein conformational disorder and prepared using a DSP composition, such antibodies described above, wherein the protein associated with a protein conformational disorder binds to such antibodies and is removed from the blood, and returning the blood to the subject. In a particular embodiment, the protein conformational disorder is dialysis-related amyloidosis. In one embodiment, the blood of the subject is contacted with the antibody as an additional step of therapeutic haemodialysis.

An embodiment of the invention is a method of prophylactic treatment of a subject at risk for developing a protein conformational disorder by contacting under sterile conditions the blood of the subject to a membrane or a resin having conjugated with antibodies specific to a protein associated with a protein conformational disorder and prepared using a DSP composition, such antibodies described above, wherein the protein associated with a protein conformational disorder binds to such antibodies and is removed from the blood, and returning the blood to the subject, whereby preventing the onset of such protein conformational disorder.

An aspect of the invention is a composition comprising a scaffold to which antibodies are attached, which antibodies are generated against a DSP composition as described above, wherein the base sequence is a sequence of a protein known to be associated with a protein conformational disorder. In one embodiment, the scaffold is a membrane compatible with haemodialysis. In a particular embodiment, the antibodies are conjugated to such membrane. In another embodiment, the antibodies are conjugated to a resin, such as CN—Br agarose resin (for example CN—Br Sepharose® (Pharmacia), to create an immunoaffinity resin.

VIII. Other Methods

The instant invention also comprises a method of creating antibody reagents for use in research studies, and such antibodies useful for research. Certain antibodies generated or selected by their specific binding to a DSP composition is useful to identify specific conformation of a protein in its pathological and non-pathological state. Such antibodies, when conjugated to scaffolds, are further useful for isolating and purifying the target proteins and peptides. Such antibodies are also useful in preclinical investigations of candidate pharmaceutical agents, wherein such agent may disrupt or disturb the binding of such antibodies to the target proteins. The antibodies can also be used to detect certain pathological antibodies and to measure the effects of such candidate pharmaceutical agents.

The instant invention also comprises a method of creating antibody reagents for use as diagnostic tools.

An embodiment of the invention, a method of diagnosing a protein conformational disorder, comprising: (i) contacting a biological sample from a subject with an antibody the invention; (ii) contacting a control sample with the antibody; and (iii) measuring specific binding of the antibody to an antigen in the sample; wherein specific binding of the antibodies to the antigen is indicative of the subject being afflicted with the disorder. A number of methods for measuring antibody-protein binding are known in the art, including ELISA, Western blotting, and spot-blot. The control sample may be a standard sample, a sample from a second subject known to be free of the pathology that is being investigated, or a sample from the same subject at a different time point to determine the chronological changes of the disease conditions. In some embodiments, tests are performed simultaneously using the antibody of the invention and a positive control antibody that confirms that the biological sample contains sufficient material. The positive control antibody may recognize any protein that is reasonably expected to be present in all samples (i.e. from both healthy and diseased patients), and may recognize a housekeeping enzyme (for example). In some embodiments, the binding of the antibody of the invention is quantified; in other embodiments, the binding is evaluated qualitatively.

More particularly, such disorder to be detected is one of the disorders enumerated elsewhere in this application.

In some embodiments, the diagnostic test may be performed in vivo, identifying the affected locations within the body. The antibody may be labeled in such a manner that it can be detected within a patient's body, e.g. with MRI. This label may be an iron-containing compound, such as ferrous and ferric-containing compounds, e.g. ferric-oxides. Specific examples include $Fe_2O_3$ and $Fe_3O_4$. Antibodies labeled with iron-containing compounds may also be used for in vitro diagnosis, e.g. when MRI is performed on a biological sample.

DEFINITIONS

The term "associated with" means "coexistent with" or "in correlation with." The term does not necessarily indicate causal relationship, though such relationship may exist.

The term "binding" refers to a direct association between two molecules, due to, for example, covalent, electrostatic, hydrophobic, ionic and/or hydrogen-bond interactions under physiological conditions, and including interactions such as salt bridges and water bridges.

The term "HLA molecule" means any class II major histocompatibility complex glycoproteins.

The term "immunomodulation" means the process of increasing or decreasing the immune system's ability to mount a response against a particular antigenic determinant through the T-cell receptor ("TCR")'s recognition of complexes formed by major histocompatibility complex ("MHC") and antigens.

The term "MHC activity" refers to the ability of an MEC molecule to stimulate an immune response, e.g., by activating T cells. An inhibitor of MHC activity is capable of suppressing this activity, and thus inhibits the activation of T cells by MHC. In preferred embodiments, a subject inhibitor selectively inhibits activation by a particular class II MHC isotype or allotype. Such inhibitors may be capable of suppressing a particular undesirable MHC activity without interfering with all MHC activity in an organism, thereby selectively treating an unwanted immune response in an animal, such as a mammal, preferably a human, without compromising the animal's immune response in general.

The term "patient" refers to an animal, preferably a mammal, including humans as well as livestock and other veterinary subjects.

The terms "peptide", "polypeptide" and "protein" are used interchangeably herein. These terms refer to unmodified amino acid chains, and also include minor modifications, such as phosphorylations, glycosylations and lipid modifications. The terms "peptide" and "peptidomimetic" are not mutually exclusive and include substantial overlap.

A "peptidomimetic" includes any modified form of an amino acid chain, such as a phosphorylation, capping, fatty acid modification and including unnatural backbone and/or side chain structures. As described below, a peptidomimetic comprises the structural continuum between an amino acid chain and a non-peptide small molecule. Peptidomimetics generally retain a recognizable peptide-like polymer unit structure. Thus, a peptidomimetic may retain the function of binding to a HLA protein forming a complex which activates autoreactive T cells in a patient suffering from an autoimmune disease.

The term "amino acid residue" is known in the art. In general the abbreviations used herein for designating the amino acids and the protective groups are based on recommendations of the IUPAC-IUB Commission on Biochemical Nomenclature (see *Biochemistry* (1972) 11:1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Most of the amino acids used in the DSPs of the present invention may exist in particular geometric or stereoisomeric forms. In preferred embodiments, the amino acids used to form the subject DSPs are (L)-isomers, although (D)-isomers may be included in the DSPs such as at non-anchor positions or in the case of peptidomimetic versions of the DSPs.

"Amino acid similarity", as used herein, means the relationship of those amino acids grouped together in FIG. 4, according to Kosiol, see reference above herein, based on the characteristics of the residues such as size, charge, hydrophobicity, etc. The amino acids grouped together are considered interchangeable, with high likelihood of retaining characteristics common among the group. As such, "according to amino acid similarity" used in conjunction with replacing or changing an amino acid means that a particular amino acid is replaced or changed to another amino acid in the same group (e.g., phenylalanine is replaced by tyrosine) of the table in FIG. 4. When there are more than 2 amino acids in a group, the priority of which amino acid replaces which depends on the circumstances presented.

"Naturally occurring variations", as used herein in reference to amino acids are allelic variations, isomeric and species differences of functionally equivalent proteins, naturally occurring amino acid modifications, whether or not incorporated while synthesis or post-synthesis (i.e. post-translation modification in vivo and post-synthesis modification in vitro) such as preformed phosphoylations, preformed nitrations, preformed glycosylations, modification by fatty acids (such as myristoylation), modified amino acid side chains including modification to produce amino acid analogs as described in paragraph defining "amino acid residue", cross-linking such as disulfide bonds, and other known modifications.

"Prevent", as used herein, means to delay or preclude the onset of, for example, one or more symptoms, of a disorder or condition.

"Treat", as used herein, means at least lessening the severity or ameliorating the effects of, for example, one or more symptoms, of a disorder or condition.

"Treatment regimen" as used herein, encompasses therapeutic, palliative and prophylactic modalities of administration of one or more compositions comprising one or more DSP compositions. A particular treatment regimen may last for a period of time at a particular dosing pattern, which will vary depending upon the nature of the particular disease or disorder, its severity and the overall condition of the patient, and may extend from once daily, or more preferably once every 36 hours or 48 hours or longer, to once every month or several months.

The terms "structure-activity relationship" or "SAR" refer to the way in which altering the molecular structure of drugs alters their interaction with a receptor, enzyme, etc.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999; and PCR Protocols, ed. by Bartlett et al., Humana Press, 2003; PHARMACOLOGY A Pathophysiologic Approach Edited by Josehp T.

DiPiro, Robert Talbert, Gary, Yee, Gary Matzke, Barbara Wells, and L. Michael Posey. 5th edition 2002 McGraw Hill; Pathologic Basis of Disease. Ramzi Cotran, Vinay Kumar, Tucker Collins. 6th Edition 1999. Saunders.

EXAMPLES

Example 1

Preparation of a DSP Composition from Fictitious Base Peptides

For ease of understanding, as an illustration, preparation of a DSP composition deriving from two fictitious peptide sequences, representing a known epitope, is described and shown in the table depicted in FIG. 6. In this illustration, the cassettes consist of five amino acids each, (x1, x2, x3, x4, x5=THMCE (SEQ ID NO: 15) in $y_1$ and PWKNA (SEQ ID NO: 16) in $y_2$). THMCE (SEQ ID NO: 15) is defined as having an input ratio of a-7, b-1, c-1, d-1, e-10. PWKNA (SEQ ID NO: 16) is defined as having an input ratio of a-1, b-3, c-3, d-3, e-20. For synthesis, the identity of group of amino acids occupying each amino acid position for each peptide is determined using the preferred method of amino acid substitution described by Kosiol et al., *J. Theoretical Biol.* 228:97-106, 2004, as shown in FIG. 4 (or less preferably an equivalent means of systematically altering amino acids), and the overall ratio of amino acids that occupy each of such positions in the resulting collective DSP composition is given above. Each cassette, $y_1$ and $y_2$, will twice be repeated two times, generating an order of $y_1\,y_1\,y_2\,y_2\,y_1\,y_1\,y_2\,y_2$. $N_n$ are the number of times the sequence within the cassette is to be repeated, and in our fictitious example N=2. MN can be any type of modifying moiety. MN must be amenable to solid phase synthesis methods. For this fictitious example, a modifying moiety of amino acids that would target the DSP to a certain location within a subject is chosen, such as an RGD-based sequence motif on a particular integrin such as alphaV-beta3. In this example the C-terminal modifier will also be an RGD-based motif, but comprised of D-amino acids.

The DSP composition as described above is prepared using a solid phase peptide synthesis method as described elsewhere in this disclosure.

Example 2

Preparation of a DSP Composition from Alpha-Synuclein Peptide

A DSP composition is designed from alpha-synuclein peptide (amino acid residues 121-137) using the preferred method of amino acid substitution described by Kosiol et al., *J. Theoretical Biol.* 228:97-106, 2004, as shown in FIG. 4. FIG. 7A shows a schematic for the design of an alpha-synuclein DSP peptide. Top panel shows the base peptide derived from human alpha-synuclein (amino acid residues 121-137) (DNEAYEMPSEEGYQDYE, SEQ ID NO: 6), The bottom panel illustrates the different proportions of alanine that may be used in the generation of each subunit. FIG. 7B shows the example of the application of the DSP Synthesis Rules in designing a DSP from the alpha-synuclein peptide. Throughout the peptide, alanine may be substituted. The number following the one-letter amino acid code is a molar percentage ratio of that amino acid in comparison to other amino acids in the same position. In this example, the final DSP peptides consists of three cassettes of the base peptide sequence. Alanine content increases from 60% to 70% in cassette 2, and to 80% in cassette 3. Where indicated, alanine content increases from 50% to 58% in cassette 2, and to 76% in cassette 3. The percentage of other amino acids change accordingly, wherein the molar percentage of the amino acids other than alanine are equal to each other. The first two amino acids (DN) may be subject to species alterations. For example, in mouse, they are G and S, respectively. In rat, they are both S.

The indicated serine may be phosphorylated. The indicated tyrosine residues may be tri-nitrated. Thus, the synthesized DSP composition, prepared using a solid phase peptide synthesis method as described elsewhere in this disclosure, may be postsynthetically modified by phosphorylating certain of the serines and/or tri-nitrating the tyrosine. The modification is carried out under such condition that allows for partial population of the DSP peptide to be modified, resulting a further diversified library of peptides.

Example 3

Preparation of a DSP Composition from $A\beta_{1\text{-}42}$ Base Peptide

A DSP composition is designed from $A\beta_{1\text{-}42}$ peptide using the preferred method of determining, for each amino acid position, the amino acid substitution described by Kosiol et al., *J. Theoretical Biol.* 228:97-106, 2004, as shown in FIG. 4, and the overall ratio of amino acids that occupy each of such positions in the resulting collective DSP composition. The substitution rule is shown in FIG. 9. Throughout the peptide, alanine may be substituted. Where the sequence originally contained alanine at the particular position, no substitution is designed in. The number following the one-letter amino acid code is a molar percentage ratio of that amino acid in comparison to other amino acids in the same position. In this example, the entire 42-amino acid long peptide is used as a base peptide and synthesis is carried out just one cycle. The resulting DSP is about 42-amino acid long.

Example 4

Preparation of a DSP Composition from Huntingtin Peptide

A DSP composition is designed from huntingtin peptide using the preferred method of determining, for each amino acid position, the amino acid substitution described by Kosiol et al., *J. Theoretical Biol.* 228:97-106, 2004, as shown in FIG. 4, and the overall ratio of amino acids that occupy each of such positions in the resulting collective DSP composition. The substitution rule is shown in FIG. 10. Throughout the peptide, alanine may be substituted. Where the sequence originally contained alanine at the particular position, no substitution is designed in. The number following the one-letter amino acid code is a molar percentage ratio of that amino acid in comparison to other amino acids in the same position. In this example, the 17-amino acid long peptide is used as a base peptide and synthesis is carried out just three cycles under the same condition. The resulting DSP is about 51-amino acid long.

The contents of any patents, patent applications, patent publications, or scientific articles referenced anywhere in this application are herein incorporated in their entirety. Additional references related to the disclosed invention is as follows.

ANDERSON, J., WALKER, D., GOLDSTEIN, J., DE LAAT, R., BANDUCCI, K., CACCAVELLO, R., BAR-

BOUR, R., HUANG, J., KLING, K., LEE, M., DIEP, L., KEIM, P., SHEN, Z., CHATAWAY, T., SCHLOSSMACHER, M., SEUBERT, P., SCHENK, D., SINHA, S., GAI, W., CHILCOTE, T. et al., "Phosphorylation of Ser-129 Is the Dominant Pathological Modification of α-Synuclein in Familial and Sporadic Lewy Body Disease" THE JOURNAL OF BIOLOGICAL CHEMISTRY, 281(40): 29739-29752 (2006).

BATTHYANY, C., SCHOPFER, F., BAKER, P., DURÁN, R., BAKER, L., HUANG, Y., CERVEÑANSKY, C., BRANCHAUD, B., FREEMAN, B. et al., "Reversible Post-translational Modification of Proteins by Nitrated Fatty Acids in Vivo" JOURNAL OF BIOLOGICAL CHEMISTRY, 281(29): 20450-20463 (2006).

BENJAMIN, D ILYIN, S. PLATA-SALAMAN, C. et al., "Alpha Synuclein Aggregation Assays" United States Patent Application Pub. No.: US 2003/0027210 (2003)

BENNER, E., BANERJEE, R., REYNOLDS, A., SHERMAN, S., PISAREV, V., TSIPERSON, V., NEMACHEK, C., CIBOROWSKI, P., PRZEDBORSKI, S., MOSLEY, R., GENDELMAN, H. et al., "Nitrated α-Synuclein Immunity Accelerates Degeneration of Nigral Dopaminergic Neurons" PLoS ONE, 1: 1-20 (2008).

BENNER, E., MOSLEY, R., DESTACHE, C., LEWIS, T., JACKSON-LEWIS, V., GORANTLA, S., NEMACHEK, C., GREEN, S., PRZEDBORSKI, S., GENDELMAN, H., et al., "Therapeutic immunization protects dopaminergic neurons in a mouse model of Parkinson's disease" PNAS, 101(25): 9435-9440 (2004).

BIERE, A., CITRON, M. et al., "α-Synucletin Super-Mutants Accelerate α-Synuclein Aggregation" U.S. Pat. No. 6,184,351 (2001)

BISAGLIA, M., TROLIO, A., BELLANDA, M., BERGANTINO E., BUBACCO, L., MAMMI, S. et al., "Structure and topology of the non-amyloid-β component fragment of human α-synuclein bound to micelles: Implications for the aggregation process" Protein Science, 15: 1408-1416 (2006).

CHILCOTE, T. BARBOUR, R. et al., "Antibodies to Alpha-Synuclein" United States Patent Application Pub. No.: US 2005/0196818 (2005)

CARDINALE, A., BIOCCA, S. et al., "The potential of intracellular antibodies for therapeutic targeting of protein-misfolding diseases" Trends in Molecular Medicine, 14(9): 373-380 (2008).

CHILCOTE, T., GOLDSTEIN, J., ANDERSON, J., GAI, W. et al., "Truncated Fragments of Alpha-Synuclein in Lewy Body Disease" U.S. Pat. No. 7,306,945 (2007)

CHILCOTE, T., GOLDSTEIN, J., ANDERSON, J., WALKER, D. et al., "Truncated Fragments of Alpha-Synuclein in Lewy Body Disease" U.S. Pat. No. 7,358,331 (2008).

CUI, T., SCHOPFER, F., ZHANG, J., CHEN, K., ICHIKAWA, T., BAKER, P., BATTHYANY, C., CHACKO, B., FENG, X., PATEL, R., AGARWAL, A., FREEMAN, A., CHEN, Y. et al., "Nitrated Fatty Acids: Endogenous Anti-inflammatory Signaling Mediators" JOURNAL OF BIOLOGICAL CHEMISTRY, 281(47): 35686-35698 (2006).

DANESH F., HO, L. et al., "Dialysis-Related Amyloidosis: History and Clinical Manifestations" Seminars in Dialysis, 14(2): 80-85 (2001).

DEL MAR, C., GREENBAUM, E., MAYNE, L., ENGLANDER, S. W., WOODS, V. et al., "Structure and properties of α-synuclein and other amyloids determined at the amino acid level" PNAS, 102(43): 15477-15482 (2005).

DESAI, B., MONAHAN, A., CARVEY, P., HENDEY, B. et al., "BloodBrain Barrier Pathology in Alzheimer's and Parkinson's Disease: Implications for Drug Therapy" Cell Transplantation, 16: 285-299 (2007).

DUDA, J., GIASSON, B., CHEN, Q., GUR, T., HURTIG, H., STERN, M., GOLLOMP, S., ISCHIROPOULOS, H., LEE, V., TROJANOWSKI, J. et al., "Widespread Nitration of Pathological Inclusions in Neurodegenerative Synucleinopathies" American Journal of Pathology, 157(5): 1439-1445 (2000).

EAKIN, C., ATTENELLO, F., MORGAN, C., MIRANKER, A. et al., "Oligomeric Assembly of Native-like Precursors Precedes Amyloid Formation by β2 Microglobulin", American Chemical Society, 43(24): 7808-7815 (2004).

EL-AGNAF, O., IRVINE, G. et al., "Aggregation and neurotoxicity of a-synuclein and related peptides" Bio Chemistry Transactions, 30(4): 559-565 (2002).

FRANGIONE, B., WISNIEWSKI, T., SIGURDSSON, M. et al., "Synthetic Immunogenic but Non-Deposit-Forming Polypeptides and Peptides Homologous to Amyloid Beta, Prion Protein" United States Patent Application Pub. No.: US 2003/0166558 (2003)

GIASSON, B., DUDA, J., MURRAY, I., CHEN, Q., SOUZA, J., HURTIG, H., ISCHIROPOULOS, H., TROJANOWSKI, J., LEE, V. et al., "Oxidative Damage Linked to Neurodegeneration by Selective α-Synuclein Nitration in Synucleinopathy Lesions" SCIENCE, 290: 985-989 (2000).

GORBATYUK, O., LI, S., SULLIVAN, L., CHEN, W., KONDRIKOVA, G., MANFREDSSON, F., MANDEL, R., MUZYCZKA, N. et al., "The phosphorylation state of Ser-129 in human α-synuclein determines neurodegeneration in a rat model of Parkinson disease" PNAS, 105(2): 763-768 (2007).

HIRSCH, E., HUNOT, S. et al., "Neuroinflammation in Parkinson's disease: a target for neuroprotection?" Neurology, 8: 382-397 (2009).

HOSHINO, M., KATOU, H., HAGIHARA, Y., HASEGAWA, K., NAIKAI, H., GOTO, Y. et al. "Mapping the core of the β2-microglobulin amyloid fibril by H/D exchange", nature structural biology, 9(5):332-336 (2002).

LAURIE, C., REYNOLDS, A., COSKUN, O., BOWMAN, E., GENDELMAN, H. and MOSLEY, R. et al., "CD4+ T cells from Copolymer-1 immunized mice protect dopaminergic neurons in the 1-methyl-4-phenyl-1,2,3,6-tetrahydropyridine model of Parkinson's disease" Journal of Neuroimmunology, 183: 60-68 (2007).

LANGSTON J. et al., "Methods and Systems for Identifying Compounds that Modulate Alpha-Synuclein Aggregation" United States Patent Application Pub. No.: US 2007/0214509 (2007)

LEE, S. et al., "Origins and Effects of Extracellular α-synuclein: Implications in Parkinson's Disease" J Mol Neurosci, 34: 17-22 (2007).

LEVIN, J., GIESE, A., BOETZEL, K., ISRAEL, L., 27 HÖGEN, T., NÜBLING, G., KRETZSCHMAR, H., LORENZL, S. et al., "Increased α-synuclein aggregation following limited cleavage by certain matrix metalloproteinases" Experimental Neurology, 215: 201-208 (2008).

MADINE, J., DOIG, A. J., KITMITTO A., MIDDLETON, D. A. et al., "Studies of the aggregation of an amyloidogenic α-synuclein peptide fragment" Biochemical Society Transactions, 33(5): 1113-1115 (2005).

MADINE, J., DOIG, A. J., MIDDLETON, D. A., et al., "The aggregation and membrane-binding properties of an α-synuclein peptide fragment" *Biochemical Society Transactions*, 32(6): 1127-1129 (2004).

MASLIAH, E., HASHIMOTO, M., ROCKENSTEIN, E. et al., "Method for Screening for Anti-Amyloidogenic Properties and Method for Treatment of Neurodegenerative Disease" U.S. Pat. No. 7,226,746 (2007)

MASLIAH, E., ROCKENSTEIN, E., ADAME, A., ALFORD, M., CREWS, L., HASHIMOTO, M., SEUBERT, P., LEE, M., GOLDSTEIN, J., CHILCOTE, T., GAMES, D., SCHENK, D. et al., "Effects of α-Synuclein Immunization in a Mouse Model of Parkinson's Disease" *Neuron*, 46: 857-868 (2005).

SCHENK, D., MASLIAH, E. et al., "Prevention and Treatment of Synucleinopathic Disease"—United States Patent Application Pub. No.: US 2004/0136993 (2004).

SCHENK, D., MASLIAH, E. et al., "Prevention and Treatment of Synucleinopathic Disease" United States Patent Application Pub. No.: US 2004/0146521 (2004)

SCHENK, D., MASLIAH, E. et al., "Prevention and Treatment of Synucleinopathic and Amyloidogenic Disease" United States Patent Application Pub. No.: US 2005/0037013 (2005)

SCHENK, D., MASLIAH, E., BUTTINI, E., CHILCOTE, T., ROCKENSTEIN, E., GAMES, K., "Prevention and Treatment of Synucleinopathic Disease" United States Patent Application Pub. No.: US 2006/0058233 (2006)

SCHENK, D., GAMES, K., BUTTINI, E., CHILCOTE, T., ROCKENSTEIN, E., MASLIAH, E., "Prevention and Treatment of Synucleinopathic and Amyloidogenic Disease" United States Patent Application Pub. No.: US 2008/0014194 (2008)

THOMAS, B., BEAL, M. et al., "Parkinson's disease" *Human Molecular Genetics*, 16(2): R183-R194 (2007).

TSAI, S. et al., "Glatiramer acetate could be a potential therapeutic agent for Parkinson's disease through its neuroprotective and anti-inflammatory effects" *Medical Hypotheses*, 69: 1219-1221 (2007).

VILAR, M., CHOU, H., LOHRS, T., MAJI, S., RIEK-LOHER, D., VEREL, R., MANNING, G., STAHLBERG, H., RIEK, R. et al., "The fold of α-synuclein fibrils" *PNAS*, 105(25): 8637-8642 (2008).

WANG, C., ZHOU, H., MCGUIRE, J., CERULLO, V., LEE B., LI, S., LI, X. et al., "Suppression of neuropil aggregates and neurological symptoms by an intracellular antibody implicates the cytoplasmic toxicity of mutant huntingtin" *J. Cell Biol.*, 181(5): 803-816 (2008).

WILMS, H., ZECCA, L., ROSENSTIEL, P., SIEVERS, J., DEUSCHL, G. and LUCIUS, R. et al., "Inflammation in Parkinson's Diseases and Other Neurodegenerative Diseases: Cause and Therapeutic Implications" *Current Pharmaceutical Design*, 13: 1925-1928 (2007).

YACOUBIAN, T., STANDAERT, D. et al., "Targets for neuroprotection in Parkinson's disease" *Biochimica et Biophysica Acta*, 4: 1-12 (2008).

YAMAMOTO, S., GEJYO, F. et al., "Historical background and clinical treatment of dialysis-related amyloidosis" *Biochimica et Biophysica Acta*, 1753: 4-10 (2005).

ZHOU, C., EMADI, S., SIERKS, M., MESSER, A. et al., "A Human Single-Chain Fv Intrabody Blocks Aberrant Cellular Effects of Overexpressed α-Synuclein" *MOLECULAR THERAPY*, 10(6): 1023-1031 (2004).

FREESE, A. et al., "HLA-B7 B-pleated sheet-derived synthetic peptides are immunodominant T-cell epitopes regulating alloresponces", *Blood*, 99(9): 3286-3292 (2002).

Kessler, J. H., *J. Exp. Med.* 193(1):73-88 (2001).

Liu, G., *J. Immunother.* 26(4):301-12 (1997)

Pedersen, L. Ø., *J. Investig. Dermatol.* 118: 595-599 (2002)

U.S. Pat. No. 6,063,900

Hernandez, J., *Eur J Immunol*, 34:2331-41 (2004)

Diamond, D. et al., *Blood* 90:1751-57 (1997)

Belyakov, I., *Proc. Nat. Acad. Sci. USA*, 95:1709 (1998)

U.S. Pat. No. 7,232,887

Näslund, J. et al., *Proc. Nat. Acad. Sci. USA*, 91: 8378-8382 (1994)

Gandy, S., *J. Clin. Invest.* 115(5): 1121-1129 (2005)

Benner, E. J. et al., PLoS ONE 3(1): e1376 (2008)

Campion, D. et al. "The NACP/synuclein gene: chromosomal assignment and screening for alterations in Alzheimer disease" *Genomics* 26 (2), 254-257 (1995)

Lecerf, J.-M. et al., *Proc Natl Acad Sci USA.* 98(8): 4764-4769 (2001)

Kozhukh, G V et al., JBC, Vol. 277, No. 2, Issue of January 11, pp. 1310-1315, 2002.

Niwa T, Seminars in Dialysis—Vol 14, No 2 (March-April) 2001 pp. 123-126

---

Sequence Listings in addition to Table I

SEQ ID NO: 9

```
Beta-2-microglobulin - human (P61769-1)
MSRSVALAVL ALLSLSGLEA IQRTPKIQVY SRHPAENGKS NFLNCYVSGF
HPSDIEVDLL KNGERIEKVE HSDLSFSKDW SFYLLYYTEF TPTEKDEYAC
RVNHVTLSQP KIVKWDRDM
```

SEQ ID NO: 10

```
HUMAN PRION PROTEIN (AAH22532)
MANLGCWMLV LFVATWSDLG LCKKRPKPGG WNTGGSRYPG QGSPGGNRYP
PQGGGWGQP HGGGWGQPHG GGWGQPHGGG WGQPHGGGWG QGGGTHSQWN
KPSKPKTNMK HMAGAAAGA VVGGLGGYVL GSAMSRPIIH FGSDYEDRYY
RENMHRYPNQ VYYRPMDEYS NQNNFVHDCV NITIKQHTVT TTTKGENFTE
TDVKMMERVV EQMCITQYER ESQAYYKRGS SMVLFSSPPV ILLISFLIFL IVG
```

SEQ ID NO: 11

```
HUMAN SOD1 (CAG46542)
MATKAVCVLK GDGPVQGIIN FEQKESNGPV KVWGSIKGLT EGLHGFHVHE
FGDNTAGCTS AGPHFNPLSR KHGGPKDEER HVGDLGNVTA DKDGVADVSI
EDSVISLSGD HCIIGRTLVV HEKADDLGKG GNEESTKTGN AGSRLACGVI GIAQ
```

SEQ ID NO: 12

```
HUMAN HUNTINGTIN (
   1  matleklmka feslksfqqq qqqqqqqqq qqqqqqqqq pppppppppp pqlpqpppqa
  61  qpllpqpqpp ppppppppgp avaeeplhrp kkelsatkkd rvnhcltice nivaqsvrns
```

Sequence Listings in addition to Table I

```
 121  pefqkllgia  melfllcsdd  aesdvrmvad  eclnkvikal  mdsnlprlql  elykeikkng
 181  aprslraalw  rfaelahlvr  pqkcrpylvn  llpcltrtsk  rpeesvqetl  aaavpkimas
 241  fgnfandnei  kvllkafian  lkssssptirr taagsavsic  qhsrrtqyfy  swllnvllgl
 301  lvpvedehst  lllilgvlltl rylvpllqqq  vkdtslkgsf  gvtrkemevs  psaeqlvqvy
 361  eltlhhtqhq  dhnvvtgale  llqqlfrtpp  pellqtltav  ggigqltaak  eesggrsrsg
 421  siveliaggg  sscspvlsrk  qkgkvllgee  ealeddsesr  sdvsssalta  svkdeisgel
 481  aassgvstpg  saghdiiteq  prsqhtlqad  svdlascdlt  ssatdgdeed  ilshsssqvs
 541  avpsdpamdl  ndgtqasspi  sdssqttteg  pdsavtpsds  seivldgtdn  qylglqigqp
 601  qdedeeatgi  lpdeaseafr  nssmalqqah  llknmshcrq  psdssvdkfv  lrdeatepgd
 661  qenkpcrikg  digqstddds  aplvhcvrll  sasflltggk  nvlvpdrdvr  vsvkalalsc
 721  vgaavalhpe  sffsklykvp  ldtteypeeq  yvsdilnyid  hgdpqvrgat  ailcgtlics
 781  ilsrsrfhvg  dwmgtirtlt  gntfsladci  pllrktlkde  ssvtcklact  avrncvmslc
 841  sssyselglq  liidvitlrn  ssywlvrtel  letlaeidfr  lvsfleakae  nlhrgahhyt
 901  gllklqervl  nnvvihllgd  edprvrhvaa  aslirlvpkl  fykcdqgqad  pvvavardqs
 961  svylkllmhe  tqppshfsvs  titriyrgyn  llpsitdvtm  ennlsrviaa  vshelitstt
1021  raltfgccea  lcllstafpv  ciwslgwhcg  vpplsasdes  rksctvgmat  miltllssaw
1081  fpldlsahqd  alilagnlla  asapkslrss  waseeeanpa  atkqeevwpa  lgdralvpmv
1141  eqlfshllkv  inicahvldd  vapgpaikaa  lpsltnppsl  spirrkgkek  epgeqasvpl
1201  spkkgseasa  asrqsdtsgp  vttsksssslg sfyhlpsylk  lhdvlkatha  nykvtldlqn
1261  stekfggflr  saldvlsqil  elatlqdigk  cveeilgylk  scfsrepmma  tvcvqqllkt
1321  lfgtnlasqf  dglssnpsks  qgraqrlgss  svrpglyhyc  fmapythftq  aladaslrnm
1381  vqaeqendts  gwfdvlqkvs  tqlktnltsv  tknradknai  hnhirlfepl  vikalkqytt
1441  ttcvqlqkqv  ldllaqlvql  rvnyclldsd  qvfigfvlkq  feyievgqfr  eseaiipnif
1501  fflvllsyer  yhskqiigip  kiiqlcdgim  asgrkavtha  ipalqpivhd  lfvlrgtnka
1561  dagkeletqk  evvvsmllrl  iqyhqvlemf  ilvlqqchke  nedkwkrlsr  qiadiilpml
1621  akqqmhidsh  ealgvlntlf  eilapsslrp  vdmllrsmfv  tpntmasvst  vqlwisgila
1681  ilrvlisqst  edivisriqe  lsfspylisc  tvinrlrdgd  ststleehse  gkqiknlpee
1741  tfsrfllqlv  gillediwtk  qlkvemseqq  htfycqelgt  llmclihifk  sgmfrritaa
1801  atrlfrsdgc  ggsfytldsl  nlrarsmitt  hpalvllwcq  illlvnhtdy  rwwaevqqtp
1861  krhslsstkl  lspqmsgeee  dsdlaaklgm  cnreivrrga  lilfcdyvcq  nlhdsehltw
1921  livnhiqdli  slsheppvqd  fisavhrnsa  asglfiqaiq  srcenlstpt  mlkktlqcle
1981  gihlsqsgav  ltlyvdrllc  tpfrvlarmv  dilacrrvem  llaanlqssm  aqlpmeelnr
2041  iqeylqssgl  aqrhqrlysl  ldrfrlstmq  dslspsppvs  shpldgdghv  sletvspdkd
2101  wyvhlvksqc  wtrsdsalle  gaelvnripa  edmnafmmns  efnlsllapc  lslgmseisg
2161  gqksalfeaa  revtlarvsg  tvqqlpavhh  vfqpelpaep  aaywsklndl  fgdaalyqsl
2221  ptlaralaqy  lvvvsklpsh  lhlppekekd  ivkfvvatle  alswhliheq  iplsidlqag
2281  ldccclalql  pglwsvvsst  efvthacsli  ycvhfileav  avqpgeqlls  perrtntpka
2341  iseeeeevdp  ntqnpkyita  acemvaemve  slqsvlalgh  krnsgvpafl  tpllrniiis
2401  larlplvnsy  trvpplvwkl  gwspkpggdf  gtafpeipve  flqekevfke  fiyrintlgw
2461  tsrtqfeetw  atllgvlvtq  plvmeqeesp  peedtertqi  nvlavqaits  lvlsamtvpv
2521  agnpavscle  qqprnkplka  ldtrfgrkls  iirgiveqei  qamvskreni  athhlyqawd
2581  pvpslspatt  galishekll  lqinperelg  smsyklgqvs  ihsvwlgnsi  tplreeewde
2641  eeeeeadapa  pssppptspvn srkhragvdi  hscsqfllel  ysrwilpsss  arrtpailis
2701  evvrsllvvs  dlfternqfe  lmyvtltelr  rvhpsedeil  aqylvpatck  aaavlgmdka
2761  vaepvsrlle  stlrsshlps  rvgalhgvly  vlecdllddt  akqlipvisd  yllsnlkgia
2821  hcvnihsqqh  vlvmcatafy  lienypldvg  pefsasiiqm  cgvmlsgsee  stpsiiyhca
2881  lrglerllls  eqlsrldaes  lvklsvdrvn  vhsphramaa  lglmltcmyt  gkekvspgrt
2941  sdpnpaapds  esvivamerv  svlfdrirkg  fpcearvvar  ilpqflddff  ppqdimnkvi
3001  geflsnqqpy  pqfmatvvyk  vfqtlhstgq  ssmvrdwvml  slsnftqrap  vamatwslsc
3061  ffvsastspw  vaailphvis  rmgkleqvdv  nlfclvatdf  yrhqieeeld  rrafqsvlev
3121  vaapgspyhr  lltclrnvhk  vttc
                                                                SEQ ID NO: 13
MOUSE ALPHA SYNUCLEIN (NP_001035916)
MDVFMKGLSK AKEGVVAAAE KTKQGVAEAA GKTKEGVLYV GSKTKEGVVH
GVTTVAEKTK EQVTNVGGAV VTGVTAVAQK TVEGAGNIAA ATGFVKKDQM
GKGEEGYPQE GILEDMPVDP GSEAYEMPSE EGYQDYEPEA
```

What is claimed is:

1. A process for manufacturing a composition comprising directed-sequence polymers (DSPs), comprising the steps of:
   (1) selecting a first base peptide sequence, wherein the sequence is an amino acid sequence of an epitope of an antigen associated with a protein conformational disorder;
   (2) synthesizing by solid phase peptide synthesis a first cassette of the DSPs, the cassette having a sequence of amino acid positions corresponding to each amino acid of the base peptide sequence,
   wherein, for at least one amino acid position of the first cassette of the DSPs, an amino acid is added, said amino acid randomly selected from a mixture of amino acids comprising an original amino acid found at the corresponding amino acid position of the base peptide sequence, alanine (A), and, optionally, at least one amino acid serving as a conserved substitution,
      wherein the amino acids in the mixture are present in a fixed molar input ratio relative to each other, determined prior to starting synthesis,
      wherein the relative molar amount of A is more than 10% and less than 90% of the total amino acid concentration of the DSPs;
   (3) optionally extending the length of the DSPs by
      (a) repeating step (2) for 1 to 15 cycles and elongating the DSP under the same condition including the input ratio of amino acids in the mixture;
      (b) repeating step (2) for 1 to 15 cycles and elongating the DSP, for each cycle, using a different input ratio of amino acids in the mixture;
      (c) repeating steps (1) and (2) for 1 to 15 cycles and elongating the DSP using cassettes based on more than one base peptide;
      (d) assembling 1 to 15 cassettes synthesized in a single cycle of step (2); or
      (e) assembling 1 to 15 cassettes, the first cassette synthesized under one condition of step (2), and second and more cassettes synthesized under one or more different conditions of step (2);
   wherein the number of cycles selected in steps (3) is selected so that the final length of the DSP is about 10 to 300 amino acid residues, and
   wherein the complexity of the linear DSP composition is greater than $5 \times 10^2$ different peptides.

2. The process according to claim 1, wherein the antigen is associated with a protein conformational disorder affecting the central and/or peripheral nervous system or with a protein conformational disorder affecting multiple organs or organs other than the central nervous system.

3. The process according to claim 2, wherein the antigen is associated with a disease selected from Alzheimer's disease (AD), Dutch hereditary cerebral hemorrhage with amyloidosis (a.k.a cerebrovascular amyloidosis), congophilic angiopathy; Pick's disease, progressive supranuclear palsy; familial British dementia; Parkinson's disease (PD), Lewy-body related diseases, multiple system atrophy, Hallervorden-Spatz disease; amyotrophic lateral sclerosis (ALS); Huntington's disease (HD); spinocerebellar ataxia; neuronal intranuclear inclusion disease; hereditary dentatorubral-pallidoluysian atrophy; prion-related diseases such as scrapie, bovine spongiform encephalopathy, variant Creutzfeldt Jakob disease, Gerstmann-Sträussler-Scheinker syndrome, kuru, fatal familial insomnia, and related disorders; hereditary cystatin c amyloid angiopathy; dementia pugilistica; other neurodegenerative diseases characterized by cerebral and nerve atrophy; and spinal and bulbar muscular atrophy; hereditary systemic and cerebral amyloidosis, Finnish-type familial amyloidosis; senile systemic amyloidosis (a.k.a, senile cardiac amyloidosis), familial amyloid polyneuropathy; Type-2 diabetes, in particular pancreatic islet amyloidosis; dialysis-related amyloidosis (DRA); inflammation-associated reactive systemic amyloidosis (a.k.a. AA amyloidosis); aortic medial amyloidosis; medulary carcinoma of the thyroid; hereditary renal amyloidosis; light chain associated amyloidosis, light chain deposition disease, light chain cast nephropathy, light chain cardiomyopathy; atrial amyloidosis; injection-localized amyloidosis; cystic fibrosis (CF); and sickle cell anemia; wherein fibrillogenesis is observed in the affected organs or tissues.

4. The process according to claim 3, wherein the disease is Parkinson's disease.

5. The process according to claim 3, wherein the protein conformational disease is dialysis-related amyloidosis.

6. The process according to claim 1, wherein the first base peptide sequence is selected from prion protein, amyloid beta protein, abri protein, tau protein, alpha-synuclein, alpha-synuclein central fragment, islet amyloid polypeptide (a.k.a, amylin), prothymosin alpha, amino-terminal domain of androgen receptor protein, ataxin-1, DRPLA protein (a.k.a, atrophin-1), calcitonin, cystatin c, transthyretin, beta 2 microglobulin, serum amyloid A protein, huntingtin, exon I of huntingtin, immunoglobulin light chain variable domains, insulin, lysozyme, alpha lactalbumin, monellin, ligand- and DNA-binding domains of androgen receptor protein, lactadherin, lactadherine fragment (a.a, residue 245-294, a.k.a, medin), gelsolin, apolipoprotein A1, fibrinogen, atrial natriuretic factor, and fragments thereof.

7. The process according to claim 1, wherein the base peptide sequence from which the DSP sequences are derived is selected from a group consisting of SEQ ID NO: 3 through 13.

8. The process according to claim 1, wherein A is more than about 10% and less than about 70% of the total amino acid concentration of the DSPs.

9. The process according to claim 1, wherein A is more than about 15% and less than about 50% of the total amino acid concentration of the DSPs.

10. The process according to claim 1, wherein the conserved substitution is defined according to the amino acid similarity table shown in FIG. 4.

11. The process according to claim 1, wherein the conserved substitution is determined based on empirical data of known naturally occurring variants of the epitope.

12. The process according to claim 1, wherein an immune response elicited by a peptide having the first base sequence is inadequate for preventing, ameliorating, or overcoming the pathology associated with the epitope.

13. The process according to claim 1, wherein the isolated peptide having the first base sequence, when administered on its own as an antigen, and not in conjunction with the DSP, to a patient in need thereof in order to elicit an immune response, elicits a detrimental immune response.

14. The process according to claim 13, wherein the detrimental immune response is an autoimmune response against non-pathological tissue in vivo.

15. The process according to claim 13, wherein the detrimental immune response is an immunological reaction that is detrimental to the improvement of the disease condition.

16. The process according to claim 1 wherein, for each amino acid position of the first cassette of the DSPs, an amino acid is added, said amino acid randomly selected from a mixture of amino acids comprising an original amino acid found at the corresponding amino acid position of the base peptide sequence, alanine (A), and, optionally, at least one amino acid serving as a conserved substitution.

17. The process according to claim 1, wherein at least one of the amino acids serving as a conserved substitution is a nitrated or phosphorylated amino acid.

\* \* \* \* \*